(12) United States Patent
Yang et al.

(10) Patent No.: US 10,684,294 B2
(45) Date of Patent: Jun. 16, 2020

(54) DIARYLETHER-BASED FLUOROGENIC PROBES FOR DETECTION OF HYPOCHLOROUS ACID OR HYDROXYL RADICAL

(71) Applicant: THE UNIVERSITY OF HONG KONG, Hong Kong (HK)

(72) Inventors: Dan Yang, Hong Kong (HK); Jun Hu, Hong Kong (HK); Nai-Kei Wong, Hong Kong (HK); Xiaoyu Bai, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 401 days.

(21) Appl. No.: 15/135,788

(22) Filed: Apr. 22, 2016

(65) Prior Publication Data

US 2016/0312033 A1    Oct. 27, 2016

Related U.S. Application Data

(60) Provisional application No. 62/151,075, filed on Apr. 22, 2015.

(51) Int. Cl.
| | | |
|---|---|---|
| *A61B 5/00* | (2006.01) |
| *A61B 8/00* | (2006.01) |
| *A61B 10/00* | (2006.01) |
| *G01N 33/84* | (2006.01) |
| *C07D 493/10* | (2006.01) |
| *C07D 491/20* | (2006.01) |
| *G01N 33/58* | (2006.01) |
| *C09B 11/08* | (2006.01) |
| *A61K 49/00* | (2006.01) |

(52) U.S. Cl.
CPC .......... *G01N 33/84* (2013.01); *C07D 491/20* (2013.01); *C07D 493/10* (2013.01); *C09B 11/08* (2013.01); *G01N 33/582* (2013.01); *A61K 49/001* (2013.01)

(58) Field of Classification Search
None
See application file for complete search history.

(56) References Cited

U.S. PATENT DOCUMENTS 8,148,423 B2 * 4/2012 Yang .................... G01N 33/582
514/449

* cited by examiner

*Primary Examiner* — Michael G. Hartley
*Assistant Examiner* — Melissa J Perreira
(74) *Attorney, Agent, or Firm* — Amin, Turocy & Watson, LLP

(57) ABSTRACT

Provided herein are improved fluorogenic compounds and probes that can be used as reagents for measuring, detecting and/or screening hypochlorous acid or hydroxyl radical. The fluorogenic compounds of the invention can produce fluorescence colors, such as green, yellow, red, or far-red. Also provided herein are fluorogenic compounds for selectively staining hypochlorous acid or hydroxyl radical in the mitochondria of living cells. Provided also herein are methods that can be used to measure, directly or indirectly, the presence and/or amount of hypochlorous acid or hydroxyl radical in chemical samples and biological samples such as cells and tissues in living organisms. Also provided are high-throughput screening methods for detecting or screening hypochlorous acid or hydroxyl radical or compounds that can increase or decrease the level of hypochlorous acid or hydroxyl radical in chemical and biological samples.

9 Claims, 11 Drawing Sheets

DIARYLETHER-BASED FLUOROGENIC PROBES FOR DETECTION OF HYPOCHLOROUS ACID OR HYDROXYL RADICAL

CROSS REFERENCE TO RELATED APPLICATIONS

This application claims priority to provisional application Ser. No. 62/151,075, filed on Apr. 22, 2015, which is incorporated herein by reference.

TECHNICAL FIELD

Described herein are fluorogenic probe compositions containing compounds of specific formula. Using the compounds of specific formula, also described herein are methods for detecting the presence of and/or determining the level of superoxide in samples, methods for detecting the presence of or determining the level of hypochlorous acid or hydroxyl radical in vivo in an organism, high-throughput screening methods for detecting the presence of, or determining the level of, hypochlorous acid or hydroxyl radical in samples, and high-throughput methods for screening one or more target compounds that increase or decrease the level of hypochlorous acid or hydroxyl radical.

BACKGROUND 2,7-dichlorofluorescein (DCF) is currently the most successful commercial probe for hypochlorous acid (HOCl), but it suffers from poor selectivity and sensitivity. Previous reports have suggested that the probes for HOCl have various limitations in terms of sensitivity, selectivity, chemostability, and photostability toward reactive oxygen species (ROS) and a negligible response toward HOCl.

SUMMARY

Aspects of the present invention provide compounds of formula (I) or (II):

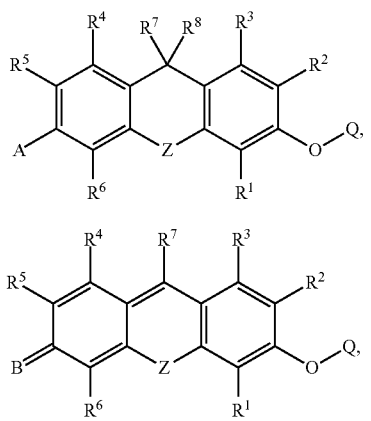

or a tautomer thereof;

wherein each of $R^1$ and $R^2$ is independently F, Cl or H;

wherein each of $R^3$, $R^4$, $R^5$ and $R^6$ is independently H, F, Cl, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphonic acid, phosphate ester, sulfonic acid (—SO$_3$H), sulfonate ester, sulfonamide, —C(=O)—P$^1$ or —C(=O)-M-P$^2$;

wherein each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms; wherein M is alkylene, alkenylene, alkynylene, arylene, aralkylene or alkarylene;

wherein A is OR$^9$ or NR$^{10}$R$^{11}$;

wherein R$^9$ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;

wherein each of R$^{10}$ and R$^{11}$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl; or wherein R$^{10}$ in combination with R$^{11}$ forms a saturated 5- or 6-membered heterocycle that is a piperidine, a morpholine, a pyrrolidine or a piperazine, each of which is optionally substituted by alkyl, carboxylic acid, a salt of carboxylic acid, or a carboxylic acid ester of an alcohol; or wherein R$^{10}$ in combination with R$^5$, or R$^{11}$ in combination with R$^6$, or both, form a 5- or 6-membered ring that is saturated or unsaturated, or further fused with an aryl or heteroaryl ring, and is optionally substituted by one or more alkyls, carboxylic acids, sulfonic acids (—SO$_3$H), or their salts, ester or amide derivatives;

wherein B is O or N$^+$R$^{10}$R$^{11}$;

wherein Z is O, S, NR$^{12}$, CR$^{12}$R$^{13}$, SiR$^{12}$R$^{13}$, GeR$^{12}$R$^{13}$, or SnR$^{12}$R$^{13}$;

wherein each of R$^{12}$ and R$^{13}$ is independently H, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, hydroxy, thiol, thioalkyl, alkoxy, alkylthio, alkoxyalkyl, aryloxy, arylalkoxy, acyloxy, carbamoyl, trifluoromethyl, phenoxy, benzyloxy, phosphonic acid, phosphate ester, sulfonic acid (—SO$_3$H), sulfonate ester, sulfonamide, carboxylic acid, carboxylic ester, or carboxylic amide; or wherein R$^{12}$ in combination with R$^{13}$ forms a saturated 5- or 6-membered heterocycle that is optionally substituted by alkyl, carboxylic acid, a salt of carboxylic acid, or a carboxylic acid ester of an alcohol;

wherein R$^7$ is H, CF$_3$, CN, a carboxylic acid, a salt of carboxylic acid, or a carboxylic acid ester of an alcohol; or wherein R$^7$ is a saturated or unsaturated alkyl that is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—SO$_3$H), sulfonate ester (—SO$_3$R$^{14}$), sulfonamide (—SO$_2$NR$^{14}$R$^{15}$), wherein each of R$^{14}$ and R$^{15}$ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium; or wherein R$^7$ has the formula

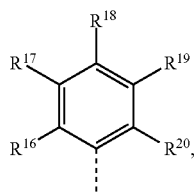

(III)

wherein each of $R^{16}$, $R^{17}$, $R^{18}$, $R^{19}$ and $R^{20}$ is independently H, F, Cl, Br, I, CN, nitro, a carboxylic acid, a salt of carboxylic acid, sulfonic acid (—$SO_3H$), sulfonate ester (—$SO_3R^{14}$), sulfonamide (—$SO_2NR^{14}R^{15}$), hydroxy, azide, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{14}$), or sulfonamide (—$SO_2NR^{14}R^{15}$); or wherein $R^{16}$ and $R^{17}$ together, $R^{17}$ and $R^{18}$ together, $R^{18}$ and $R^{19}$ together, or $R^{19}$ and $R^{20}$ together form a part of a 5- or 6-membered cycloalkyl, heterocyclyl, aryl or heteroaryl ring fused with the phenyl ring of formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{14}$), or sulfonamide (—$SO_2NR^{14}R^{15}$);

wherein $R^8$ is H, hydroxy, CN or alkoxy; or wherein $R^7$ in combination with $R^8$ forms a 5-membered spirolactone or spirolactam ring or a 5-membered spirosultam ring; or wherein $R^8$ in combination with $R^{16}$ or $R^{20}$ forms a 5- or 6-membered spirolactone or spirolactam ring or a 5- or 6-membered spirosultone or spirosultam ring that is optionally and independently substituted by H, F or $CH_3$; and wherein Q is a substituted phenyl represented by formula (IV):

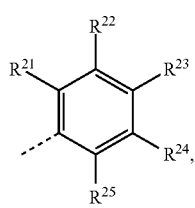

(IV)

wherein each of $R^{21}$, $R^{22}$, $R^{23}$, $R^{24}$, and $R^{25}$ is independently H, hydroxy, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{14}$), or sulfonamide (—$SO_2NR^{15}R^{16}$); or wherein $R^{21}$ and $R^{22}$ together, $R^{22}$ and $R^{23}$ together, $R^{23}$ and $R^{24}$ together, or $R^{24}$ and $R^{25}$ together form a part of a 5- or 6-membered cycloalkyl, heterocyclyl, aryl or heteroaryl ring fused with the phenyl ring of formula (IV) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{14}$), or sulfonamide (—$SO_2NR^{14}R^{15}$).

In another aspect, the present invention provides fluorogenic probe compositions comprising compounds of formula (I) or (II) as described herein, and, optionally, a carrier, solvent, an acid, a base, a buffer solution, or a combination thereof.

In another aspect, the present invention provides methods for detecting the presence of and/or determining the level of superoxide in samples. In some embodiments, the methods comprise the steps of a) contacting a compound of formula (I) or (II) as disclosed herein with a sample to form a fluorescent compound; and b) determining fluorescence properties of the fluorescent compound.

In another aspect, the present invention provides methods for detecting the presence of or determining the level of hypochlorous acid or hydroxyl radical in vivo in an organism. In some embodiments, the methods comprise a) administering a compound of formula (I) or (II) as disclosed herein to the organism to form a fluorescent compound; and b) determining fluorescence properties of the fluorescent compound.

In another aspect, the present invention provides high-throughput screening methods for detecting the presence of, or determining the level of, hypochlorous acid or hydroxyl radical in samples. In some embodiments, the methods comprise a) contacting a compound of formula (I) or (II) as disclosed herein with the samples to form one or more fluorescent compounds; and b) determining fluorescence properties of the fluorescent compounds to determine the presence and/or amount of hypochlorous acid or hydroxyl radical in the samples.

In a further aspect, the present invention provides high-throughput methods for screening one or more target compounds that increase or decrease the level of hypochlorous acid or hydroxyl radical. In some embodiments, the methods comprise a) contacting a compound of formula (I) or (II) as disclosed herein with target compounds to form one or more fluorescent compounds; and b) measuring fluorescence properties of the florescent compounds to determine the presence and/or amount of the target compounds.

DETAILED DESCRIPTION

Figure 1A:
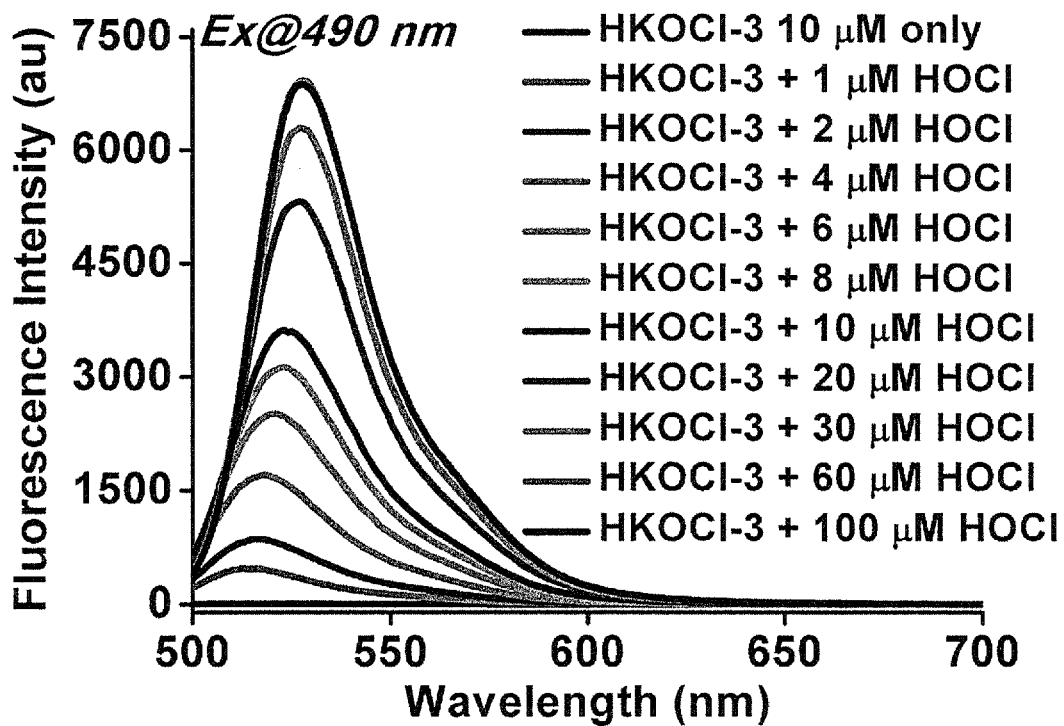
FIG. 1A shows a graph of fluorescence intensity (au) of compound HKOCl-3 for each of HKOCl-3 (10 μM), HKOCl-3+1 μM HOCl, HKOCl-3+2 μM HOCl, HKOCl-3+4 μM HOCl, HKOCl-3+6 μM HOCl, HKOCl-3+8 μM HOCl, HKOCl-3+10 μM HOCl, HKOCl-3+20 μM HOCl, HKOCl-3+30M HOCl, HKOCl-3+60 μM HOCl, and HKOCl-3+100 μM HOCl.

Embodiments of the subject invention provide fluorescent compounds and probes for sensitive and specific detection of HOCl or hydroxyl radical. The disclosed fluorescent probes display superior sensitivity and specificity toward HOCl or hydroxyl radical relative to currently available fluorescent probes for HOCl or hydroxyl radical. Aspects of the invention also include probes that are utilized in drug screening.

In one aspect, the present invention provides compounds of formula (I) or (II):

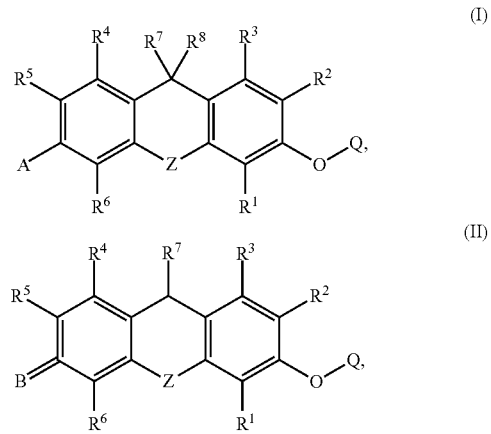

or a tautomer thereof;

wherein each of $R^1$ and $R^2$ is independently F, Cl or H;

wherein each of $R^3$, $R^4$, $R^5$ and $R^6$ is independently H, F, Cl, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphonic acid, phosphate ester, sulfonic acid (—$SO_3H$), sulfonate ester, sulfonamide, —C(=O)—$P^1$ or —C(=O)-M-$P^2$;

wherein each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms; wherein M is alkylene, alkenylene, alkynylene, arylene, aralkylene or alkarylene;

wherein A is $OR^9$ or $NR^{10}R^{11}$;

wherein $R^9$ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;

wherein each of $R^{10}$ and $R^{11}$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl; or wherein $R^{10}$ in combination with $R^{11}$ forms a saturated 5- or 6-membered heterocycle that is a piperidine, a morpholine, a pyrrolidine or a piperazine, each of which is optionally substituted by alkyl, carboxylic acid, a salt of carboxylic acid, or a carboxylic acid ester of an alcohol; or wherein $R^{10}$ in combination with $R^5$, or $R^{11}$ in combination with $R^6$, or both, form a 5- or 6-membered ring that is saturated or unsaturated, or further fused with an aryl or heteroaryl ring, and is optionally substituted by one or more alkyls, carboxylic acids, sulfonic acids (—$SO_3H$), or their salts, ester or amide derivatives;

wherein B is O or $N^+R^{10}R^{11}$;

wherein Z is O, S, $NR^{12}$, $CR^{12}R^{13}$, $SiR^{12}R^{13}$, $GeR^{12}R^{13}$, or $SnR^{12}R^{13}$;

wherein each of $R^{12}$ and $R^{13}$ is independently H, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, hydroxy, thiol, thioalkyl, alkoxy, alkylthio, alkoxyalkyl, aryloxy, arylalkoxy, acyloxy, carbamoyl, trifluoromethyl, phenoxy, benzyloxy, phosphonic acid, phosphate ester, sulfonic acid (—$SO_3H$), sulfonate ester, sulfonamide, carboxylic acid, carboxylic ester, or carboxylic amide; or wherein $R^{12}$ in combination with $R^{13}$ forms a saturated 5- or 6-membered heterocycle that is optionally substituted by alkyl, carboxylic acid, a salt of carboxylic acid, or a carboxylic acid ester of an alcohol;

wherein $R^7$ is H, $CF_3$, CN, a carboxylic acid, a salt of carboxylic acid, or a carboxylic acid ester of an alcohol; or wherein $R^7$ is a saturated or unsaturated alkyl that is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{14}$), sulfonamide (—$SO_2NR^{14}R^{15}$), wherein each of $R^{14}$ and $R^{15}$ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium; or wherein $R^7$ has the formula

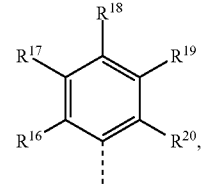

wherein each of $R^{16}$, $R^{17}$, $R^{18}$, $R^{19}$ and $R^{20}$ is independently H, F, Cl, Br, I, CN, nitro, a carboxylic acid, a salt of carboxylic acid, sulfonic acid (—$SO_3H$), sulfonate ester (—$SO_3R^{14}$), sulfonamide (—$SO_2NR^{14}R^{15}$), hydroxy, azide, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{14}$), or sulfonamide (—$SO_2NR^{14}R^{15}$); or wherein $R^{16}$ and $R^{17}$ together, $R^{17}$ and $R^{18}$ together, $R^{18}$ and $R^{19}$ together, or $R^{19}$ and $R^{20}$ together form a part of a 5- or 6-membered cycloalkyl, heterocyclyl, aryl or heteroaryl ring fused with the phenyl ring of formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{14}$), or sulfonamide (—$SO_2NR^{14}R^{15}$);

wherein $R^8$ is H, hydroxy, CN or alkoxy; or wherein $R^7$ in combination with $R^8$ forms a 5-membered spirolactone or spirolactam ring or a 5-membered spirosultam ring; or wherein $R^8$ in combination with $R^{16}$ or $R^{20}$ forms a 5- or 6-membered spirolactone or spirolactam ring or a 5- or 6-membered spirosultone or spirosultam ring that is optionally and independently substituted by H, F or $CH_3$; and wherein Q is a substituted phenyl represented by formula (IV):

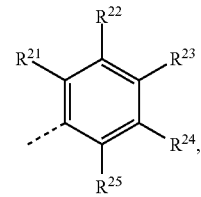

wherein each of $R^{21}$, $R^{22}$, $R^{23}$, $R^{24}$, and $R^{25}$ is independently H, hydroxy, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—SO$_3$H), sulfonate ester (—SO$_3$R$^{14}$), or sulfonamide (—SO$_2$NR$^{15}$R$^{16}$); or wherein R$^{21}$ and R$^{22}$ together, R$^{22}$ and R$^{23}$ together, RR and R$^{24}$ together, or R and R together form a part of a 5- or 6-membered cycloalkyl, heterocyclyl, aryl or heteroaryl ring fused with the phenyl ring of formula (IV) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—SO$_3$H), sulfonate ester (—SO$_3$R$^{14}$), or sulfonamide (—SO$_2$NR$^{14}$R$^{15}$).

In some embodiments, R$^8$ when taken in combination with R$^7$ forms a 5-membered spirolactone or spirolactam ring or a 5-membered spirosultam ring, and R$^8$ is oxygen or substituted nitrogen. In some embodiments, Q of formula (I) or (II) is substituted phenyl represented by formula (IV); and/or R$^2$ is a group that reacts with hypochlorous acid. In further embodiments, R$^{23}$ is OR$^{26}$, CH$_2$CH$_2$COR$^{27}$, or NR$^{28}$R$^{29}$, wherein R$^{26}$ is hydrogen or a group selected from alkyl, alkoxyalkyl, alkanoyl, or polyether; wherein R$^{27}$ is an electron-withdrawing group selected from CF$_3$, halogen-substituted lower alkyl, or (C=O)—O—W$_1$, wherein W$_1$ is a group selected from alkyl, alkenyl, alkynyl, cycloalkyl, cycloalkenyl, cycloalkynyl, aryl, alkaryl or arylalkyl; wherein R$^{28}$ and R$^{29}$ are independently hydrogen or a group selected from hydrogen or a group selected from alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether.

In one embodiment, R$^7$ is formula (III).

In some embodiments, the compounds of the present invention have a structure of formula (II), or a tautomer thereof, and wherein B is O, Z is O, and R$^7$ is formula (III). Furthermore, at least one of R$^{16}$, R$^{17}$, R$^{18}$, and R$^{19}$ is a carboxyl group; R$^{20}$ is H, CH$_3$, OMe, or COOH; and/or the R$^7$ group of formula (III) comprises one or more carboxyl groups, wherein at least one carboxyl group is further conjugated with an iminodialkylcarboxylate having a structure of (HN((CH$_2$)$_n$COOH)$_2$, wherein n is an integer from 1 to 20. In one specific embodiment, the compounds of the present invention have a structure of (V) or its tautomer (VI)

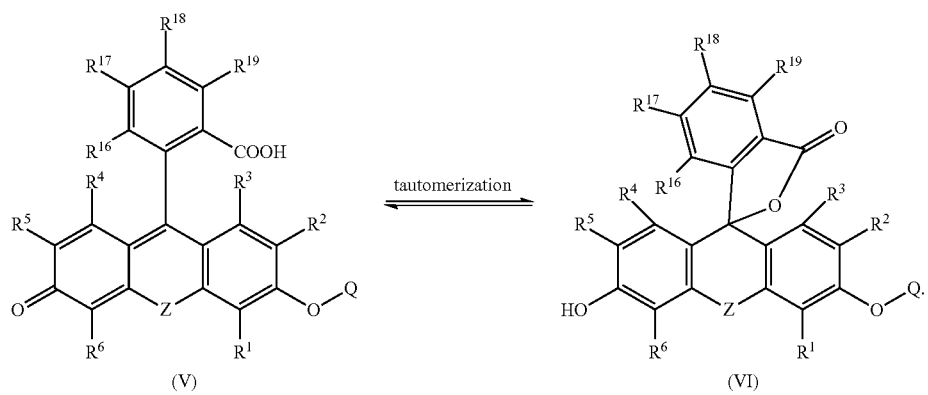

(V)    (VI)

The COOH group of the compounds can be esterified with a methyl, ethyl, or acetoxymethyl (AM) group. In additional embodiments, the phenolic group of the compounds is acylated with acetyl, propionyl, or butyryl groups, or is protected with acetoxymethyl (AM) groups.

In further specific embodiments, the compounds of the present invention have one of formulae 1-20:

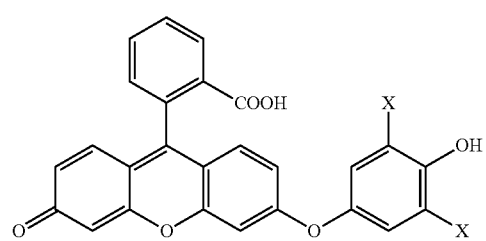

1

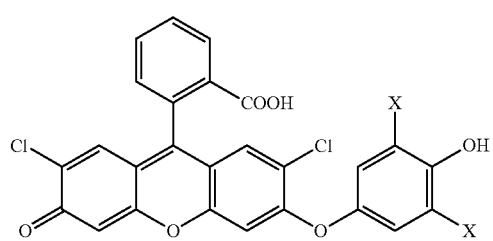

2

-continued
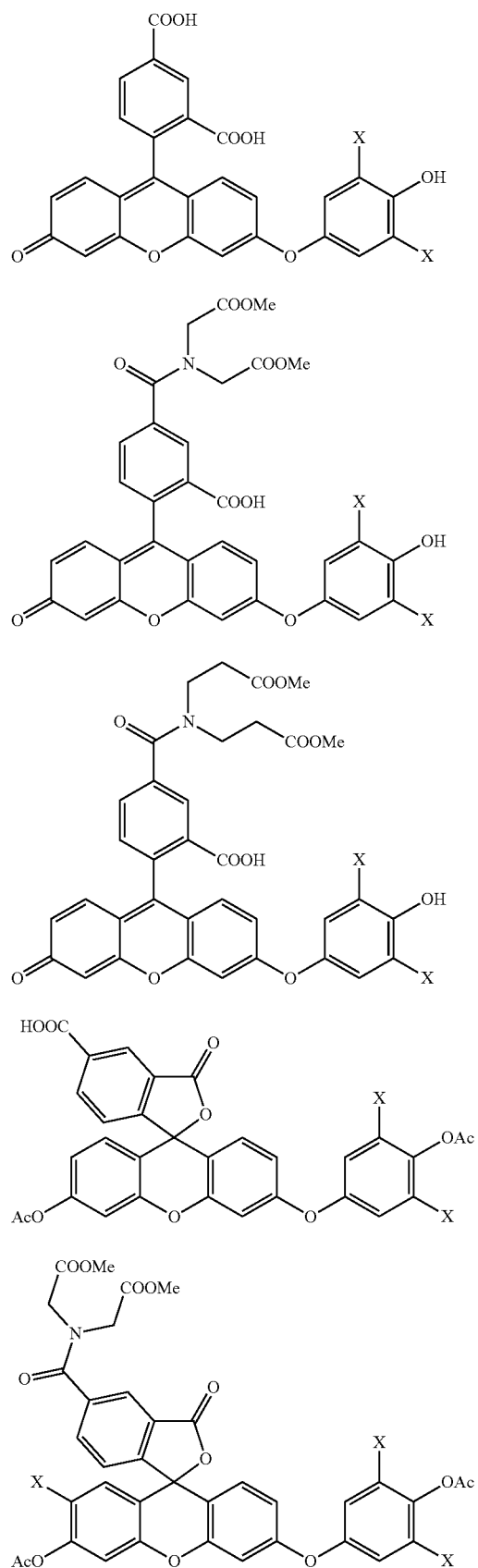
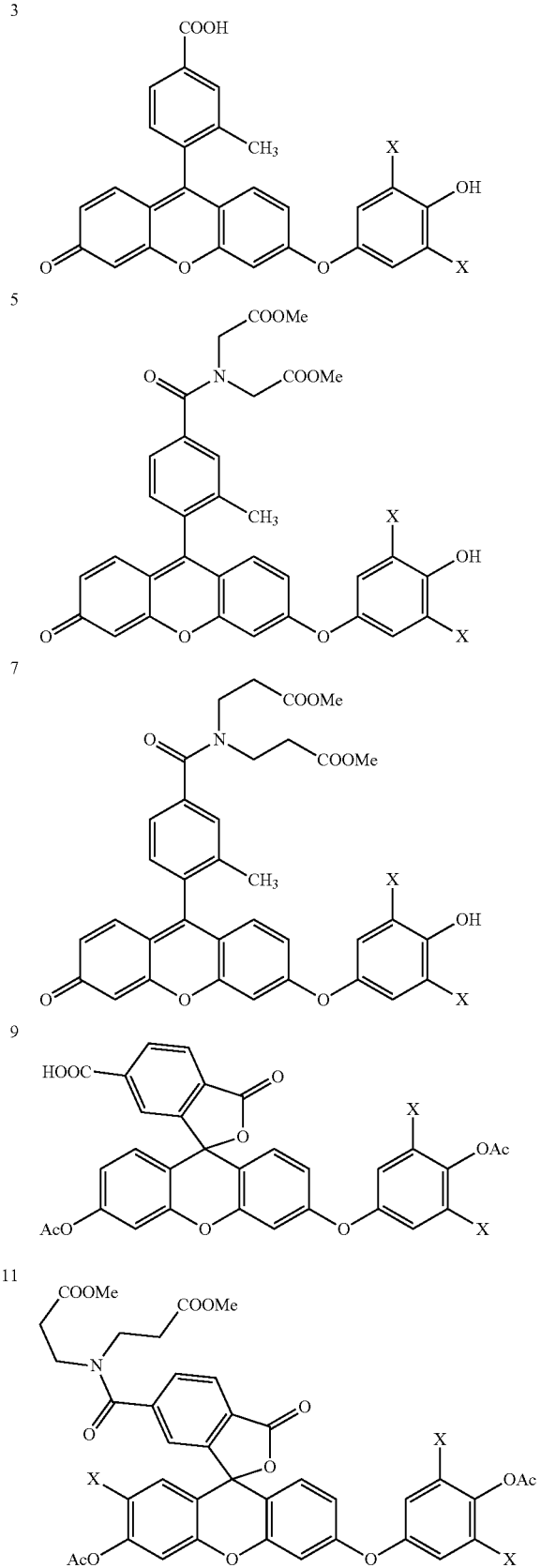

-continued
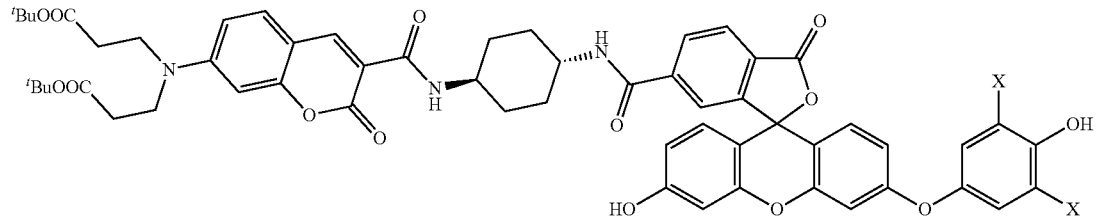
13
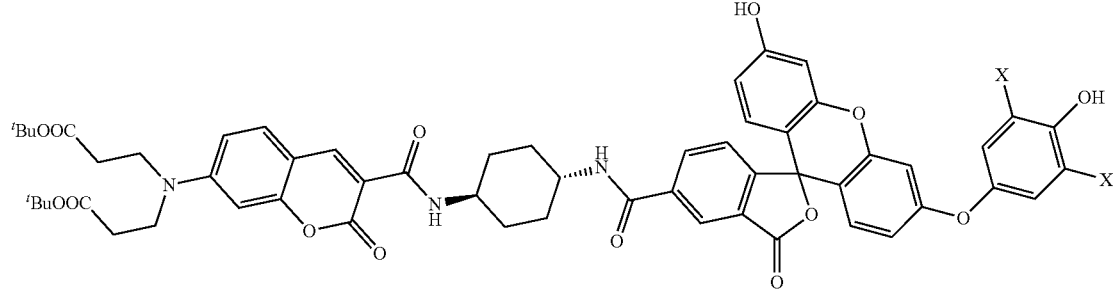
14
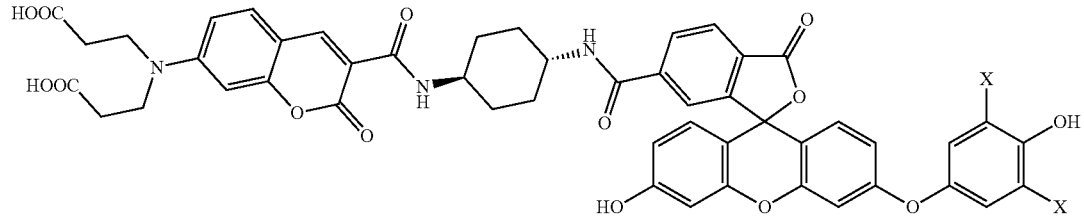
15
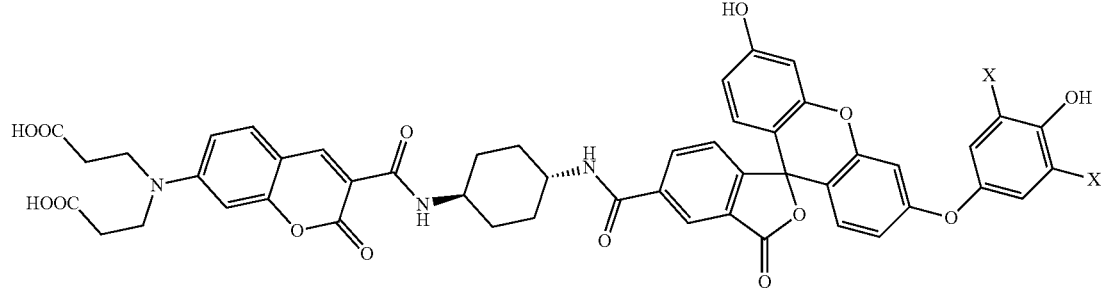
16
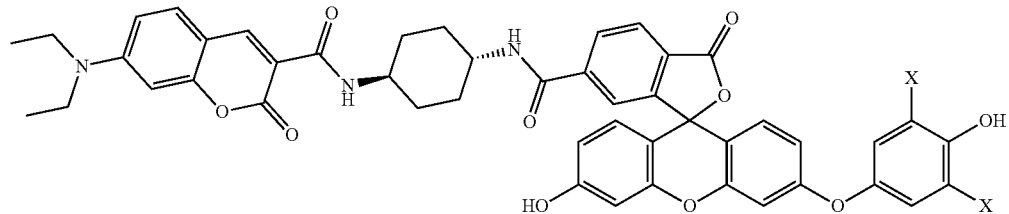
17
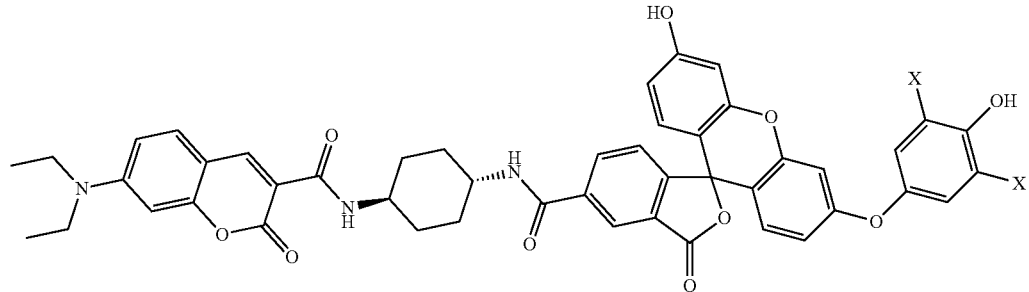
18

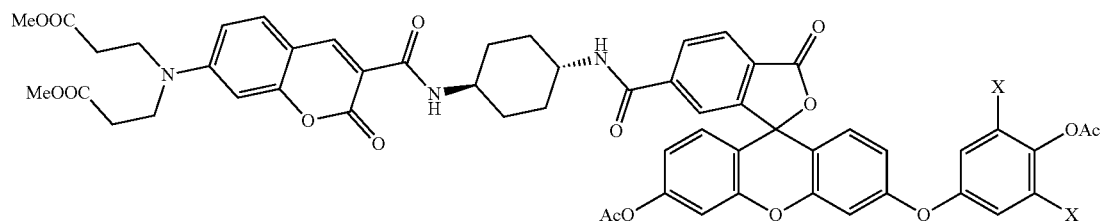

19

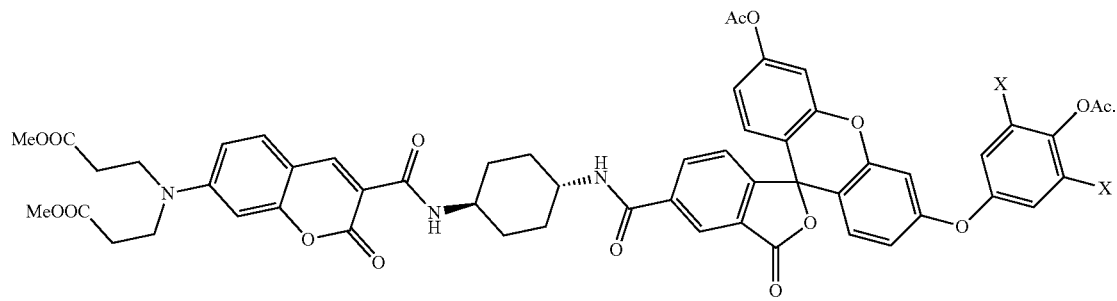

20

X = F, Cl, Br, or I

In another embodiment, the compounds of the present invention have a structure of formula (II), or a tautomer thereof, and wherein B is $N^+R^{10}R^{11}$, Z is O, and $R^7$ is formula (II). In specific embodiments, the compounds have a structure of (VII) or its tautomer (VIII)

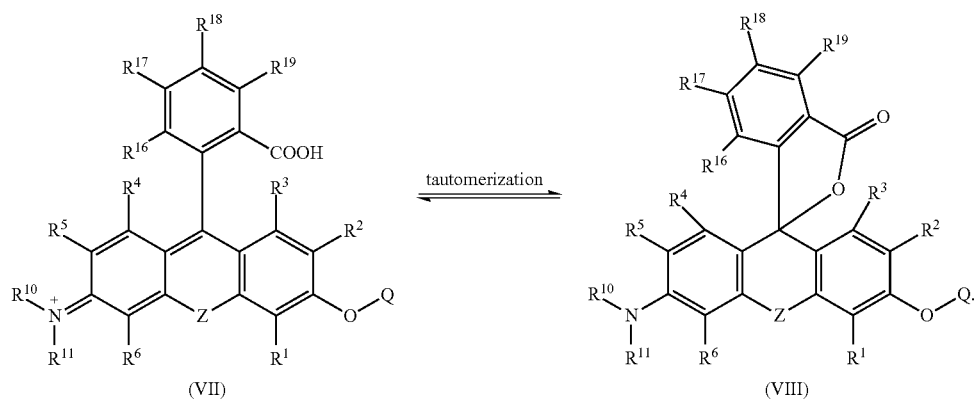

COOH group can be esterified with a methyl, ethyl, or acetoxymethyl (AM) group. Furthermore, at least one of $R^{16}$-$R^{19}$ is an alkylating group. The alkylating group can have a formula of $CR^{30}R^{31}X$, wherein $R^{30}$ and $R^{31}$ are independently H and $CH_3$, and X is F, Cl, Br, or I.

In another embodiment, the compounds of the present invention have a structure of formula (IX) or (X)

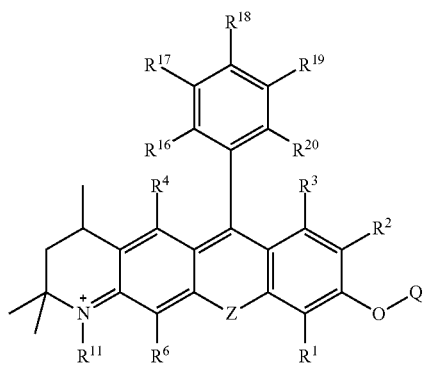

(IX)

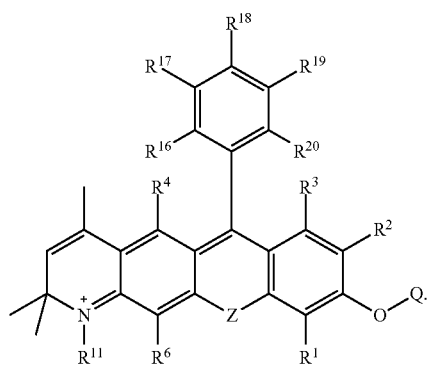

(X)

In specific embodiments, $R^{11}$ in formula (IX) or (X) is a $C_{1-10}$ alkyl or alkene. In further specific embodiments, $R^{11}$ in formula (IX) or (X) is a $C_{1-10}$ alkyl or alkene substituted with a carboxyl group at the terminal position. For example, $R^{11}$ can be ethyl, carboxylmethyl, carboxylethyl, or carboxylpropyl.

In some embodiments, the compounds of the present invention have one of formulae 21-36:

21

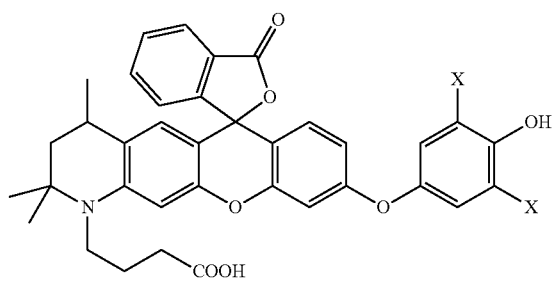

22

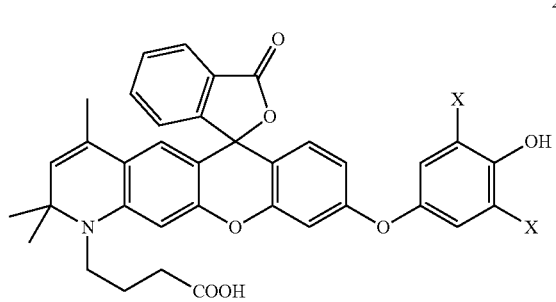

23

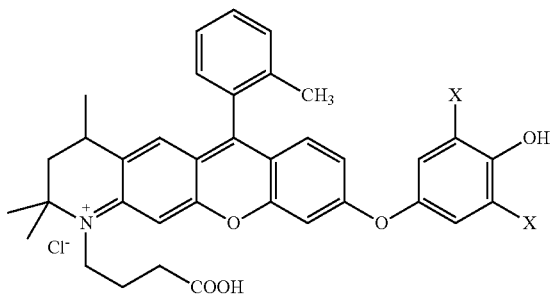

24

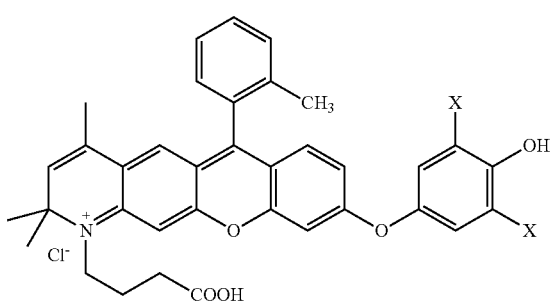

25

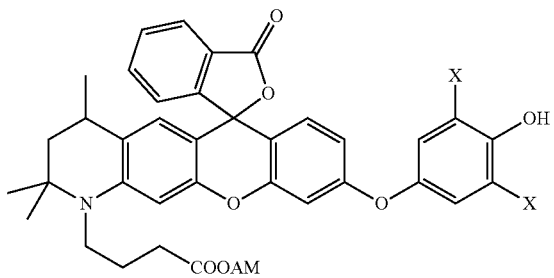

26

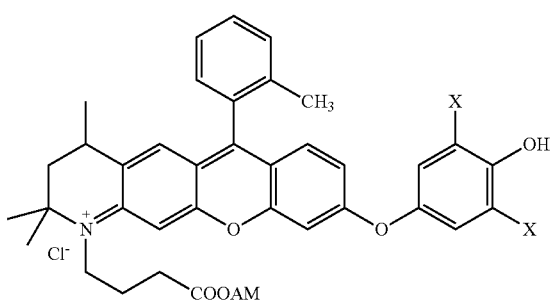

27

28
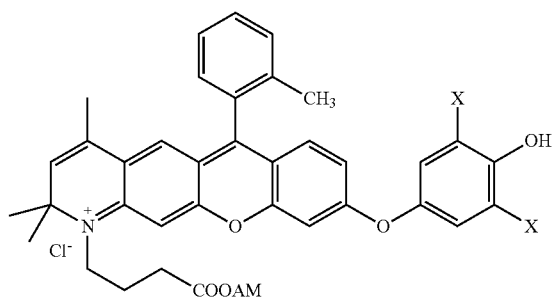

29
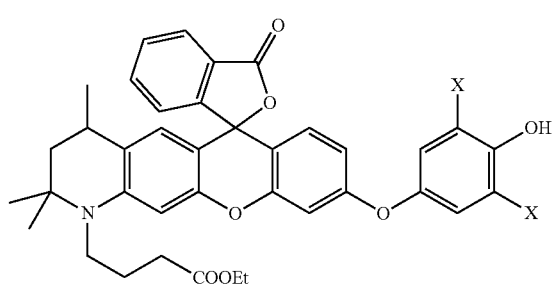

30
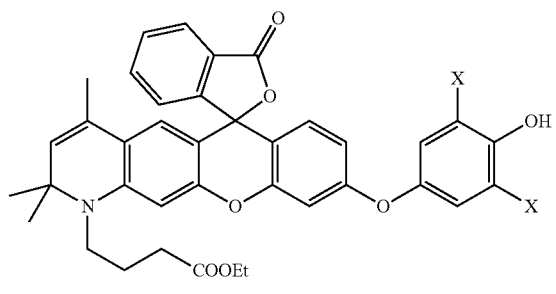

31
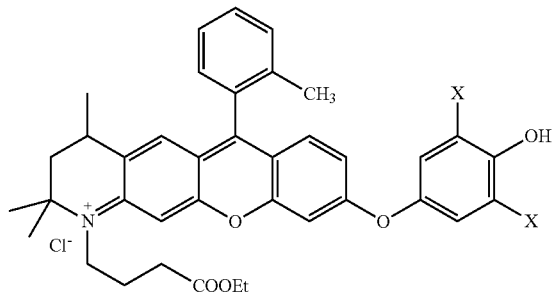

32
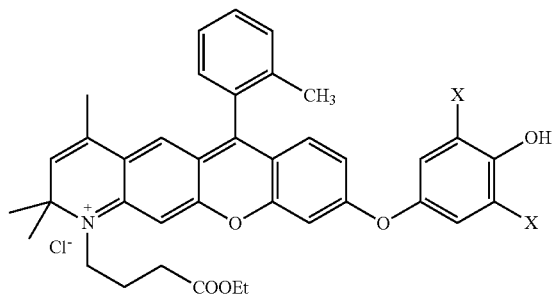

33
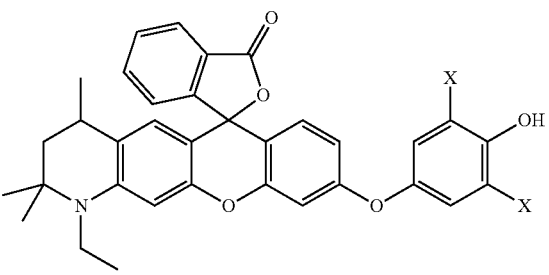

34
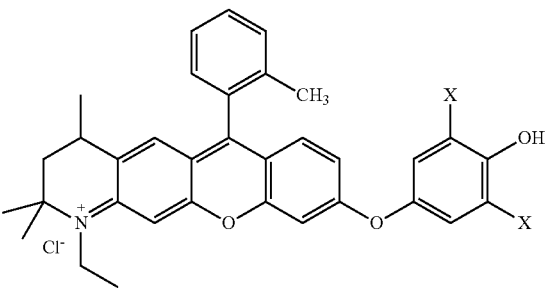

35
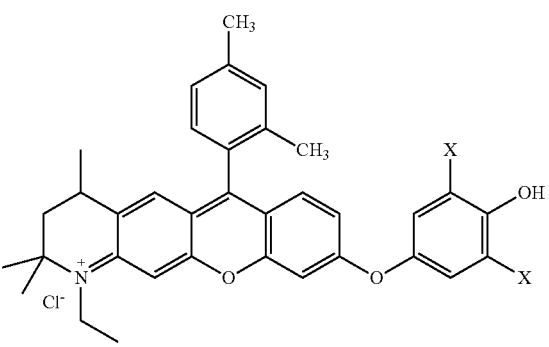

36
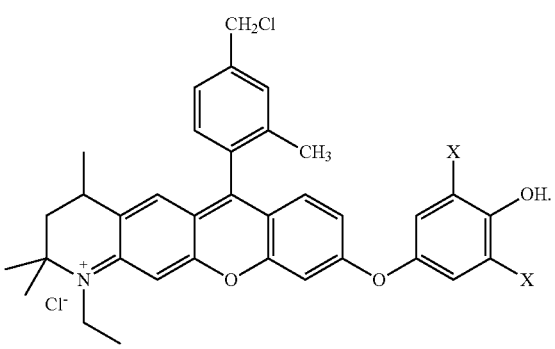

AM = CH₂OCOCH₃
X = F, Cl, Br, or I

In some embodiments, the compounds of the present invention have a structure of formula (II), and wherein B is O, Z is $YR^{12}R^{13}$, wherein Y is Si, Ge, or Sn, and $R^7$ is formula (III). In specific embodiments, $R^{12}$ and $R^{13}$ are independently $CH_3$, or phenyl. In further specific embodiments, $R^{20}$ is COOH, and the compound has a structure of (XI) or its tautomer (XII)

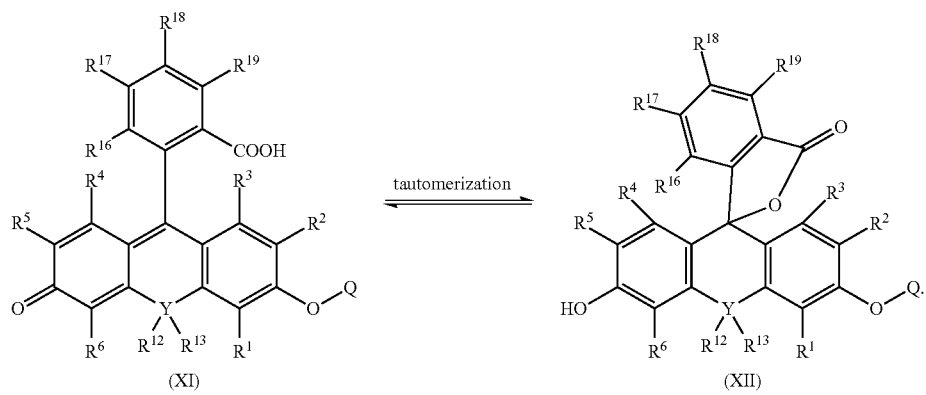

COOH group can be esterified with a methyl, ethyl, or acetoxymethyl (AM) group. Also, the phenolic group can be acylated with acetyl, propionyl, or butyryl groups, or is protected with acetoxymethyl (AM) groups.

In some embodiments, the compounds of the present invention have one of formulae 37-39:

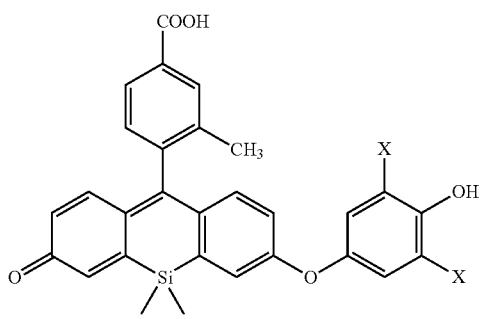

37

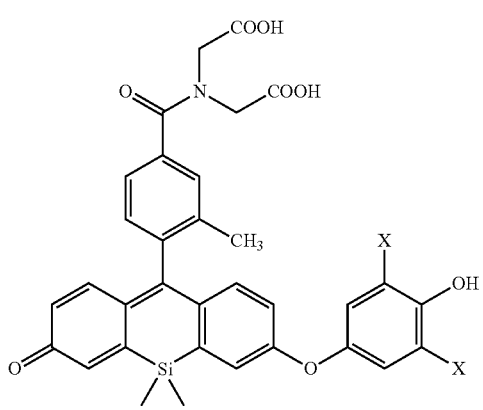

38

-continued

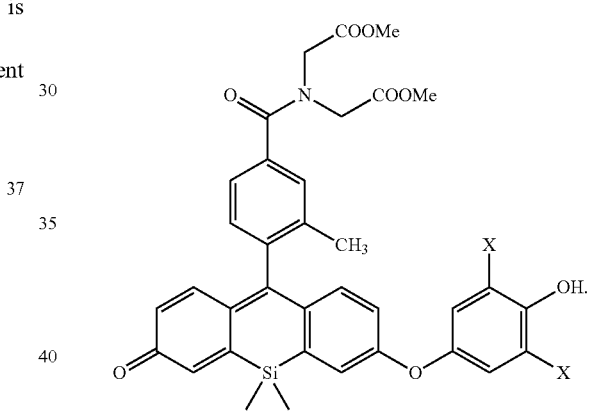

39

X = F, Cl, Br, or I

In some embodiments, the compounds of the present invention have a structure of formula (II), and wherein B is $NR^+R^{10}R^{11}$, Z is $YR^{12}R^{13}$, wherein Y is Si, Ge, or Sn, and wherein $R^7$ is formula (III). In specific embodiments, $R^{20}$ is COOH, and wherein the compound has a structure of (XIII) or its tautomer (XIV):

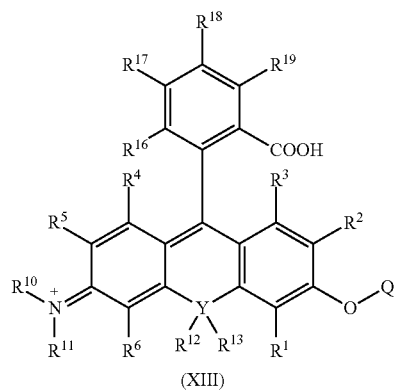

(XIII)

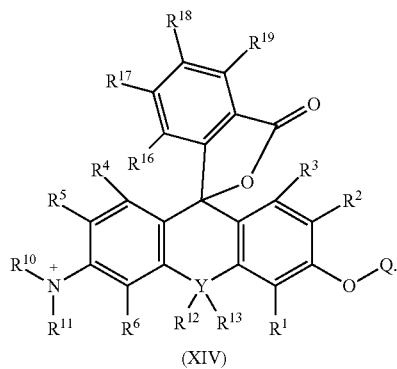

(XIV)

specific embodiments, $R^{10}$ in combination with $R^5$, or $R^{11}$ in combination with $R^6$, or both, form a 5- or 6-membered ring that is saturated or unsaturated, or can further be fused with an aryl or heteroaryl ring, and can optionally be substituted by one or more alkyls, carboxylic acids, sulfonic acids (—SO₃H), or their salts, ester or amide derivatives. The COOH group can be esterified with a methyl, ethyl, or acetoxymethyl (AM) group and/or the phenolic group can be acylated with acetyl, propionyl, or butyryl groups, or is protected with acetoxymethyl (AM) groups. In specific embodiments, the compounds of the present invention have a formula of (XV) or (XVI):

In additional specific embodiments, the compounds of the present invention have one of the formulae 40-45:

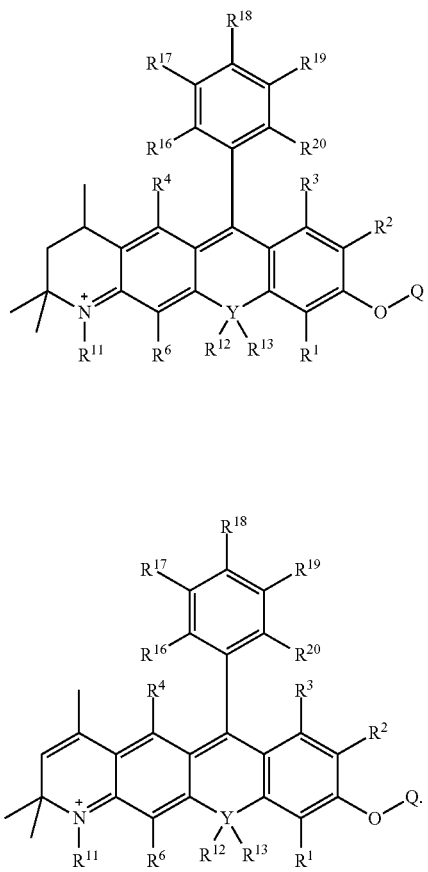

(XV)

(XVI)

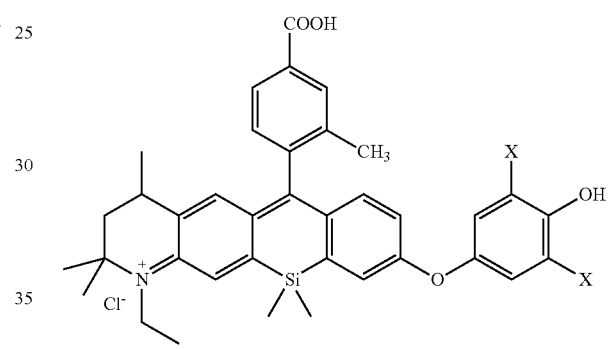

40

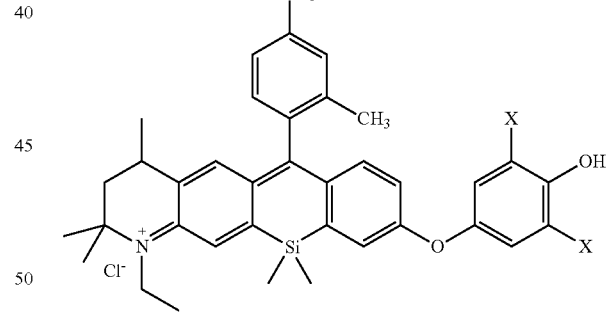

41

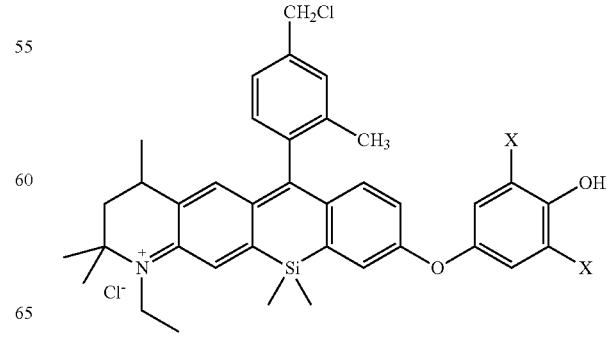

42

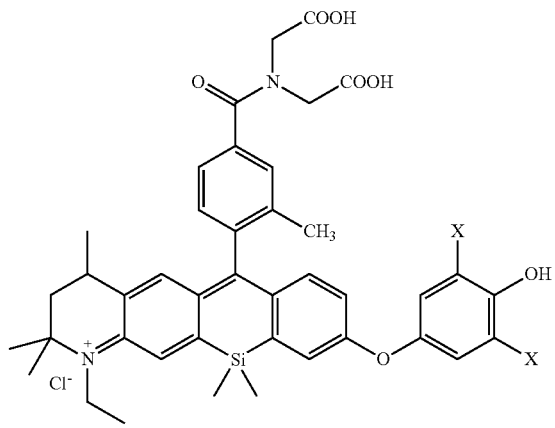

43

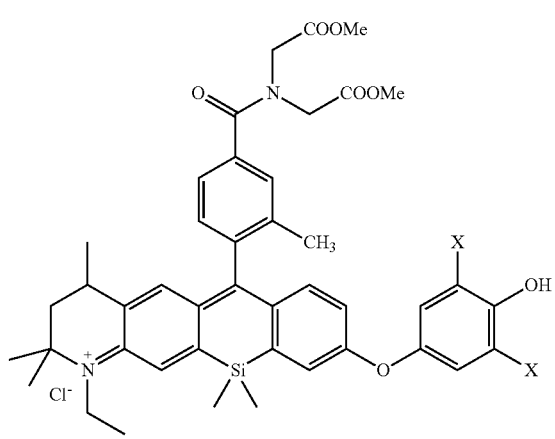

44

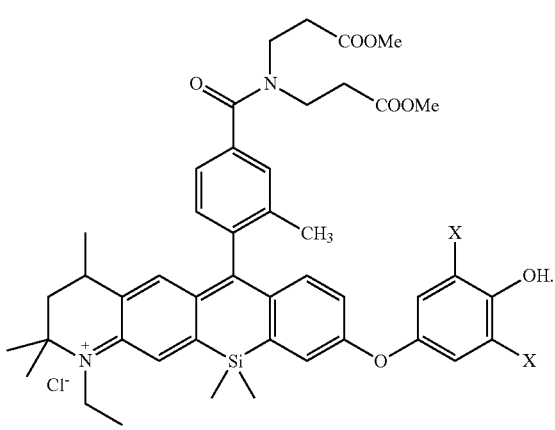

45

X = F, Cl, Br, or I

In some embodiments of the present invention, the compounds comprise one or more free carboxyl groups, wherein at least one of the carboxyl groups is conjugated with a positively charged mitochondria-targeted triphenylphosphonium moiety or lysosome-targeted morpholine moiety through an amide bond linkage. For example, the linkage between the compound and the triphenylphosphonium moiety can have the following formula (XVII) or (XVIII):

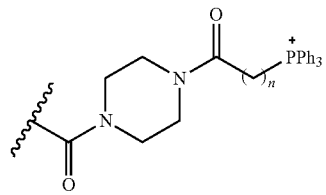

(XVII)

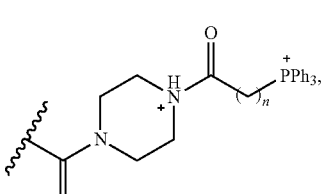

(XVIII)

wherein n=1, 2, 3, 4, 5, 6, 7, 8, 9, or 10. In specific embodiments, the compounds of the present invention have one of the formulae 46-51:

46

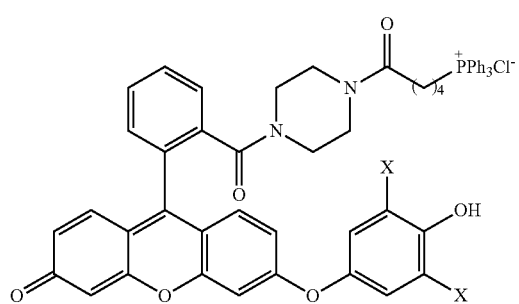

47

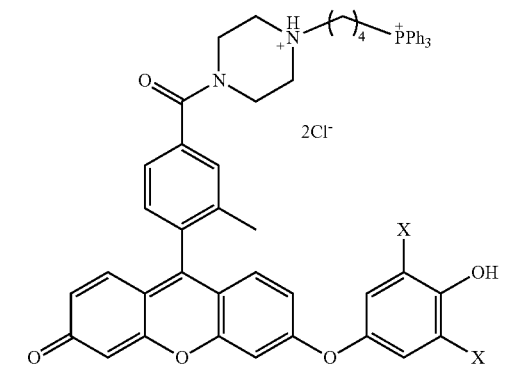

48

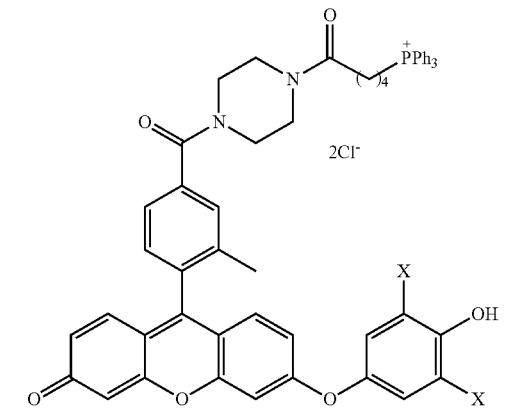

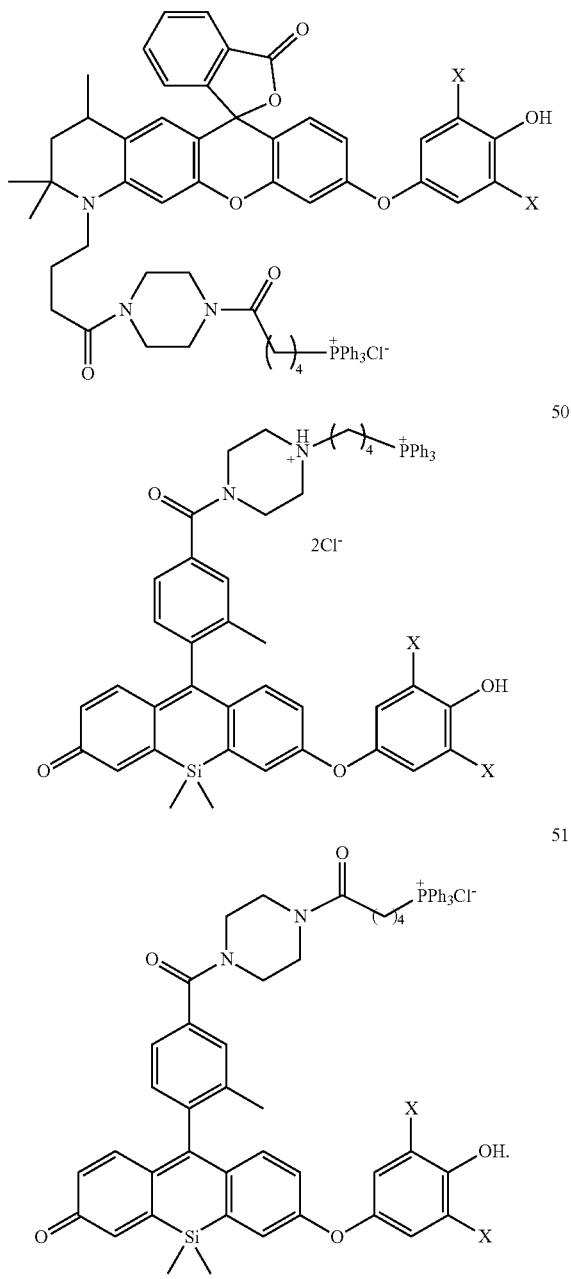
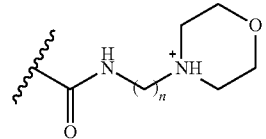
X = F, Cl, Br, or I
In specific embodiments, the linkage between the compound and the morpholine or N,N-disubstituted amine moiety has the following formula (XIV) or (XV):
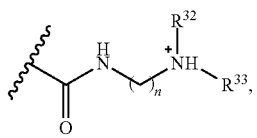
wherein n=1, 2, 3, 4, 5, 6, 7, 8, 9, or 10; $R^{32}$ or $R^{33}$ in formula (XV) is independently is a $C_{1-10}$ alkyl or alkene.
In some embodiments, the compounds of the present invention have one of the formulae 52-61:
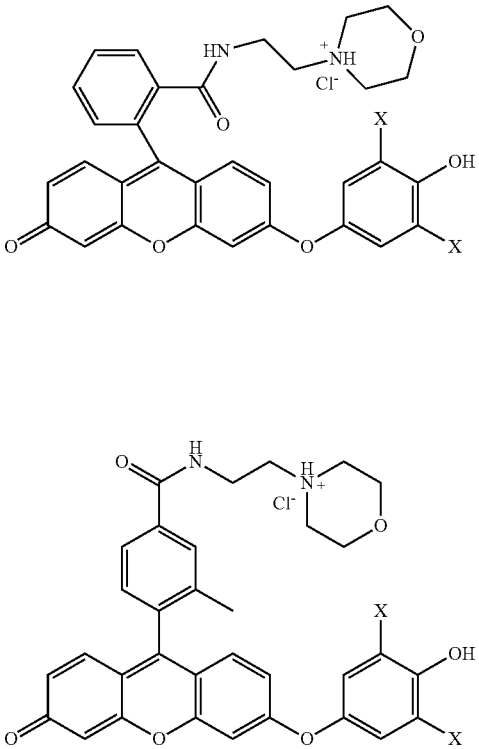
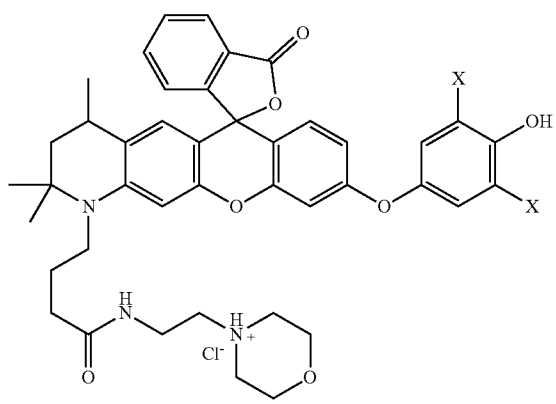

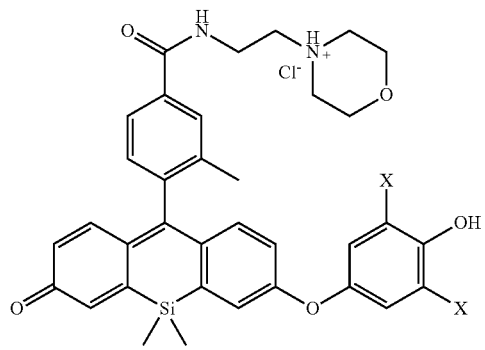

55

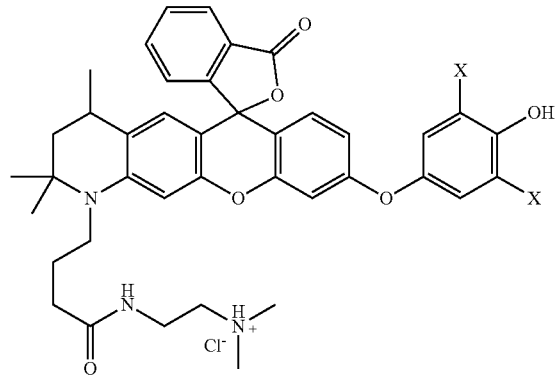

59

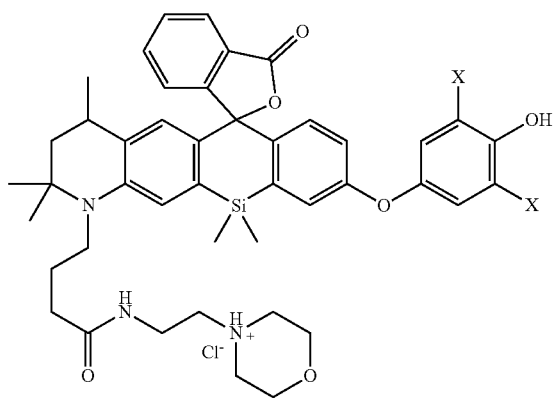

56

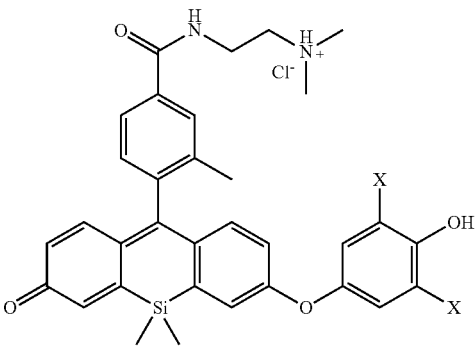

60

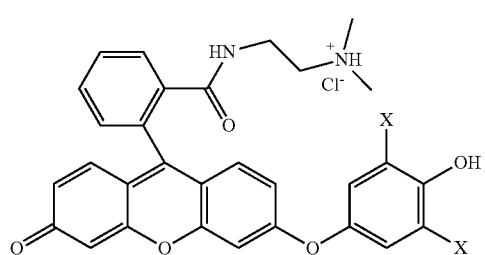

57

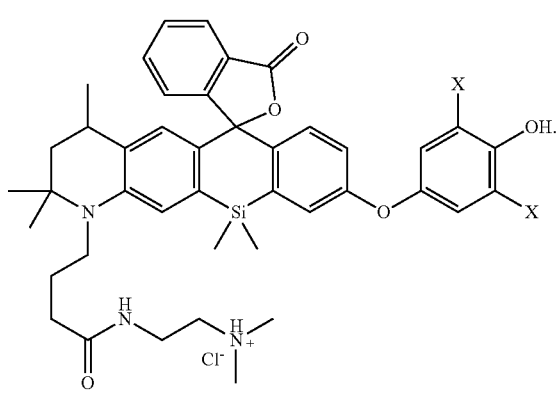

61

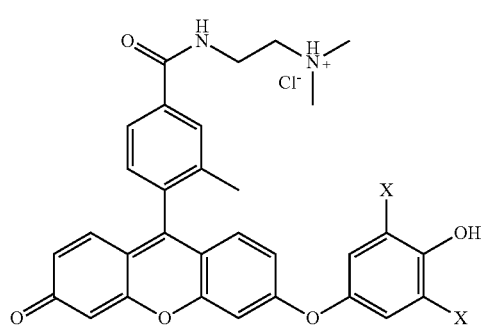

58

X = F, Cl, Br, or I

In one aspect, the present invention provides fluorogenic probe compositions comprising compounds of formula (I) or (II) as described herein, and, optionally, a carrier, solvent, an acid, a base, a buffer solution, or a combination thereof.

In another aspect, the present invention provides methods for detecting the presence of and/or determining the level of superoxide in samples. In some embodiments, the methods comprise the steps of a) contacting a compound of formula (I) or (II) as disclosed herein with a sample to form a fluorescent compound; and b) determining fluorescence properties of the fluorescent compound. In some embodiments, the sample is a chemical sample or biological sample. In further specific embodiments, the sample is a biological sample comprising a microorganism, or a cell or tissue.

In another aspect, the present invention provides methods for detecting the presence of or determining the level of hypochlorous acid or hydroxyl radical in vivo in an organism. In some embodiments, the methods comprise a) administering a compound of formula (I) or (II) as disclosed herein to the organism to form a fluorescent compound; and b) determining fluorescence properties of the fluorescent compound.

In another aspect, the present invention provides high-throughput screening methods for detecting the presence of, or determining the level of, hypochlorous acid or hydroxyl radical in samples. In some embodiments, the methods comprise a) contacting a compound of formula (I) or (II) as disclosed herein with the samples to form one or more fluorescent compounds; and b) determining fluorescence properties of the fluorescent compounds to determine the presence and/or amount of hypochlorous acid or hydroxyl radical in the samples.

In a further aspect, the present invention provides high-throughput methods for screening one or more target compounds that increase or decrease the level of hypochlorous acid or hydroxyl radical. In some embodiments, the methods comprise a) contacting a compound of formula (I) or (II) as disclosed herein with target compounds to form one or more fluorescent compounds; and b) measuring fluorescence properties of the florescent compounds to determine the presence and/or amount of the target compounds.

In embodiments described herein, the fluorescence properties are measured with methods disclosed herein or any method known to a person skilled in the art. Suitable samples include, but are not limited to, chemical (non-biological) samples and biological samples. Suitable biological samples include, but are not limited to, samples containing unicellular or unicellular organisms, microorganisms, cells, tissues, and organs of living organisms, preferably, of animals including humans.

The probes of the present invention feature an ultra-efficient and novel mechanism for HOCl or hydroxyl radical detection as, for example, they contain substituted diaryle-ther groups as reacting sites, thus escalating the sensitivity toward HOCl or hydroxyl radical and avoiding the interference from cellular ROS/RNS. The probes of the present invention exhibit sensitivity and selectivity toward HOCl or hydroxyl radical over a wide range of reactive oxygen and nitrogen species (ROS/RNS) found in cells. The performance of those probes in HOCl or hydroxyl radical imaging is highly robust in multiple cellular models, including, for example, inflammation and mitochondrial respiratory inhibition. The probes therefore provide discovery tools for dissecting the roles of HOCl or hydroxyl radical in health and disease.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

Following are examples that illustrate embodiments for practicing the invention. The detailed disclosure falls within the scope of, and serve to exemplify, the synthetic schemes or procedures disclosed herein which form part of this disclosure. These examples, figures and schemes are presented for illustrative purposes only and are not intended to limit the scope of this disclosure. All percentages are by weight and all solvent mixture proportions are by volume unless otherwise noted.

EXAMPLES

Example 1—Synthesis of Green Fluorogenic Compound HKOCl-3, HJ-3-279 and HJ-3-286

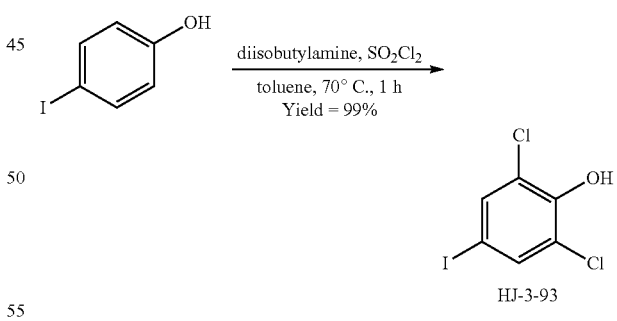

To a solution of 4-iodophenol (5.50 g, 25 mmol) in dry toluene (90 mL) at room temperature was added diisobutylamine (35 µL, 0.2 mmol) under argon atmosphere. The resulting solution was warmed up to 70° C., then $SO_2Cl_2$ (6.05 mL, 75 mmol) was slowly added in via a syringe (gas escapes to a balloon). The reaction mixture was stirred at 70° C. for 1 h and allowed to cool to room temperature. Then the reaction mixture was diluted with $Et_2O$ and washed with saturated $NaHCO_3$ solution and brine. The organic layer was dried over anhydrous magnesium sulfate and concentrated in vacuo. The target compound HJ-3-93 [34074-22-1] was isolated as a white solid by flash chromatography on silica gel by using EtOAc:Hexane (1:99) as an eluent. Yield: 7.20 g (99%). $^1$H NMR (400 MHz, CDCl$_3$) δ 7.53 (s, 2H), 5.81 (brs, 1H); $^{13}$C NMR (100 MHz, CDCl$_3$) δ 148.0, 136.4, 122.1, 80.5.

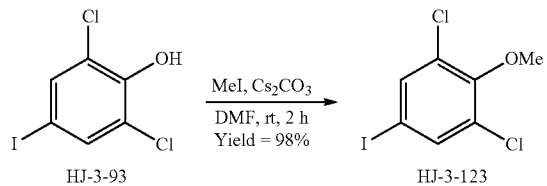 [SMILES: Oc1c(Cl)cc(I)cc1Cl ; COc1c(Cl)cc(I)cc1Cl]

To a mixture of HJ-3-93 (1.66 g, 5.75 mmol) and Cs$_2$CO$_3$ (2.25 g, 6.90 mmol) in anhydrous DMF (20 mL) at room temperature was added iodomethane (0.43 mL, 6.90 mmol) slowly under argon atmosphere. The resulting mixture was stirred at room temperature for 2 h. Then the reaction mixture was diluted with ethyl acetate and washed with 1 N HCl, water and brine. The organic layer was dried over anhydrous magnesium sulfate and concentrated in vacuo. The target compound HJ-3-123 [71742-42-2] was isolated by flash chromatography as a white solid on silica gel, by using Et$_2$O:Hexane (1:99) as an eluent. Yield: 1.71 g (98%). $^1$H NMR (400 MHz, CDCl$_3$) δ 7.57 (s, 2H), 3.86 (s, 3H); $^{13}$C NMR (100 MHz, CDCl$_3$) δ 152.4, 137.1, 130.3, 86.3, 60.7.

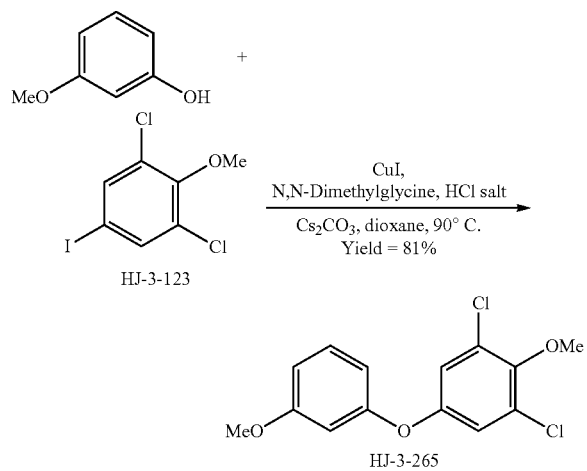

A mixture of HJ-3-123 (470 mg, 1.55 mmol), 3-methoxyphenol (289 mg, 2.33 mmol), CuI (30 mg, 0.155 mmol), N,N-dimethylglycine hydrochloride (65 mg, 0.465 mmol), Cs$_2$CO$_3$ (1.01 g, 3.10 mmol) and anhydrous 1,4-dioxane (10 mL) in a sealed flask was heated to 90° C. and stirred for 24 h under argon atmosphere. The reaction mixture was allowed to cool to room temperature, diluted with ethyl acetate and washed with 1 N HCl, water and brine. The organic layer was dried over anhydrous magnesium sulfate and concentrated in vacuo. The target compound HJ-3-265 was isolated as a colorless oil by flash chromatography on silica gel, by using EtOAc:Hexane (1:19) as an eluent. Yield: 376 mg (81%). $^1$H NMR (300 MHz, CDCl$_3$) δ 7.25 (t, J=8.1 Hz, 1H), 6.95 (s, 2H), 6.74-6.68 (m, 1H), 6.60-6.53 (m, 2H), 3.88 (s, 3H), 3.79 (s, 3H); $^{13}$C NMR (75 MHz, CDCl$_3$) 161.2, 157.4, 153.5, 148.3, 130.6, 129.9, 119.1, 111.4, 110.0, 105.6, 61.0, 55.6; LRMS (EI, 20 eV) m/z (%) 298 (M$^+$; 100), 283 (92); HRMS (EI): calcd for C$_{14}$H$_{12}$O$_3$Cl$_2$ (M$^+$): 298.0163. found: 298.0159.

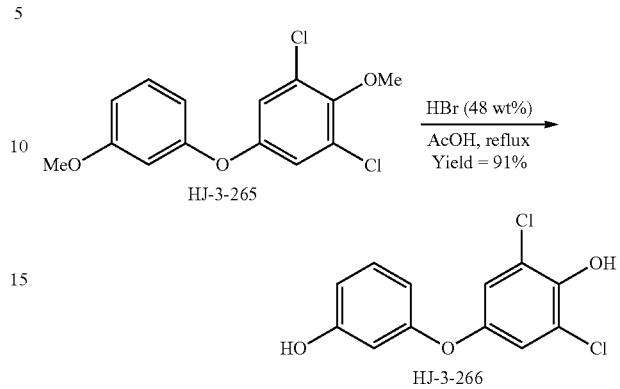

A solution of HJ-3-265 (218 mg, 0.73 mmol) in acetic acid (7 mL) and HBr (48 wt. % in H$_2$O, 7 mL) was heated to reflux and stirred for 12 h under argon atmosphere. The reaction mixture was allowed to cool to room temperature, diluted with ethyl acetate and washed with 1 N HCl, water and brine. The organic layer was dried over anhydrous magnesium sulfate and concentrated in vacuo. The target compound HJ-3-266 was isolated as a white sticky solid by flash chromatography on silica gel, by using EtOAc:Hexane (3:17) as an eluent. Yield: 180 mg (91%). $^1$H NMR (400 MHz, CDCl$_3$) δ 6.95 (t, J=8.1 Hz, 1H), 6.78 (s, 2H), 6.43 (dd, J=8.1, 1.5 Hz, 1H), 6.31 (t, J=1.9 Hz, 1H), 6.28 (d, J=8.1 Hz, 1H), 4.50 (brs, 2H); $^{13}$C NMR (100 MHz, CDCl$_3$) δ 158.0, 157.8, 149.2, 144.9, 130.1, 122.2, 119.1, 110.4, 109.3, 105.4; LRMS (EI, 20 eV) m/z (%) 272 (66), 270 (M$^+$; 100); HRMS (EI): calcd for C$_{12}$H$_8$O$_3$Cl$_2$ (M$^+$): 269.9850. found: 269.9845.

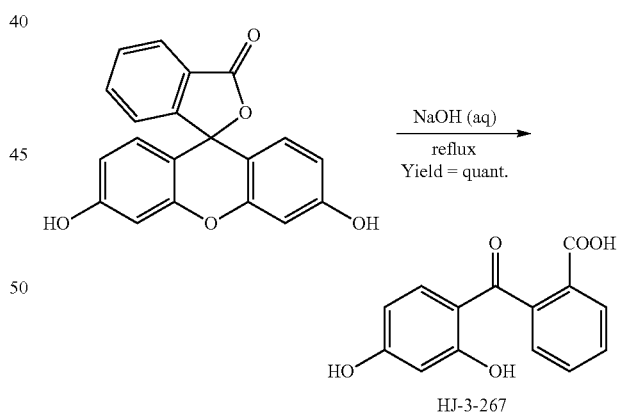

A solution of fluorescein (3.32 g, 10 mmol) in NaOH aqueous solution (12.5 M, 125 mL) was heated to reflux and stirred for 1 h under argon atmosphere. The reaction mixture was allowed to cool to room temperature, and carefully acidified with conc. HCl at 0° C. until large amount of precipitate was formed. Then the target compound HJ-3-267 [2513-33-9] was filtered, washed with water and dried in air for 24 h to obtain a brown solid. Yield: 2.58 g (quant.). $^1$H NMR (300 MHz, CD$_3$OD) δ8.08 (d, J=7.6 Hz, 1H), 7.64 (t, J=7.4 Hz, 1H), 7.57 (t, J=7.5 Hz, 1H), 7.32 (d, J=7.4 Hz, 1H), 6.93 (d, J=8.8 Hz, 1H), 6.35 (d, J=2.2 Hz, 1H), 6.22

(dd, J=8.8, 2.3 Hz, 1H); $^{13}$C NMR (125 MHz, CD$_3$OD) δ 202.3, 168.2, 165.7, 141.2, 135.7, 132.9, 131.2, 130.1, 129.8, 1278.0, 114.3, 108.8, 103.3.

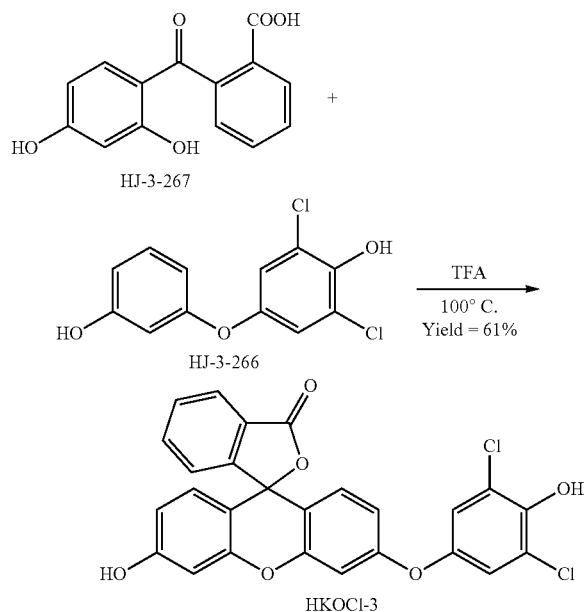

A solution of HJ-3-266 (17 mg, 0.066 mmol) and HJ-3-267 (18 mg, 0.066 mmol) in TFA (2 mL) in a sealed flask was heated to 100° C. and stirred for 12 h under argon atmosphere. The reaction mixture was allowed to cool to room temperature and azeotroped with toluene for 3 times. The target compound HKOCl-3 was isolated as a light yellow sticky solid by flash chromatography on silica gel by using EtOAc:Hexane (3:7) as an eluent. Yield: 20 mg (61%). $^1$H NMR (600 MHz, CDCl$_3$) δ 8.03 (d, J=7.3 Hz, 1H), 7.70 (t, J=7.4 Hz, 1H), 7.63 (t, J=7.4 Hz, 1H), 7.18 (d, J=7.6 Hz, 1H), 7.03 (s, 1H), 7.02 (s, 1H), 6.78-6.69 (m, 3H), 6.64 (dd, J=8.7, 2.3 Hz, 1H), 6.57 (d, J=8.7 Hz, 1H), 6.53 (dd, J=8.7 Hz, 1H); $^{13}$C NMR (75 MHz, CDCl$_3$) δ 170.4, 159.3, 158.4, 153.1, 152.6, 152.4, 148.6, 145.3, 135.5, 130.1, 129.8, 129.4, 126.7, 125.3, 124.2, 121.8, 120.5, 113.9, 112.8, 110.7, 105.6, 103.3, 83.9; LRMS (EI, 20 eV) m/z (%) 492 (M$^+$; 1), 271 (100); HRMS (EI): calcd for C$_{26}$H$_{14}$O$_6$Cl$_2$ (M$^+$): 492.0167. found: 492.0155.

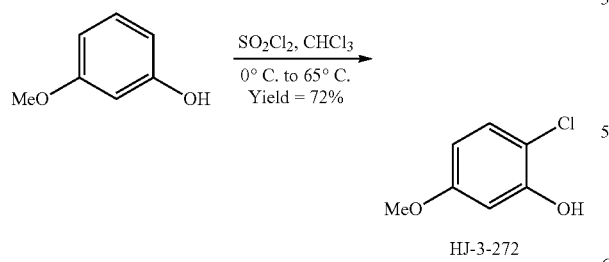

To a solution of 3-methoxyphenol (5.0 g, 40.3 mmol) in CHCl$_3$ (50 mL) at 0° C. was added SO$_2$Cl$_2$ (3.9 mL, 48.3 mmol) slowly. The resulting solution was stirred for 30 min under argon atmosphere, then heated to 65° C. and stirred for 3 h. The reaction mixture was allowed to cool down to room temperature, poured into ice cold water (100 mL) and extracted with CHCl$_3$, washed with saturated NaHCO$_3$ solution and brine. The organic layer was dried over anhydrous magnesium sulfate and concentrated in vacuo. The target compound HJ-3-272 [18113-03-6] was isolated as a colorless oil by flash chromatography on silica gel using EtOAc:Hexane (1:9) as an eluent. Yield: 4.57 g (72%). $^1$H NMR (300 MHz, CDCl$_3$) δ 7.16 (d, J=8.9 Hz, 1H), 6.61 (d, J=2.9 Hz, 1H), 6.44 (dd, J=8.9, 2.9 Hz, 1H), 6.06 (d, J=1.8 Hz, 1H), 3.73 (s, 3H); $^{13}$C NMR (75 MHz, CDCl$_3$) δ 159.6, 152.1, 129.2, 111.6, 107.6, 102.1, 55.4.

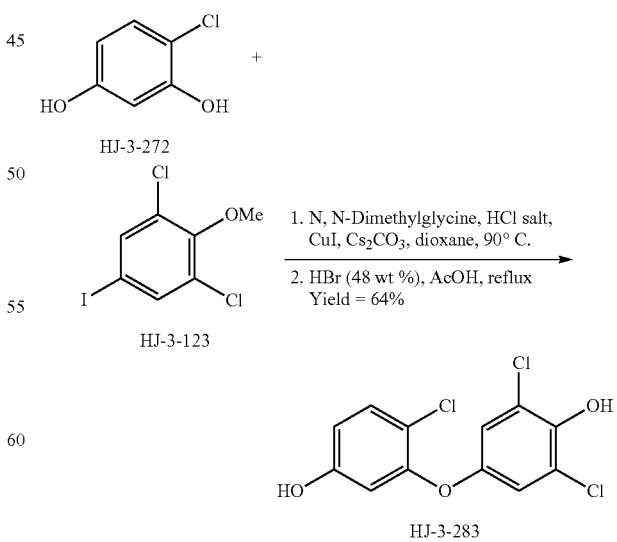

A solution of fluorescein (1.0 g, 2.5 mmol) in NaOH aqueous solution (12.5 M, 31 mL) was heated to reflux and stirred for 1 h under argon atmosphere. The reaction mixture was allowed to cool to room temperature, and carefully acidified with conc. HCl at 0° C. until large amount of precipitate was formed. Then the desired product HJ-3-278 [2513-23-7] was filtered, washed with water and dried in air for 24 h to afford as brown solid. Yield: 732 mg (quant.). $^1$H NMR (400 MHz, CDCl$_3$) δ 8.12 (d, J=7.7 Hz 1H), 7.76-7.68 (m, 1H), 7.78-7.61 (m, 1H), 7.39 (d, J=7.7 Hz, 1H), 6.95 (s, 1H), 6.48 (s, 1H); $^{13}$C NMR (100 MHz, CDCl$_3$) δ 202.3, 168.6, 164.6, 161.7, 141.4, 134.6, 133.7, 131.6, 131.0, 130.6, 128.5, 115.5, 113.2, 104.8.

A mixture of HJ-3-123 (422 mg, 2.66 mmol), HJ-3-272 (402 mg, 1.33 mmol), CuI (25 mg, 0.133 mmol), N,N- dimethylglycine hydrochloride (56 mg, 0.399 mmol), Cs$_2$CO$_3$ (867 mg, 2.66 mmol) and anhydrous 1,4-dioxane (5 mL) in a sealed flask was heated to 90° C. and stirred for 24 h under argon atmosphere. The reaction mixture was allowed to cool to room temperature, diluted with ethyl acetate and washed with 1 N HCl, water and brine. The organic layer was dried over anhydrous magnesium sulfate and concentrated in vacuo. The residue was dissolved in acetic acid (7 mL) and HBr (48 wt. % in H$_2$O, 7 mL), heated to reflux and stirred for 12 h under argon atmosphere. The reaction mixture was allowed to cool to room temperature, diluted with ethyl acetate and washed with 1 N HCl, water and brine. The target compound HJ-3-283 was isolated as a white sticky solid by flash chromatography on silica gel using EtOAc:Hexane (1:9) as an eluent. Yield: 260 mg (64%). $^1$H NMR (300 MHz, CD$_3$OD) δ 7.22 (d, J=8.7 Hz, 1H), 6.89 (s, 2H), 6.58 (dd, J=8.7, 2.7 Hz, 1H), 6.44 (d, J=2.7 Hz, 1H); $^{13}$C NMR (75 MHz, CD$_3$OD) δ 158.6, 153.7, 150.5, 146.7, 131.9, 123.9, 119.2, 116.2, 113.5, 108.6; LRMS (EI, 20 eV) m/z (%) 304 (26), 234 (M$^+$; 100); HRMS (EI): calcd for C$_{12}$H$_7$O$_3$Cl$_3$ (M$^+$): 303.9461. found: 303.9445.

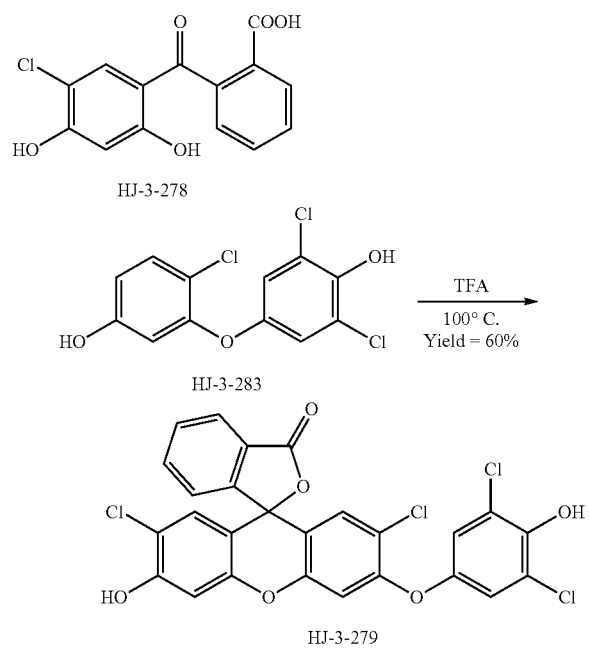

A solution of HJ-3-283 (92 mg, 0.30 mmol) and HJ-3-278 (176 mg, 0.60 mmol) in TFA (2 mL) in a sealed flask was heated to 100° C. and stirred for 12 h under argon atmosphere. The reaction mixture was allowed to cool to room temperature and azeotroped with toluene for 3 times. The target compound HJ-3-284 was isolated as a light yellow sticky solid by flash chromatography on silica gel using EtOAc:Hexane (3:7) as an eluent. Yield: 101 mg (60%). $^1$H NMR (300 MHz, CDCl$_3$) δ 8.08 (d, J=7.5 Hz, 1H), 7.75 (t, J=7.4 Hz, 1H), 7.70 (t, J=7.4 Hz, 1H), 7.20 (d, J=7.4 Hz, 1H), 7.04 (s, 2H), 6.87 (s, 1H), 6.83 (s, 1H), 6.75 (s, 1H), 6.72 (s, 1H), 6.16 (brs, 2H); $^{13}$C NMR (75 MHz, CDCl$_3$) 169.2, 154.7, 153.5, 152.1, 150.9, 150.6, 148.1, 145.6, 135.9, 130.7, 129.7, 128.1, 126.3, 125.8, 124.0, 121.9, 119.9, 116.6, 115.0, 112.0, 106.9, 104.3, 81.7; LRMS (EI) m/z (%) 562 (1), 71 (M$^+$; 100); HRMS (EI): calcd for C$_{26}$H$_{14}$O$_6$Cl$_4$ (M$^+$): 561.9358. found: 561.9358.

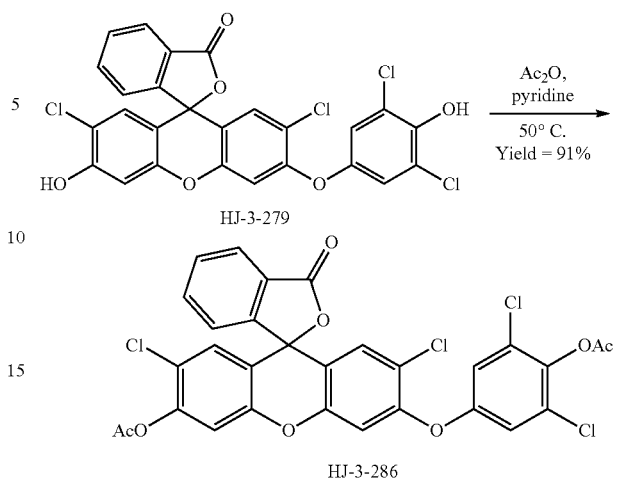

To a solution of HJ-3-284 (20 mg, 0.0356 mmol) in anhydrous pyridine (1 mL) at room temperature was added Ac$_2$O (3 mL) slowly under argon atmosphere. Then the resulting mixture was stirred at 50° C. for 2 h. The reaction mixture was allowed to cool to room temperature, diluted with ethyl acetate and washed with 1 N HCl, water and brine. The target compound HJ-3-286 was isolated as a white sticky solid by flash chromatography on silica gel using EtOAc:Hexane (1:9) as an eluent. Yield: 21 mg (91%). $^1$H NMR (300 MHz, CDCl$_3$) δ 8.09 (d, J=7.2 Hz, 1H), 7.82-7.74 (m, 1H), 7.74-7.66 (m, 1H), 7.23 (d, J=7.6 Hz, 1H), 7.12 (s, 1H), 7.05 (s, 2H), 6.95 (s, 1H), 6.90 (s, 1H), 6.87 (s, 1H), 2.40 (s, 3H), 2.36 (s, 3H); $^{13}$C NMR (75 MHz, CDCl$_3$) δ 168.6, 168.1, 167.5, 153.7, 153.3, 151.8, 150.4, 149.9, 148.6, 136.0, 130.9, 129.9, 129.1, 126.0, 125.9, 124.1, 122.9, 121.5, 118.7, 117.8, 116.3, 112.9, 109.0, 80.6, 20.7, 20.3; LRMS (EI, 20 eV) m/z (%) 646 (1), 481 (M; 100); HRMS (EI): calcd for C$_{30}$H$_{18}$O$_8$Cl$_4$ (M$^+$): 645.9570. found: 645.9572.

Example 2—Synthesis of Yellow Fluorogenic Compounds BXY2142, BXY2172 and BXY333

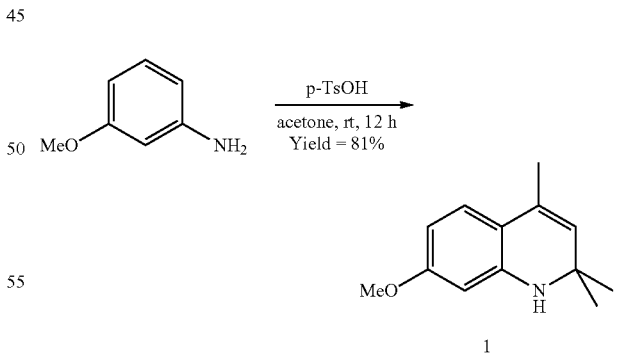

To a solution of 3-methoxyaniline (5 g, 40.6 mmol) in acetone (150 mL) was added p-TsOH (1.55 g, 8.1 mmol) under argon atmosphere. The resulting mixture was stirred at room temperature for 12 h. The reaction mixture was then concentrated in vacuo. The target compound 1 [1810-74-8] was isolated as a colorless oil by flash chromatography on silica gel using EtOAc:Hexane (1:19) as an eluent. Yield: 6.7 g (81%). $^1$H NMR (300 MHz, CDCl$_3$) δ 6.98 (d, J=8.4 Hz, 1H), 6.21 (dd, J=8.4, 2.3 Hz, 1H), 6.02 (d, J=2.3 Hz, 1H), 5.20 (s, 1H), 3.75 (s, 3H), 1.97 (s, 3H), 1.27 (s, 6H); $^{13}$C NMR (100 MHz, CDCl$_3$) δ 160.0, 144.6, 127.8, 125.8, 124.4, 115.0, 102.0, 98.3, 54.6, 51.6, 30.7, 18.4; LRMS (EI, 20 eV) m/z (%) 203 (M$^+$; 8), 188 (100); HRMS (EI): calcd for C$_{13}$H$_{17}$ON (M$^+$): 203.1310. found: 203.1306.

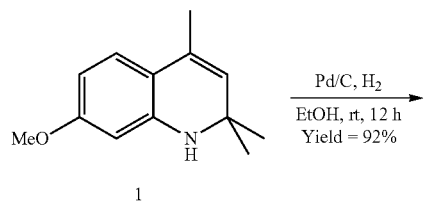

To a solution of 1 (2 g, 9.84 mmol) in EtOH (100 mL) was added Pd/C (0.97 g, 0.98 mmol) slowly under argon atmosphere. The resulting mixture was connected with a H$_2$ balloon and stirred at room temperature for 12 h. The reaction mixture was filtered through a pad of celite and concentrated in vacuo. The target compound 2 [41381-73-1] was isolated as a colorless oil by flash chromatography on silica gel using EtOAc:Hexane (1:19) as an eluent. Yield: 1.85 g (92%). $^1$H NMR (400 MHz, CDCl$_3$) δ 7.14 (d, J=8.4 Hz, 1H), 6.33 (dd, J=8.4, 2.3 Hz, 1H), 6.09 (d, J=2.3 Hz, 1H), 3.80 (s, 3H), 2.97-2.91 (m, 1H), 1.79 (dd, J=12.8, 5.5 Hz, 1H), 1.49 (t, J=12.5 Hz, 1H), 1.39 (d, J=6.7 Hz, 3H), 1.30 (s, 3H), 1.25 (s, 3H); $^{13}$C NMR (100 MHz, CDCl$_3$) δ 158.8, 144.7, 127.7, 118.0, 102.7, 99.2, 55.0, 49.3, 44.6, 31.5, 27.7, 27.0, 20.5; LRMS (EI, 20 eV) m/z (%) 205 (M$^+$; 41), 190 (100); HRMS (EI): calcd for C$_{13}$H$_{19}$ON (M$^+$): 205.1467. found: 205.1461.

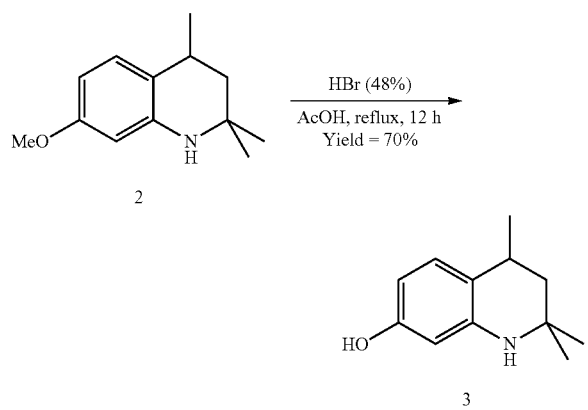

To a solution of 2 (1.5 g, 0.44 mmol) in AcOH (8 mL) at room temperature was added HBr (48 wt. % in H$_2$O; 8 mL) slowly. The resulting mixture was stirred under reflux for 12 h. The reaction mixture was allowed to cool to room temperature, diluted with ethyl acetate and washed with 1 N HCl, water and brine. The organic layer was dried over anhydrous magnesium sulfate and concentrated in vacuo. The target compound 3 was isolated as a colorless oil by flash column chromatography on silica gel, using EtOAc:Hexane (1:9) as an eluent. Yield 1.34 g (70%). $^1$H NMR (400 MHz, CDCl$_3$) δ 7.06 (d, J=8.3 Hz, 1H), 6.33-6.25 (m, 1H), 5.96 (s, 1H), 5.50 (br, 2H), 2.96-2.83 (m, 1H), 1.75 (dd, J=12.9, 5.5 Hz, 1H), 1.47 (t, J=12.5 Hz, 1H), 1.33 (d, J=6.6 Hz, 3H), 1.26 (s, 3H), 1.18 (s, 3H); $^{13}$C NMR (100 MHz, CDCl$_3$) δ 154.5, 144.4, 128.1, 118.6, 105.5, 101.9, 49.5, 44.4, 31.1, 27.2, 27.0, 20.6; LRMS (EI, 20 eV) m/z (%) 191 (M$^+$; 29), 176 (100); HRMS (EI): calcd for C$_{12}$H$_{17}$ON (M$^+$): 191.1310. found: 191.1305.

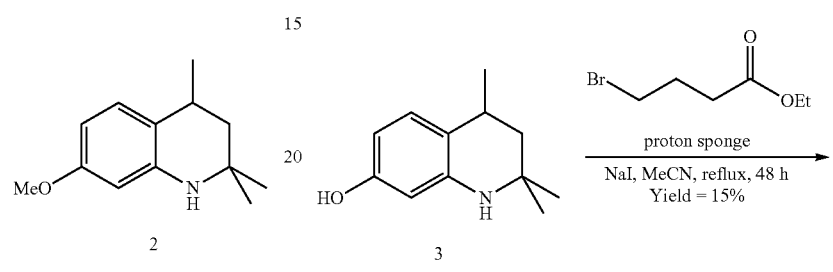

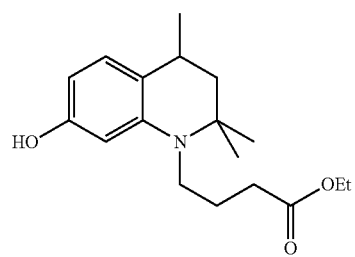

To a solution of 3 (1.34 g, 7.0 mmol) in dry MeCN (50 mL) were added NaI (210 mg, 1.40 mmol), proton sponge (3.0 g, 14 mmol) and ethyl-4-bromobutylate (1.52 mL, 10.5 mmol) successively under argon atmosphere. The resulting mixture was stirred under reflux for 48 h. Then the reaction mixture was filtered through a pad of celite, diluted with ethyl acetate and washed with 1 N HCl, water and brine. The organic layer was dried over anhydrous magnesium sulfate and concentrated in vacuo. The target compound 4 was isolated as a light yellow sticky solid by flash column chromatography on silica gel using EtOAc:Hexane (1:9) as an eluent. Yield 320 mg (15%). $^1$H NMR (400 MHz, CDCl$_3$) δ 6.96 (d, J=8.7 Hz, 1H), 6.21-6.10 (m, 2H), 5.92 (s, 1H), 4.22-4.15 (m, 2H), 3.37-3.27 (m, 1H), 3.09-2.99 (m, 1H), 2.86-2.75 (m, 1H), 2.37 (t, J=6.8 Hz, 2H), 2.03-1.92 (m, 1H), 1.91-1.80 (m, 1H), 1.70 (dd, J=12.9, 4.5 Hz, 1H), 1.50 (t, J=12.8 Hz, 1H), 1.32-1.26 (m, 9H), 1.15 (s, 3H); $^{13}$C NMR (100 MHz, CDCl$_3$) δ 173.8, 155.2, 146.1, 138.3, 126.7, 102.2, 98.8, 60.7, 54.6, 47.3, 44.6, 31.8, 29.7, 26.9, 25.0, 24.2, 20.3, 14.4; LRMS (EI, 20 eV) m/z (%) 305 (M$^+$; 52), 290 (100); HRMS (EI): calcd for C$_{18}$H$_{27}$O$_3$N (M$^+$): 305.1991. found: 305.1983.

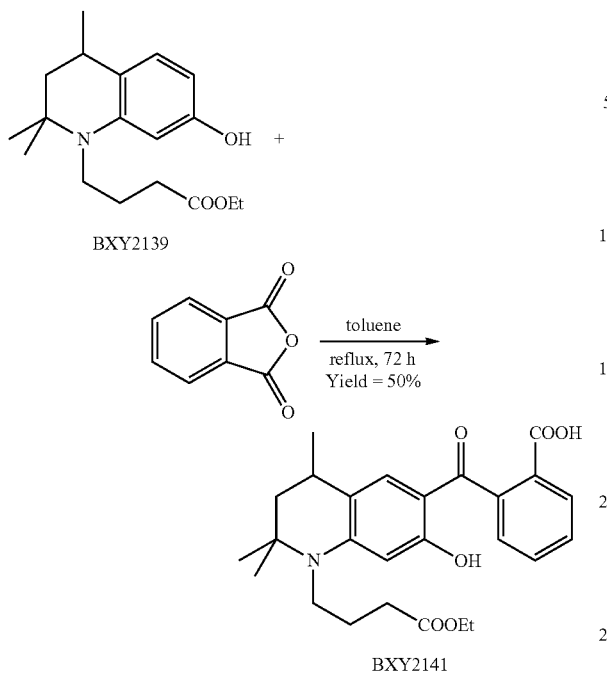
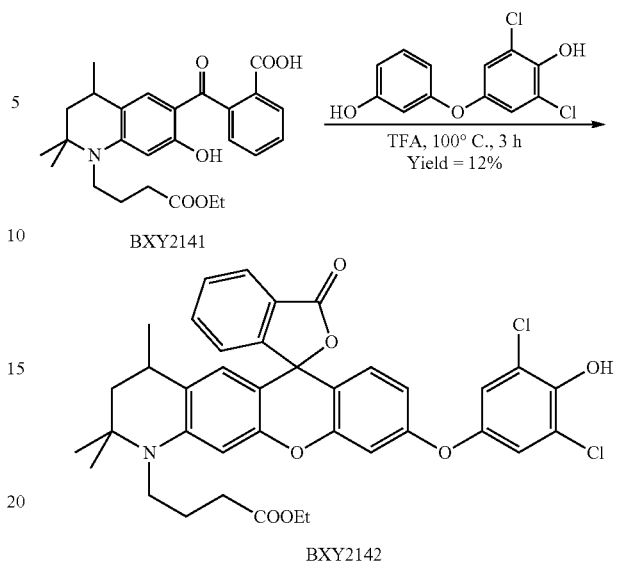

BXY2139 (150 mg, 0.49 mmol) and phthalic anhydride (87 mg, 0.58 mmol) were dissolved in dry toluene. The suspension was heated to reflux for 48 h, then cooled to room temperature. The solvent was removed in vacuo. The target compound BXY2141 was isolated as a light yellow sticky solid by flash chromatography on silica gel using MeOH:CH$_2$Cl$_2$ (1:20) as an eluent. Yield: 100 mg (64%). $^1$H NMR (400 MHz, CDCl$_3$) δ 12.46 (s, 1H), 8.09 (d, J=7.7 Hz, 1H), 7.61 (t, J=7.4 Hz, 1H), 7.52 (t, J=7.6 Hz, 1H), 7.36 (d, J=7.4 Hz, 2H), 6.74 (s, 1H), 6.08 (s, 1H), 4.18 (q, J=7.1 Hz, 2H), 3.50-3.36 (m, 1H), 3.27-3.15 (m, 1H), 2.62 (dd, J=11.9, 5.8 Hz, 1H), 2.39 (t, J=6.8 Hz, 2H), 2.02-1.84 (m, 2H), 1.66 (dd, J=13.1, 4.1 Hz, 1H), 1.47 (t, J=13.1 Hz, 1H), 1.34 (s, 3H), 1.30 (d, J=7.2 Hz, 3H), 1.19 (s, 3H), 0.99 (d, J=6.4 Hz, 3H); $^{13}$C NMR (75 MHz, CDCl$_3$) δ 199.3, 198.1, 173.0, 170.5, 164.0, 151.9, 141.1, 132.4, 130.9, 129.8, 129.1, 128.0, 119.9, 109.4, 97.4, 60.6, 55.7, 46.0, 44.6, 31.5, 29.4, 26.0, 25.6, 23.4, 19.4, 14.2.

BXY2141 (60 mg, 0.132 mmol) and HJ-3-266 (36 mg, 0.132 mmol) were dissolved in TFA (2 mL). The reaction mixture was stirred at 100° C. for 3 h. The reaction mixture was allowed to cool to room temperature and the solvent was removed in vacuo. The target compound BXY2142 was isolated as a light yellow sticky solid by flash chromatography on silica gel using EtOAc:Hexane (1:3) as an eluent. Yield: 10 mg (12%). $^1$H NMR (400 MHz, CDCl$_3$) δ 8.02 (d, J=7.4 Hz, 1H), 7.67 (t, J=7.4 Hz, 1H), 7.61 (t, J=7.4 Hz, 1H), 7.24-7.18 (m, 1H), 7.03 (s, 2H), 6.76 (s, 1H), 6.71 (d, J=8.7 Hz, 1H), 6.61 (d, J=8.8 Hz, 1H), 6.39 (s, 1H), 6.37 (s, 1H), 4.19 (q, J=7.1 Hz, 2H), 3.43-3.33 (m, 1H), 3.20-3.07 (m, 1H), 2.76-2.57 (m, 1H), 2.41 (t, J=6.9 Hz, 2H), 2.07-1.85 (m, 2H), 1.70-1.62 (m, 1H), 1.51-1.38 (m, 1H), 1.33-1.27 (m, 6H), 1.16 (s, 3H), 1.07-0.93 (m, 3H). $^{13}$C NMR (75 MHz, CDCl$_3$) δ 173.19, 169.61, 158.83, 158.78, 152.94, 152.87, 151.04, 150.95, 148.54, 147.13, 146.91, 145.07, 134.81, 134.75, 129.57, 129.51, 127.21, 127.03, 125.66, 125.21, 124.89, 124.75, 124.04, 121.58, 120.22, 114.61, 113.21, 105.28, 104.55, 97.68, 84.32, 60.58, 54.97, 54.83, 46.42, 46.34, 44.58, 44.36, 31.63, 29.42, 29.28, 26.78, 26.60, 25.59, 25.09, 23.52, 23.34, 19.66, 19.47, 14.23.

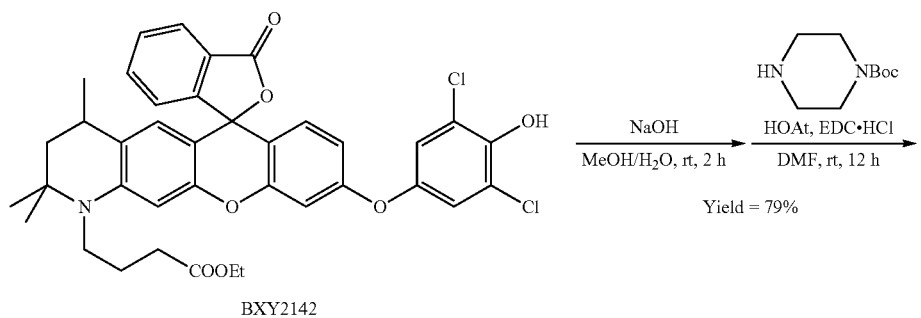

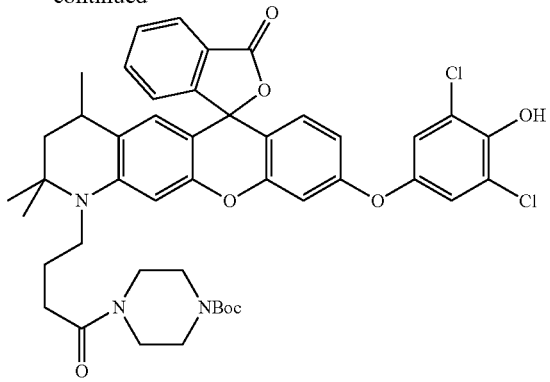

BXY2153

To a solution of BXY2142 (42 mg, 0.061 mmol) in MeOH (3.5 mL) was added a solution of NaOH (15 mg, 0.366 mmol) in H₂O (3.5 mL). The resulting mixture was stirred at room temperature for 2 h. The reaction mixture was diluted with ethyl acetate and washed with 1 N HCl, water and brine. The organic layer was dried over anhydrous magnesium sulfate and concentrated in vacuo to obtain the crude residue. To a solution of the crude residue and amine (13 mg, 0.067 mmol) in anhydrous DMF (1 mL) was added HOAt (9 mg, 0.067 mmol) and stirred for 30 min at room temperature under argon atmosphere. Then the resulting mixture was added with EDC HCl (15 mg, 0.078 mmol) and stirred at room temperature for 12 h. The reaction mixture was diluted with EtOAc and washed with 1 N HCl, water and brine. The organic layer was dried over anhydrous magnesium sulfate and concentrated in vacuo. The target compound BXY2153 was isolated as a red sticky solid by flash chromatography on silica gel using MeOH:CH₂Cl₂ (1:20) as an eluent. Yield: 40 mg (86%). ¹H NMR (400 MHz, CDCl₃) δ 8.02 (d, J=7.5 Hz, 1H), 7.67 (t, J=7.0 Hz, 1H), 7.61 (t, J=7.5 Hz, 1H), 7.24-7.18 (m, 1H), 7.03 (s, 2H), 6.76-6.73 (m, 1H), 6.71 (d, J=8.7, 1H), 6.60 (d, J=8.7 Hz, 1H), 6.40 (s, 1H), 6.39 (s, 1H), 3.67-3.60 (m, 2H), 3.53-3.37 (m, 7H), 3.22-3.11 (m, 1H), 2.75-2.57 (m, 1H), 2.42 (t, J=6.5 Hz, 2H), 2.05-1.87 (m, 2H), 1.69-1.6 (m, 1H), 1.47 (s, 9H), 1.46-1.43 (m, 10H), 1.31 (d, J=3.6 Hz, 3H), 1.16 (s, 3H), 1.07-0.92 (m, 3H); ¹³C NMR (100 MHz, CDCl₃) δ 170.95, 169.35, 158.70, 154.51, 152.93, 152.75, 150.84, 148.89, 147.17, 146.99, 144.55, 134.84, 129.58, 124.92, 124.08, 121.65, 120.31, 114.49, 113.21, 105.36, 97.74, 80.43, 55.02, 54.83, 46.44, 45.30, 44.59, 41.46, 30.54, 30.45, 29.34, 28.36, 26.85, 26.66, 25.71, 25.18, 23.55, 23.35, 19.63, 19.49.

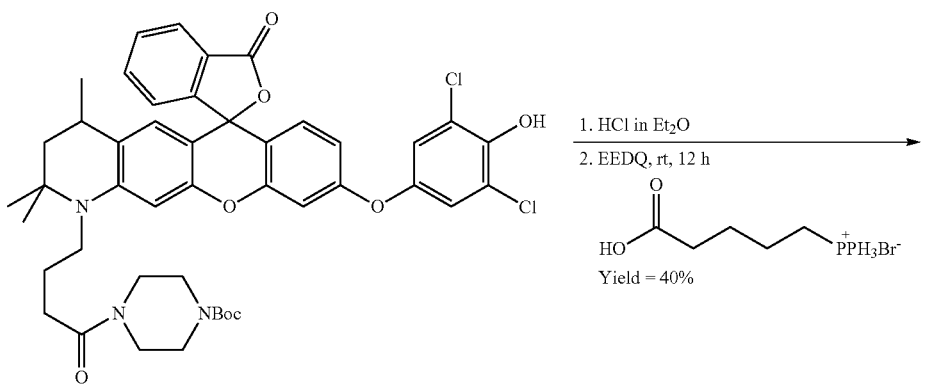

BXY2153

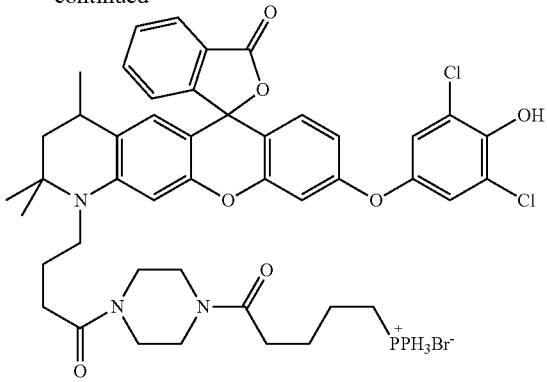

BXY2172

To a solution of BXY2153 (30 mg, 0.04 mmol) in dry Et₂O (0.5 mL) at room temperature was added HCl (2 M in dry Et₂O, 0.5 mL) under argon atmosphere. The resulting mixture was stirred at room temperature for 0.5 h and concentrated in vacuo to obtain the crude amine. To a solution of (4-carboxybutyl)triphenylphosphonium bromide (53 mg, 0.04 mmol) and EEDQ (33 mg, 0.013 mmol) in dry DCM (2 mL) at 0° C. was added the solution of crude amine in dry DCM (2 mL) under argon atmosphere. The resulting mixture was stirred at 0° C. to room temperature for 12 h. The reaction mixture was diluted with DCM, and washed with 1 N HCl, water, and brine. The organic layer was dried over anhydrous magnesium sulfate and concentrated in vacuo. The target compound BXY2172 was isolated as a red sticky solid by flash column chromatography on silica gel by using EtOH:CHCl₃ (1:4) as an eluent. Yield: (16 mg) (40%).

¹H NMR (400 MHz, CDCl₃) δ 8.01 (d, J=7.5 Hz, 1H), 7.84-7.67 (m, 16H), 7.61 (t, J=7.3 Hz, 1H), 7.24-7.18 (m, 1H), 7.04 (s, 2H), 6.94 (s, 1H), 6.74 (d, J=8.4 Hz, 1H), 6.64 (d, J=8.6 Hz, 1H), 6.49 (d, J=3.1 Hz, 1H), 6.39 (d, J=3.8 Hz, 1H), 3.83-3.45 (m, 9H), 3.24-3.10 (m, 1H), 2.77-2.56 (m, 1H), 2.50-2.40 (m, 2H), 2.07-1.87 (m, 2H), 1.83-1.54 (m, 10H), 1.32 (m, 3H), 1.34-1.30 (s, 3H), 1.07-0.95 (m, 3H); ¹³C NMR (100 MHz, CDCl₃) δ 171.48, 171.19, 171.15, 169.67, 169.64, 157.04, 156.97, 154.63, 153.12, 151.07, 150.97, 147.31, 147.12, 135.02, 133.67, 133.57, 130.54, 130.42, 129.75, 129.53, 127.20, 127.00, 125.85, 124.87, 124.67, 124.19, 118.98, 118.77, 117.91, 114.23, 107.50, 104.11, 97.78, 65.60, 55.04, 54.85, 46.56, 46.41, 45.93, 45.73, 44.95, 44.55, 41.40, 32.01, 30.45, 29.69, 29.54, 29.34, 26.84, 26.67, 25.80, 25.61, 25.44, 25.23, 23.32, 21.92, 19.69, 19.46.

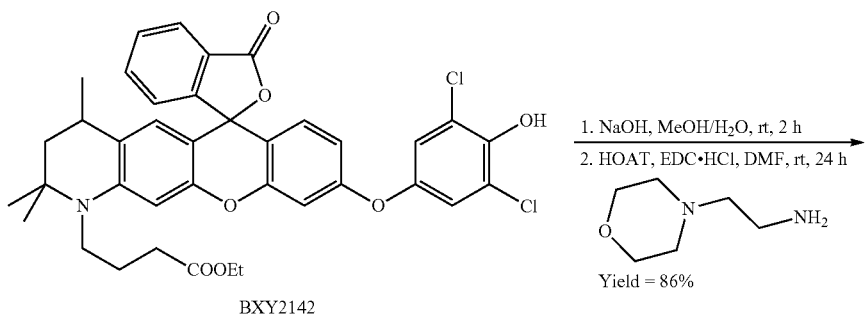

BXY2142

1. NaOH, MeOH/H₂O, rt, 2 h
2. HOAT, EDC·HCl, DMF, rt, 24 h

Yield = 86%

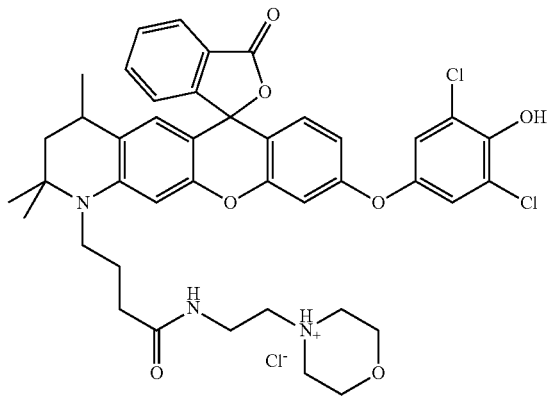

BXY333

To a solution of BXY2142 (42 mg, 0.061 mmol) in MeOH (3.5 mL) was added a solution of NaOH (15 mg, 0.366 mmol) in H$_2$O (3.5 mL). The resulting mixture was stirred at room temperature for 2 h. The reaction mixture was diluted with ethyl acetate and washed with 1 N HCl, water and brine. The organic layer was dried over anhydrous magnesium sulfate and concentrated in vacuo to obtain the crude residue. To a solution of the crude residue (20 mg, 0.030 mmol) and 2-morpholinoethylamine (5 mg, 0.036 mmol) in anhydrous DMF (2 mL) was added HOAt (4.5 mg, 0.036 mmol). The resulting mixture was stirred for 30 min at room temperature under argon atmosphere. Then the resulting mixture was added with EDC-HCl (8.06 mg, 0.042 mmol) and stirred at room temperature for 12 h. The reaction mixture was diluted with EtOAc and washed with 1 N HCl, water and brine. The organic layer was dried over anhydrous magnesium sulfate and concentrated in vacuo. The target compound BXY333 was isolated as a pink sticky solid by flash chromatography on silica gel using MeOH:CH$_2$Cl$_2$ (1:50) as an eluent. Yield: 40 mg (86%). $^1$H NMR (400 MHz, CDCl$_3$) δ 8.02 (d, J=7.5 Hz, 1H), 7.67 (t, J=7.0 Hz, 1H), 7.61 (t, J=7.5 Hz, 1H), 7.24-7.18 (m, 1H), 7.03 (s, 2H), 6.76-6.73 (m, 1H), 6.71 (d, J=8.7 Hz, 1H), 6.60 (d, J=8.7 Hz, 1H), 6.40 (s, 1H), 6.39 (s, 1H), 3.67-3.60 (m, 2H), 3.53-3.37 (m, 7H), 3.22-3.11 (m, 1H), 2.75-2.57 (m, 1H), 2.42 (t, J=6.5 Hz, 2H), 2.05-1.87 (m, 2H), 1.69-1.6 (m, 1H), 1.47 (s, 9H), 1.46-1.43 (m, 10H), 1.31 (d, J=3.6 Hz, 3H), 1.16 (s, 3H), 1.07-0.92 (m, 3H); $^{13}$C NMR (100 MHz, CDCl$_3$) δ 170.95, 169.35, 158.70, 154.51, 152.93, 152.75, 150.84, 148.89, 147.17, 146.99, 144.55, 134.84, 129.58, 124.92, 124.08, 121.65, 120.31, 114.49, 113.21, 105.36, 97.74, 80.43, 55.02, 54.83, 46.44, 45.30, 44.59, 41.46, 30.54, 30.45, 29.34, 28.36, 26.85, 26.66, 25.71, 25.18, 23.55, 23.35, 19.63, 19.49.

Example 3—Synthesis of Red Fluorogenic Compound HJ-3-259

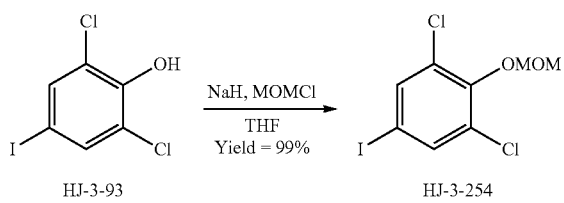

To a mixture of HJ-3-93 (722 mg, 2.5 mmol) in dry THF at 0° C. was added NaH (150 mg, 3.75 mmol) with vigorous stirring under argon atmosphere. After 1 h, MOMCl (285 µL, 3.75 mmol) was added dropwise to the reaction mixture at 0° C. Then the reaction mixture was stirred at room temperature for another 1 h and quenched with water. The resulting mixture was diluted with ethyl acetate and washed with 1 N HCl, water and brine. The organic layer was dried over anhydrous magnesium sulfate and concentrated in vacuo. The target compound HJ-3-254 [939989-91-0] was isolated as a white solid by flash chromatography on silica gel using Et$_2$O:Hexane (1:99) as an eluent. Yield: 832 mg (99%). $^1$H NMR (400 MHz, CDCl$_3$) δ 7.59 (s, 2H), 5.14 (s, 2H), 3.65 (s, 3H); $^{13}$C NMR (100 MHz, CDCl$_3$) δ 149.9, 137.3, 130.4, 99.3, 86.5, 58.2; LRMS (EI, 20 eV) m/z (%) 334 (63), 332 (M$^+$; 100); HRMS (EI): calcd for C$_8$H$_7$O$_3$Cl$_2$I: 331.8868. found: 331.8861.

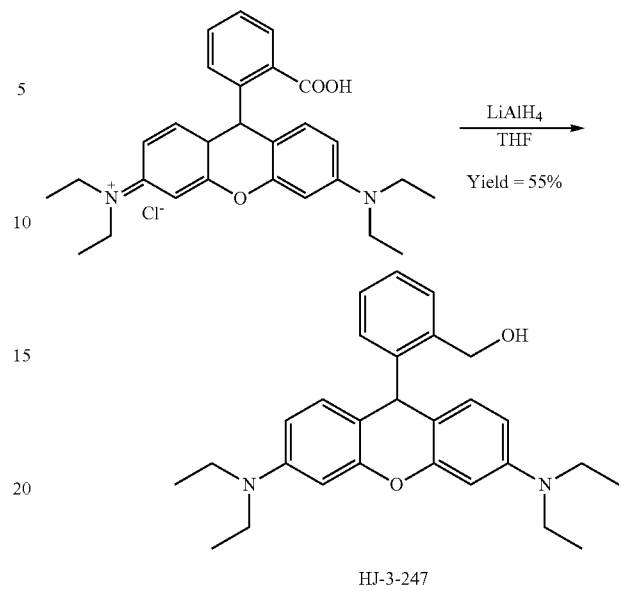

To a solution of rhodamine B (10.0 g, 20.9 mmol) in dry THF (50 mL) at 0° C. was added LiAlH$_4$ (4.0 g, 105.4 mmol) portion by portion under argon atmosphere. The resulting mixture was stirred at room temperature for 48 h, then quenched with ethyl acetate (50 mL) carefully. The resulting mixture was diluted with water and CHCl$_3$, and extracted with CHCl$_3$ for 3 times. The organic layer was dried over anhydrous magnesium sulfate and concentrated in vacuo. The target compound HJ-3-247 [1491155-13-5] was isolated a sticky pink solid by flash chromatography on silica gel using EtOAc:Hexane (1:4) as an eluent. Yield: 4.93 g (55%). $^1$H NMR (400 MHz, CDCl$_3$) δ 7.55-7.45 (m, 1H), 7.38-7.27 (m, 3H), 6.81 (d, J=8.6 Hz, 2H), 6.54 (s, 2H), 6.37 (d, J=7.8 Hz, 2H), 5.47 (s, 1H), 4.69 (s, 2H), 3.40 (q, J=6.9 Hz, 8H), 2.38 (brs, 1H), 1.25 (t, J=7.0 Hz, 12H); $^{13}$C NMR (100 MHz, CDCl$_3$) δ 151.6, 147.5, 144.9, 138.3, 131.1, 130.0, 128.9, 127.8, 126.5, 111.5, 107.4, 98.7, 62.7, 44.3, 39.2, 12.5.

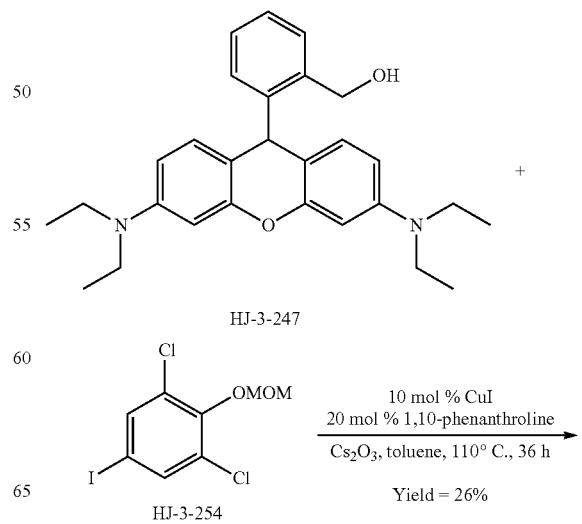

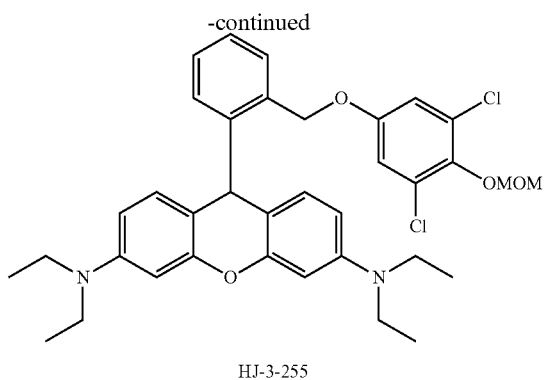

HJ-3-255

An oven-dried flask was charged with copper(I) iodide (29 mg, 0.15 mmol), 1,10-phenanthroline (54 mg, 0.30 mmol), Cs$_2$CO$_3$ (489 mg, 1.50 mmol), HJ-3-247 (323 mg, 0.75 mmol), HJ-3-254 (499 mg, 1.50 mmol) and dry toluene (7.5 mL) under argon atmosphere. The flask was sealed and heated to 100° C. for 36 h. The resulting mixture was allowed to cool down to room temperature and filtered over a pad of celite and concentrated in vacuo. The target compound HJ-3-255 was isolated as a sticky purple solid by flash chromatography on silica gel using EtOAc:Hexane (1:9). Yield: 123 mg (26%). $^1$H NMR (400 MHz, CDCl$_3$) δ 7.39-7.22 (m, 4H), 6.70 (d, J=8.4 Hz, 2H), 6.64 (s, 2H), 6.34 (s, 2H), 6.29 (d, J=8.4 Hz, 2H), 5.31 (s, 1H), 5.05 (s, 2H), 4.79 (s, 2H), 3.65 (s, 3H), 3.31 (q, J=6.7 Hz, 8H), 1.13 (t, J=6.6 Hz, 12H); $^{13}$C NMR (100 MHz, CDCl$_3$) δ 155.0, 151.7, 147.9, 144.7, 143.3, 134.0, 131.5, 130.1, 129.5, 128.4, 128.4, 126.9, 115.4, 110.3, 107.6, 99.4, 98.6, 68.2, 58.2, 44.4, 40.5, 12.7; ESI-MS m/z (%) 635.2 ([M+H]$^+$; 73), 633.2 ([M–H]$^+$; 100).

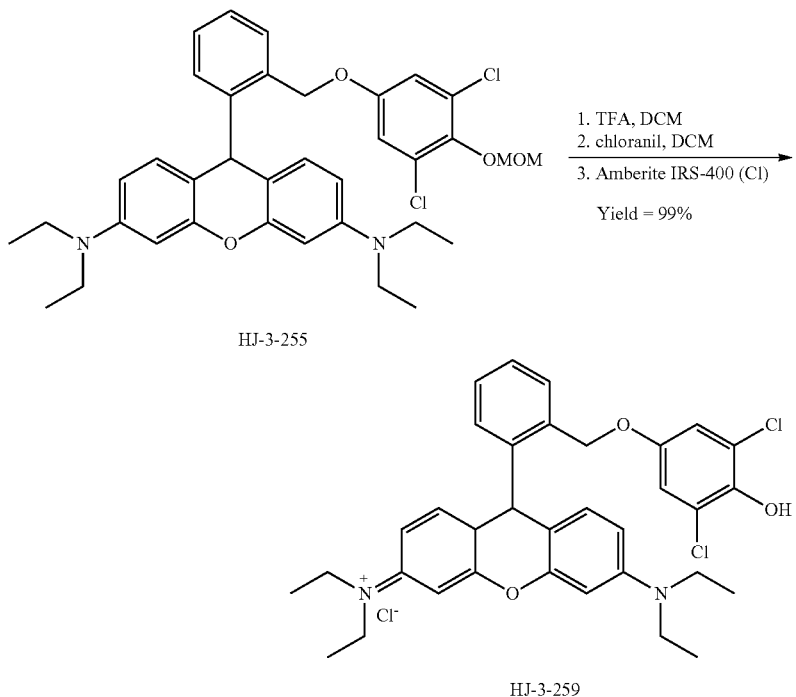

To a solution of HJ-3-255 (38 mg, 0.06 mmol) in DCM (3 mL) at room temperature was added TFA (3 mL) dropwise. The reaction mixture was stirred at room temperature for 1 h, then concentrated and azeotroped with toluene for 3 times. The residue was redissolved in DCM (6 mL) and chloranil (44 mg, 0.18 mmol) was added under argon atmosphere. The reaction mixture was stirred at room temperature for 1 h until TLC showed that the reaction was complete. The resulting mixture was concentrated in vacuo. The crude product was purified by flash chromatography on silica gel using EtOAc:Hexane (1:9) as an eluent to afford a red solid. Then the solid was dissolved in methanol and loaded on the chloride exchange resin (Amberite IRA-400 (Cl), AR) to exchange the counter ion to desired chloride ion. The resin was filtered off and the filtrate was concentrated under reduced pressure to afford pure compound HJ-3-259 as a stick purple solid (123 mg, 26%). $^1$H NMR (400 MHz, CDCl$_3$) δ 7.74-7.65 (m, 2H), 7.64-7.56 (m, 1H), 7.27 (d, J 7.1 Hz, 1H), 7.07 (d, J 9.0 Hz, 2H), 6.83 (d, J=9.0

Hz, 2H), 6.76 (s, 2H), 6.18 (s, 2H), 4.78 (s, 2H), 3.62 (q, J=6.3 Hz, 8H), 1.34 (t, J=6.3 Hz, 12H); $^{13}$C NMR (100 MHz, CDCl$_3$) δ 157.7, 156.6, 155.7, 150.3, 143.7, 135.3, 131.5, 131.4, 130.6, 129.8, 129.6, 129.1, 122.1, 114.3, 114.0, 113.3, 96.4, 84.3, 69.1, 46.2, 12.6; ESI-MS m/z (%) 589.2 (M$^+$; 100), 411.5 (72).

Example 4—Synthesis of Green Fluorogenic Compound HYY166, HKOH-1 and HKOH-1R

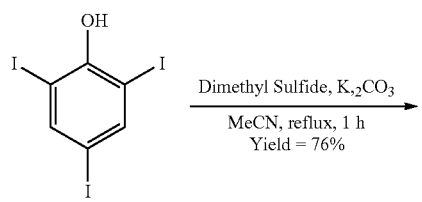

HYY155

To a solution of 2,4,6-triiodophenol (5.67 g, 12 mmol) in MeCN at room temperature were added K$_2$CO$_3$ (3.71 g, 25.2 mmol) and dimethyl sulfide (2.4 mL, 25.2 mmol) under argon atmosphere. Then the mixture was stirred under reflux for 1 h. The reaction mixture was allowed to cool to room temperature, diluted with ethyl acetate, and washed with NH$_4$OH, water and brine. The organic layer was then dried over anhydrous magnesium sulfate and concentrated in vacuo. The target compound HYY155 [63238-41-5] was isolated by flash chromatography on silica gel by using EtOAc:Hexane (1:99) as an eluent. Yield: 4.68 g (76%). $^1$H NMR (400 MHz, CDCl$_3$) δ 8.03 (s, 2H), 3.82 (s, 3H); $^{13}$C NMR (100 MHz, CDCl$_3$) δ 159.1, 147.2, 91.9, 89.5, 60.9.

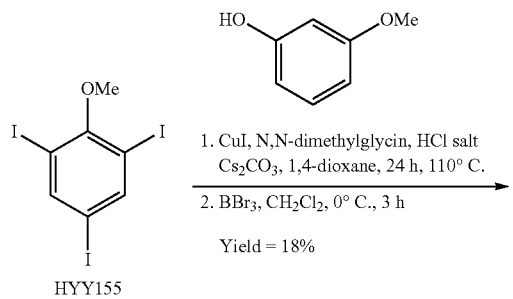

HYY164

A mixture of HYY155 (2.00 g, 4.1 mmol), 3-methoxyl phenol (1.02 g, 8.2 mmol), Cs$_2$CO$_3$ (5.42 g, 16.47 mmol), CuI (0.16 g, 0.82 mmol) and N,N-dimethyl glycine hydrochloride (0.35 g, 2.5 mmol) in anhydrous 1,4-dioxane (6 mL) was stirred at 110° C. under argon atmosphere for 24 h. The resulting mixture was filtered over a pad of celite, washed with ethyl acetate and concentrated in vacuo. The crude product was dissolved in dry CH$_2$Cl$_2$ (5 mL) and then treated with BBr$_3$ (1 M in CH$_2$Cl$_2$, 1.2 mL, 1.2 mmol) via syringe over 5 min under argon atmosphere. The mixture was allowed to stir at 0° C. for 3 h. The reaction was quenched with water carefully and stirred until all precipitates were dissolved. The product was extracted with CH$_2$Cl$_2$, and washed with brine. The combined organic layer was dried over anhydrous magnesium sulfate and concentrated in vacuo. The target compound HYY164 was isolated by flash chromatography on silica gel by using EtOAc:Hexane (1:5) as an eluent. Yield: 132 mg (70%). $^1$H NMR (400 MHz, CDCl$_3$) δ 7.39 (s, 2H), 7.15 (t, J=7.6 Hz, 1H), 6.58 (d, J=8.0 Hz, 1H), 6.50 (d, J=8.1 Hz, 1H), 6.46 (s, 1H), 5.87 (brs, 2H); $^{13}$C NMR (100 MHz, CDCl$_3$) δ 158.6, 157.0, 150.6, 150.4, 130.7, 130.2, 110.7, 110.3, 105.7, 81.6.

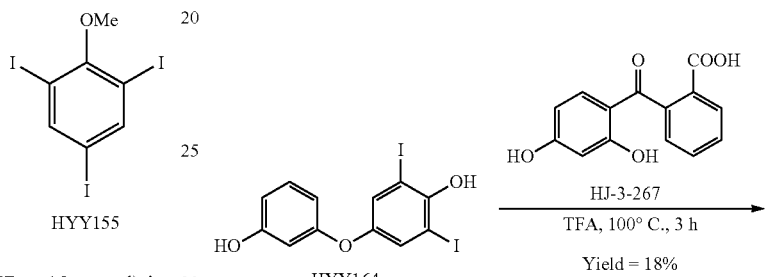

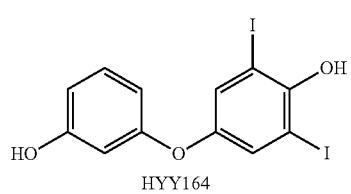

HYY166

HYY164 (50 mg, 0.11 mmol) and HJ-3-267 (42.66 mg, 0.17 mmol) were dissolved in TFA (3 mL) in a sealed tube. The reaction mixture was heated to 100° C. and stirred for 3 h under argon atmosphere. The reaction mixture was allowed to cool to room temperature and azeotroped with toluene for 3 times. The target compound HYY166 was isolated as a light yellow sticky solid by flash chromatography on silica gel by using EtOAc:Hexane (3:7) as an eluent. Yield: 20 mg (61%). $^1$H NMR (400 MHz, CDCl$_3$) δ 8.03 (d, J=7.5 Hz, 1H), 7.70 (t, J=7.2 Hz, 1H), 7.63 (t, J=7.2 Hz, 1H), 7.43 (s, 2H), 7.19 (d, J=7.6 Hz, 1H), 6.76-6.70 (m, 3H), 6.62 (dd, J=8.8, 2.4 Hz, 1H), 6.60-6.51 (m, 2H); $^{13}$C NMR (100 MHz, CDCl$_3$) δ 170.5, 159.7, 158.4, 153.0, 152.6, 152.4, 151.2, 149.5, 135.5, 131.0, 130.1, 129.7, 129.3, 126.7, 125.3, 124.18, 113.7, 112.8, 110.6, 105.3, 103.3, 81.6.

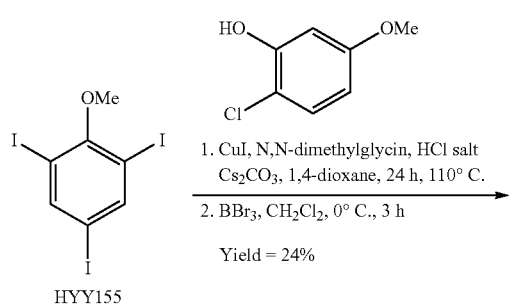

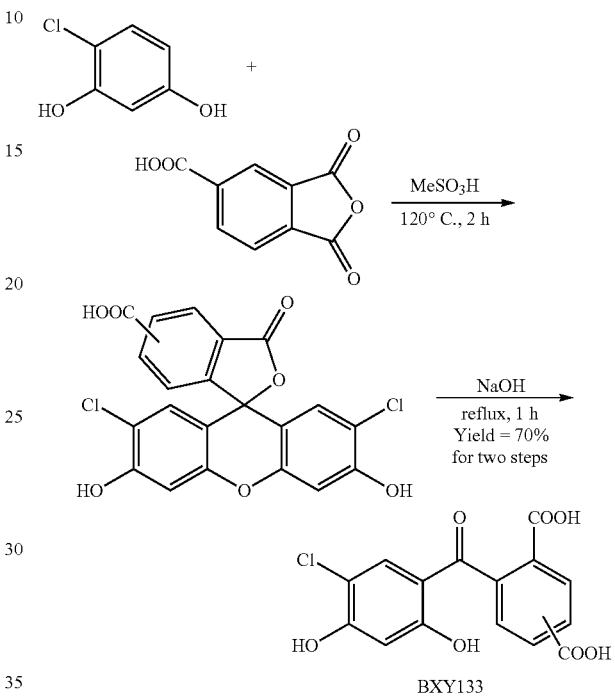

A mixture of HYY155 (1.0 g, 2.06 mmol), 2-chloro-5-methoxyphenol (0.65 g, 4.12 mmol), $Cs_2CO_3$ (2.71 g, 8.23 mmol), CuI (0.078 g, 0.41 mmol) and N,N-dimethyl glycine-HCl (0.172 g, 1.23 mmol) was dissolved in anhydrous 1,4-dioxane (6 mL) under argon, The mixture was allowed to stirred at 110° C. for 24 h, filtered over a pad of celite, washed with ethyl acetate and concentrated in vacuo. The crude product was dissolved in dry $CH_2Cl_2$ (5 mL) and then treated with $BBr_3$ (1 M in $CH_2Cl_2$, 2.3 mL, 2.3 mmol) via syringe over 5 minutes under argon. The mixture was allowed to stir at 0° C. for 3 h. The reaction was quenched with water carefully and stirred until all precipitates dissolved. The product was extracted with $CH_2Cl_2$, and washed with brine. The combined organic layer was dried over $MgSO_4$ and concentrated in vacuum. The target compound BXY571 was isolated by flash chromatography on silica gel using EtOAc:Hexane (1:4) as an eluent. Yield: 241 mg (24%). $^1$H NMR (400 MHz, Acetone-$d_6$) δ 8.40 (brs, 2H), 7.43 (s, 2H), 7.27 (d, J=8.7 Hz, 1H), 6.66 (dd, J=8.7, 2.7 Hz, 1H), 6.52 (d, J=2.7 Hz, 1H); $^{13}$C NMR (100 MHz, Acetone-d) δ 156.8, 152.3, 151.3, 150.2, 130.4, 128.4, 114.1, 112.1, 107.0, 83.1.

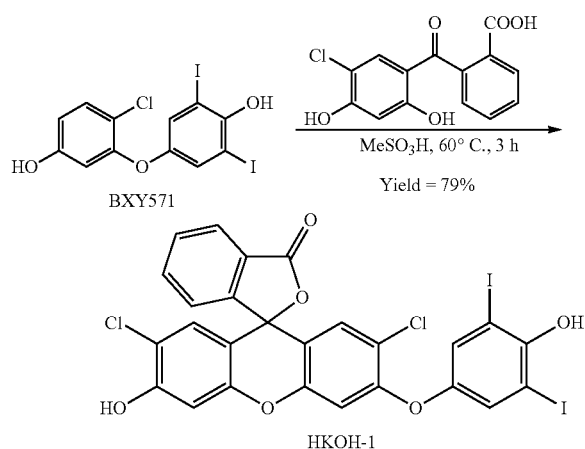

BXY571 (63 mg, 0.13 mmol) and HJ-3-278 (56.62 mg, 0.19 mmol) were dissolved in $MeSO_3H$ (3 mL) in a sealed tube. The reaction mixture was heated to 100° C. and stirred for 3 h under argon atmosphere. The reaction mixture was allowed to cool to room temperature and azeotroped with toluene for 3 times. The target compound HKOH-1 was isolated as a light yellow sticky solid by flash chromatography on silica gel, by using EtOAc:Hexane (2:8) as an eluent. Yield: 77 mg (79%). $^1$H NMR (400 MHz, $CDCl_3$/$CD_3OD$) δ 8.09 (d, J=7.6 Hz, 1H), 7.84 (t, J=6.8 Hz, 1H), 7.80 (t, J=7.4 Hz, 1H), 7.50 (s, 2H), 7.31 (d, J=7.6 Hz, 1H), 6.83 (s, 2H), 6.79 (s, 1H), 6.65 (s, 1H).

2-Chlororesorcinol (1.37 g, 9.5 mmol) and 1,2,4-tricarboxylic anhydride (0.91 g, 4.7 mmol) were dissolved into $MeSO_3H$ (16 mL) and the reaction mixture were heated to 120° C. for 2 h. Then the reaction mixture was cooled to room temperature and was poured into ice-cold water and filtered through a sintered funnel. The solid was washed with ice-cold water and dried in air for 12 h. Then the crude product was directly dissolved into 50 mL NaOH (50% w/v in water) solution. The reaction mixture was heated under reflux for 2 h. The reaction mixture was cooled into ice-cold water and acidified with concentrated HCl. Then the solution was extracted with EtOAc for three times and washed with water and brine. The crude product was purified by column chromatography, using MeOH:$CH_2Cl_2$ (1:33) as an eluent. Yield: 1.08 g (70% for two steps). $^1$H NMR (400 MHz, $CD_3OD$) δ 8.72 (d, J=1.4 Hz, 0.5H), 8.34 (dd, J=7.9, 1.6 Hz, 0.5H), 8.26 (dd, J=8.1, 1.6 Hz, 0.5H), 8.20 (d, J=8.1 Hz, 0.5H), 7.97 (d, J=1.4 Hz, 0.5H), 7.51 (d, J=7.9 Hz, 0.5H), 6.97 (s, 0.5H), 6.95 (s, 0.5H), 6.50-6.48 (m, 1H); $^{13}$C NMR (100 MHz, $CDCl_3$) δ 201.1, 201.0, 167.9 (2C), 167.8, 167.7, 164.6, 164.5, 161.7, 145.0, 141.3, 139.4, 135.5, 134.5, 134.4, 133.5, 132.7, 131.9, 131.8, 130.9, 129.3, 128.9, 115.2, 115.1, 113.3, 104.9, 104.8.

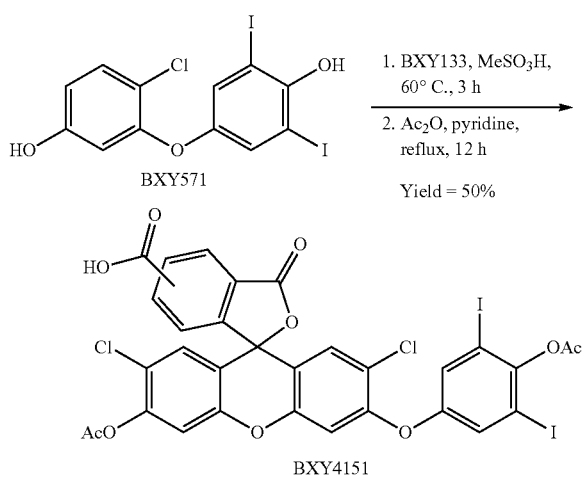

BXY571 (320 mg, 0.66 mmol) and BXY4133 (300 mg, 0.82 mmol) were dissolved into MeSO₃H and the reaction mixture was heated at 60° C. for 3 h. The reaction was cooled to room temperature, diluted with EtOAc and washed with water and brine. The combined organic layer was dried over MgSO₄ and concentrated in vacuum. The crude product was dissolved in a mixture of pyridine and Ac₂O (2 mL/6 mL) and the reaction mixture was heated under reflux for 12 h. After the resulting mixture was cooled to room temperature, it was diluted with EtOAc and washed with 1 N HCl, water and brine. The combined organic layer was dried over MgSO₄ and concentrated in vacuum. The target product BXY4151 was purified by column chromatography on silica gel, using EtOAc:Hexane (2:3) as an eluent. Yield: 288 mg (50%). $^1$H NMR (400 MHz, CDCl₃) δ 8.77 (s, 0.5H), 8.44 (d, J=8.0 Hz, 0.5H), 8.39 (d, J=8.0 Hz, 0.5H), 8.16 (d, J=8.0 Hz, 0.5H), 7.92 (s, 0.5H), 7.48 (s, 1H), 7.47 (s, 1H), 7.33 (d, J=8.0 Hz, 0.5H), 7.12 (s, 1H), 6.92-6.84 (m, 3H), 2.41 (s, 3H), 2.35 (s, 3H); $^{13}$C NMR (100 MHz, CDCl₃) δ 168.8, 168.6, 167.9, 167.8, 167.4, 167.4, 155.9, 153.8, 153.4, 151.9, 150.0, 149.5, 149.5, 148.6, 148.5, 138.0, 137.1, 136.5, 132.5, 132.3, 129.5, 129.3, 128.7, 127.8, 126.2, 125.9, 125.6, 124.2, 122.8 (2C), 121.0, 120.9, 116.7, 114.6, 112.8, 108.0, 90.3 80.9, 80.7, 21.2, 20.5.

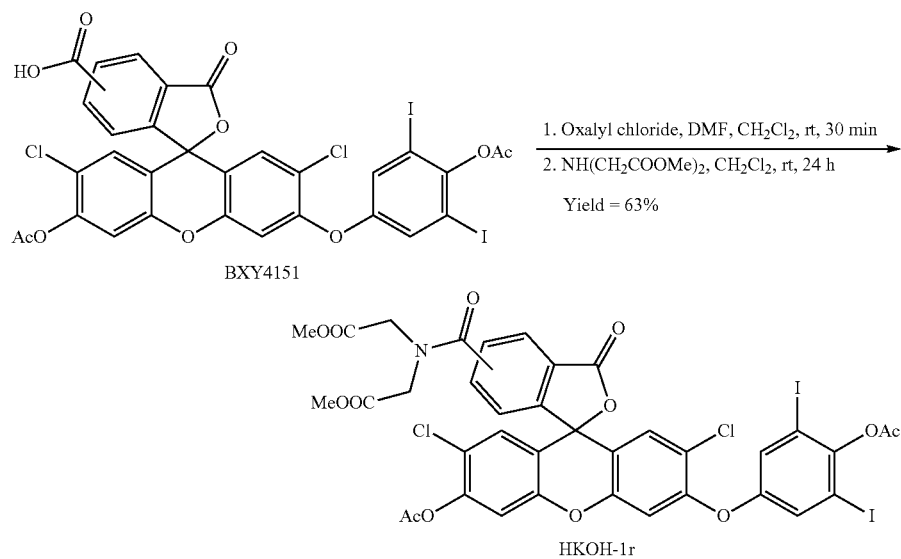

To a solution of BXY4151 (51 mg, 0.06 mmol) in anhydrous CH₂Cl₂ (1 mL) at room temperature was added oxalyl chloride (8 μL, 0.09 mmol). Then a drop of DMF was added and the reaction mixture was stirred at room temperature for 30 min. The solvent was evaporated in vacuo. The crude acyl chloride was directly dissolved in anhydrous CH₂Cl₂ and dimethyl iminodiacetate hydrochloride (17.8 mg, 0.09 mmol) was added. The resulting mixture was stirred at room temperature for 24 h. The resulting mixture was quenched with water, extracted with EtOAc, and washed with water and brine. The target product HKOH-1r was purified by column chromatography on silica gel using EtOAc:Hexane (2:5) as an eluent. Yield: 38 mg (63%) $^1$H NMR (400 MHz, CDCl₃) δ 8.18 (s, 0.5H), 8.14 (d, J=7.9 Hz, 0.5H), 7.87 (d, J=7.7 Hz, 0.5H), 7.78 (d, J=7.7 Hz, 0.5H), 7.51 (s, 1H), 7.49 (s, 1H), 7.33-7.26 (m, 1H), 7.14 (s, 1H), 6.94-6.84 (m, 3H), 4.42-3.96 (m, 4H), 3.81 (s, 1.5H), 3.80 (s, 1.5H), 3.76 (s, 1.5H), 3.56 (s, 1.5H), 2.43 (s, 3H), 2.37 (s, 3H).

Example 5—Sensitive and Selective Detection of Hypochlorous Acid with Green Fluorogenic Compound HKOCl-3

This Example shows that green fluorogenic compound HKOCl-3 sensitively and selectively detects hypochlorous acid. Specifically, Compound HKOCl-3 is dissolved in 0.1 M phosphate buffer at pH 7.4 to form a 10 μM solution, with excitation and emission spectra at 490 nm and 527 nm, respectively. The 10 μM solution of compound HKOCl-3 is treated with hypochlorous acid at various concentrations. FIG. 1A shows that the florescence intensity of compound HKOCl-3 increases with increasing concentration of hypochlorous acid.

Figure 1B:
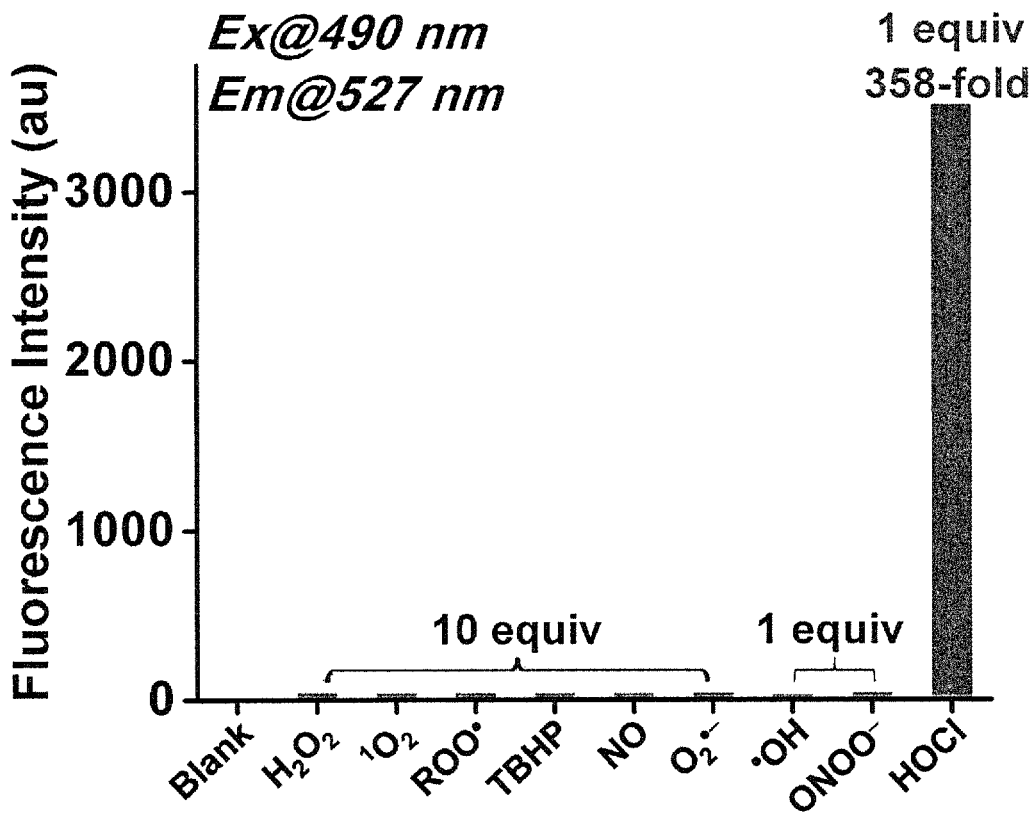
FIG. 1B shows a graph of fluorescence intensity (au) of compound HKOCl-3 treated with various reactive oxygen species (ROS) and reactive nitrogen species (RNS).

The reactivity of compound HKOCl-3 is compared toward different reactive oxygen species (ROS) and reactive nitrogen species (RNS). Specifically, the 10 μM solution of compound HKOCl-3 is treated with various ROS and RNS. The concentration of highly reactive oxygen species (hydroxyl radical ($^{\bullet}$OH), hypochlorous acid (HOCl), and peroxynitrite (ONOO$^-$)) is 10 μM. The concentration of $^1O_2$, $O_2^{\bullet-}$, $^{\bullet}$NO, ROO$^{\bullet}$, TBHP and $H_2O_2$ is 100 μM. FIG. 1B shows that treatment with hypochlorous acid results in a much higher increase in fluorescence intensity of compound HKOCl-3 than treatment with other ROS and RNS.

Example 6—Sensitive and Selective Detection of Hypochlorous Acid with Green Fluorogenic Compound HJ-3-279

Figure 2A:
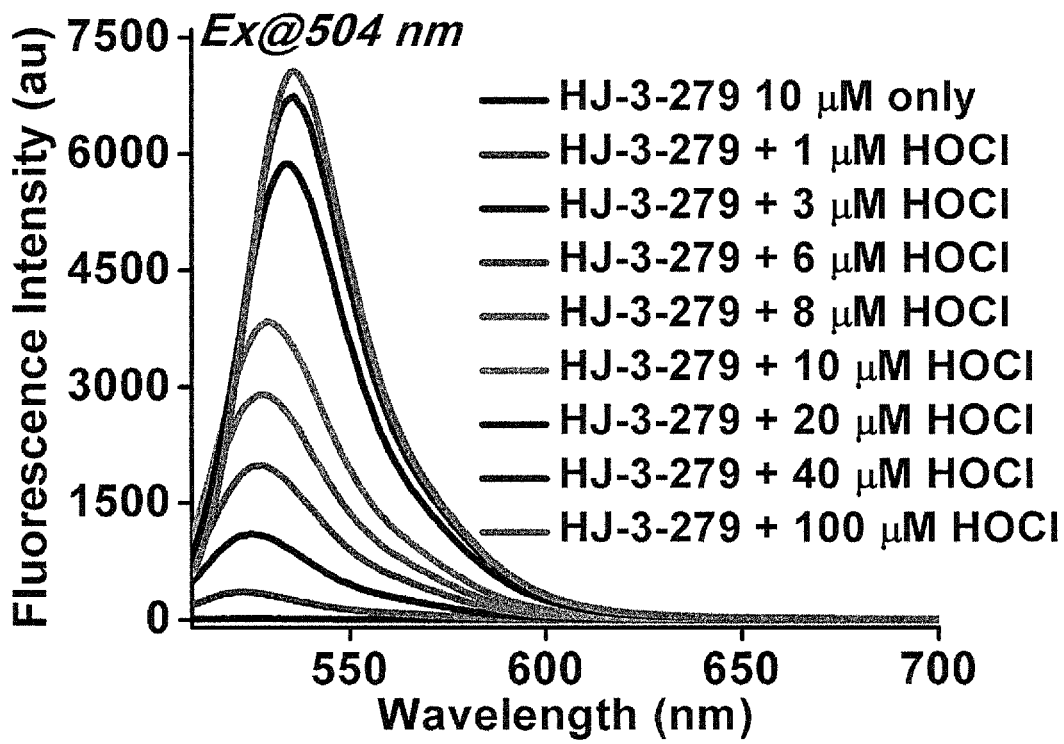
FIG. 2A shows a graph of fluorescence intensity (au) of compound HJ-3-279 for each of HJ-3-279 (10 μM), HJ-3-279+1 μM HOCl, HJ-3-279+3 μM HOCl, HJ-3-279+6 μM HOCl, HJ-3-279+8 μM HOCl, HJ-3-279+10 μM HOCl, HJ-3-279+20 μM HOCl, HJ-3-279+40 μM HOCl, and HJ-3-279+100 μM HOCl.

This Example shows that green fluorogenic compound HJ-3-279 sensitively and selectively detects hypochlorous acid. Specifically, compound HJ-3-279 is dissolved in 0.1 M phosphate buffer at pH 7.4 to form a 10 μM solution, with excitation and emission spectra at 490 nm and 527 nm, respectively. The 10 μM solution of Compound HJ-3-279 is treated with hypochlorous acid at various concentrations. FIG. 2A shows that the florescence intensity of Compound HJ-3-279 increases with increasing concentration of hypochlorous acid.

Figure 2B:
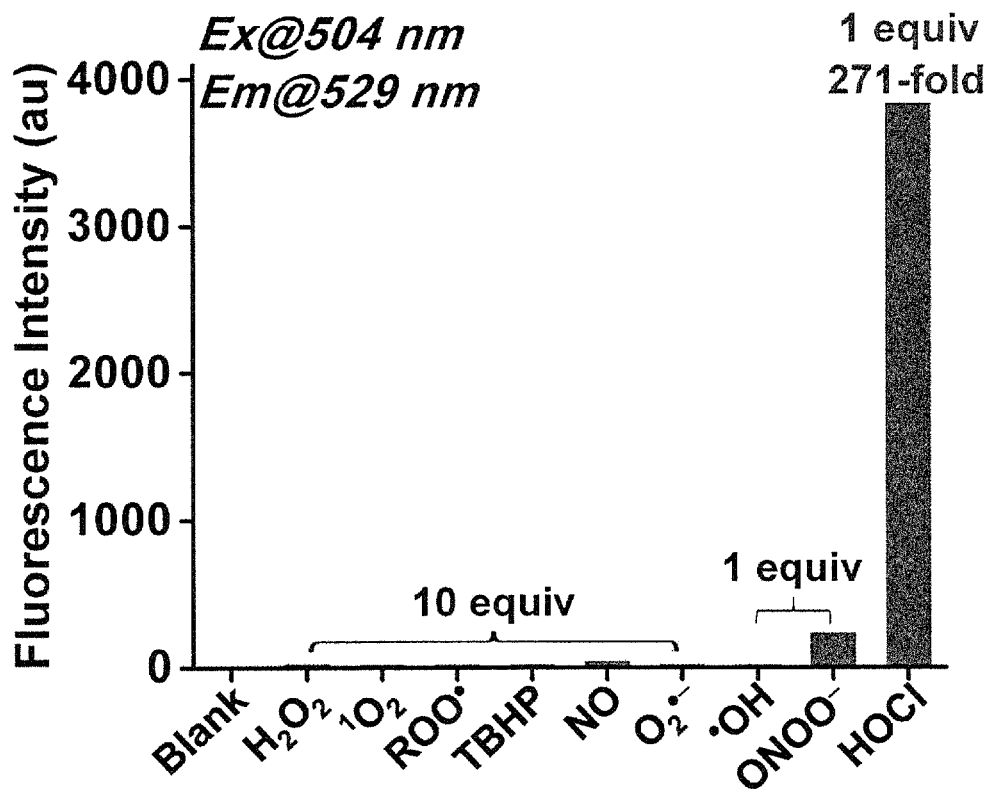
FIG. 2B shows a graph of fluorescence intensity (au) of compound HJ-3-279 treated with various ROS and RNS.

The reactivity of compound HJ-3-279 is compared toward different reactive oxygen species (ROS) and reactive nitrogen species (RNS). Specifically, the 10 μM solution of compound HJ-3-279 is treated with various ROS and RNS. The concentration of highly reactive oxygen species (hydroxyl radical ($^{\bullet}$OH), hypochlorous acid (HOCl), and peroxynitrite (ONOO$^-$)) is 10 μM. The concentration of $^1O_2$, $O_2^{\bullet-}$, $^{\bullet}$NO, ROO$^{\bullet}$, TBHP and $H_2O_2$ is 100 μM. FIG. 2B shows that treatment with hypochlorous acid results in a much higher increase in fluorescence intensity of compound HJ-3-279 than treatment with other ROS and RNS.

Example 7—Sensitive and Selective Detection of Hypochlorous Acid with Yellow Fluorogenic Compound BXY2142

Figure 3A:
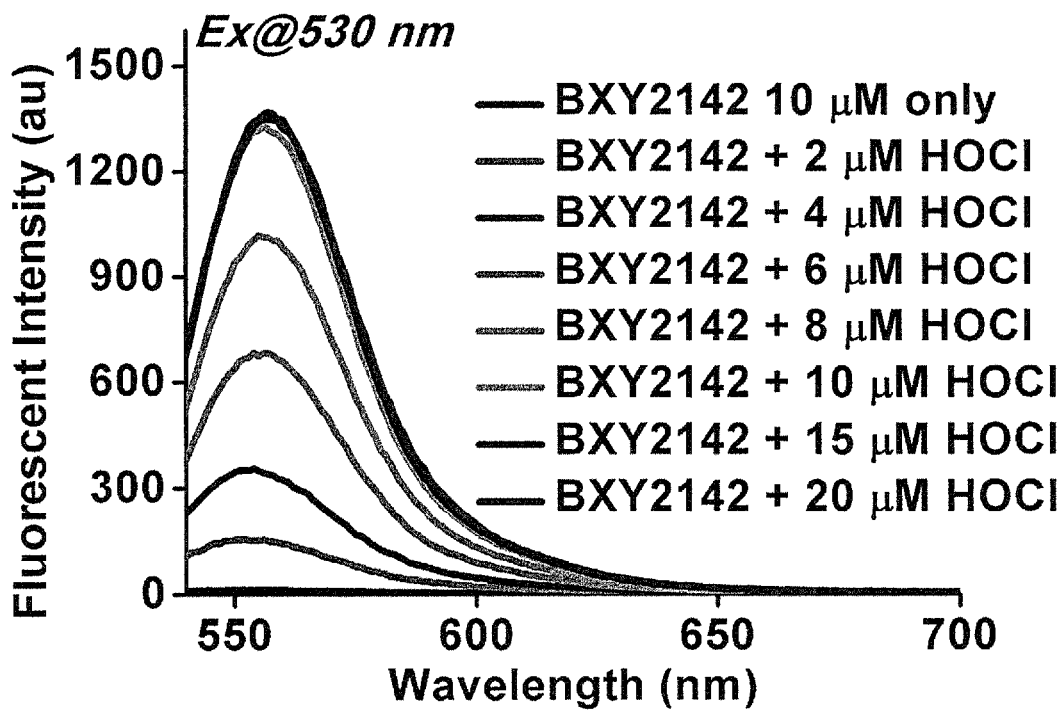
FIG. 3A shows a graph of fluorescence intensity (au) of compound BXY2142 for each of BXY2142 (10 μM), BXY2142+2 μM HOCl, BXY2142+4 μM HOCl, BXY2142+6 μM HOCl, BXY2142+8 μM HOCl, BXY2142+10 μM HOCl, BXY2142+15 μM HOCl, and BXY2142+20 μM HOCl.

This Example shows that yellow fluorogenic Compound BXY2142 sensitively and selectively detects hypochlorous acid. Specifically, Compound BXY2142 is dissolved in 0.1 M phosphate buffer at pH 7.4 to form a 10 μM solution, with excitation and emission spectra at 530 nm and 557 nm, respectively. The 10 μM solution of Compound BXY2142 is treated with hypochlorous acid at various concentrations. FIG. 3A shows that the florescence intensity of Compound BXY2142 increases with increasing concentration of hypochlorous acid.

Figure 3B:
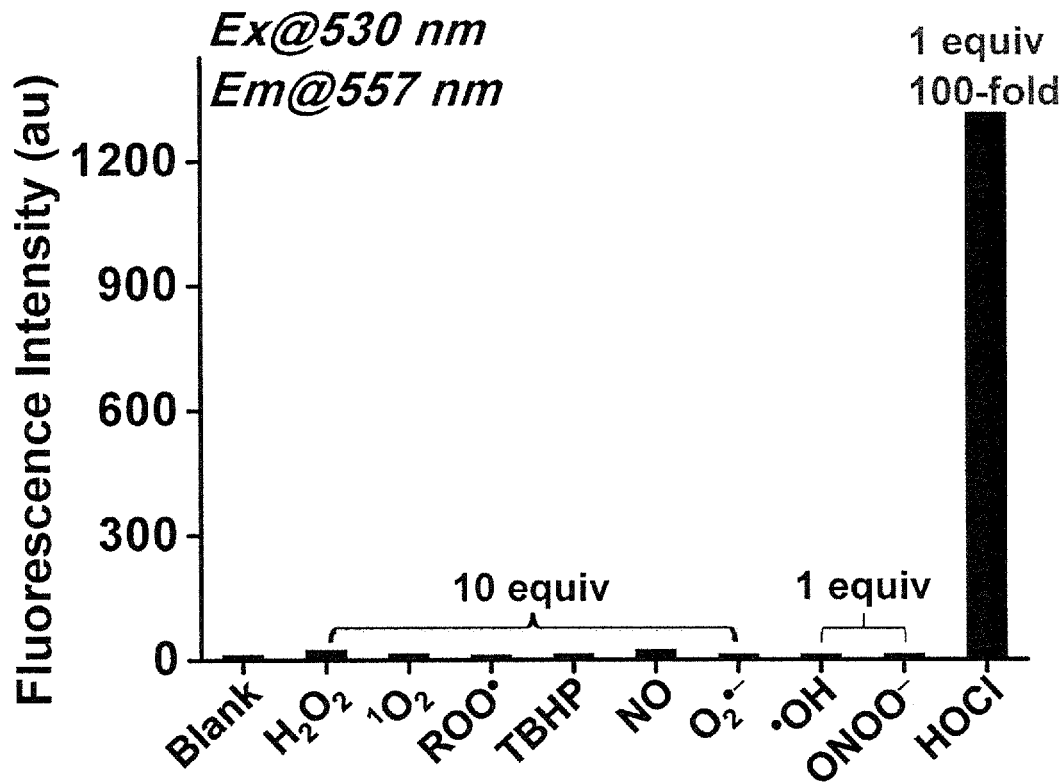
FIG. 3B shows a graph of fluorescence intensity (au) of compound BXY2142 treated with various ROS and RNS.

The reactivity of compound BXY2142 is compared toward different reactive oxygen species (ROS) and reactive nitrogen species (RNS). Specifically, the 10 μM solution of compound BXY2142 is treated with various ROS and RNS. The concentration of highly reactive oxygen species (hydroxyl radical ($^{\bullet}$OH), hypochlorous acid (HOCl), and peroxynitrite (ONOO$^-$)) is 10 μM. The concentration of $^1O_2$, $O_2^{\bullet-}$, $^{\bullet}$NO, ROO$^{\bullet}$, TBHP and $H_2O_2$ is 100 μM. FIG. 3B shows that treatment with hypochlorous acid results in a much higher increase in fluorescence intensity of compound HKOCl-3 than treatment with other ROS and RNS.

Example 8—Sensitive and Selective Detection of Hypochlorous Acid with Red Fluorogenic Compound HJ-3-259

Figure 4A:
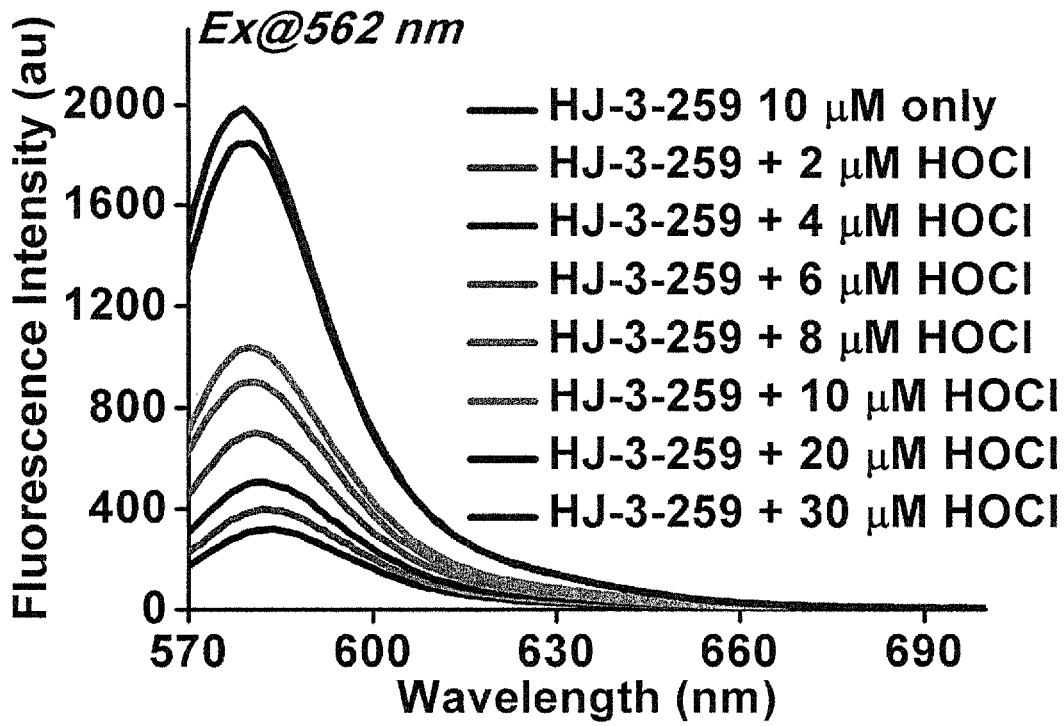
FIG. 4A shows a graph of fluorescence intensity (au) of compound HJ-3-259 for each of HJ-3-259 (10 μM), HJ-3-259+2 μM HOCl, HJ-3-259+4 μM HOCl, HJ-3-259+61 μM HOCl, HJ-3-259+8 μM HOCl, HJ-3-259+10 μM HOCl, HJ-3-259+20 μM HOCl, and HJ-3-259+30 μM HOCl.

This Example shows that red fluorogenic compound HJ-3-259 sensitively and selectively detects hypochlorous acid. Specifically, compound HJ-3-259 is dissolved in 0.1 M phosphate buffer at pH 7.4 to form a 10 μM solution, with excitation and emission spectra at 562 nm and 585 nm, respectively. The 10 μM solution of Compound HJ-3-259 is treated with hypochlorous acid at various concentrations. FIG. 4A shows that the florescence intensity of Compound HJ-3-259 increases with increasing concentration of hypochlorous acid.

Figure 4B:
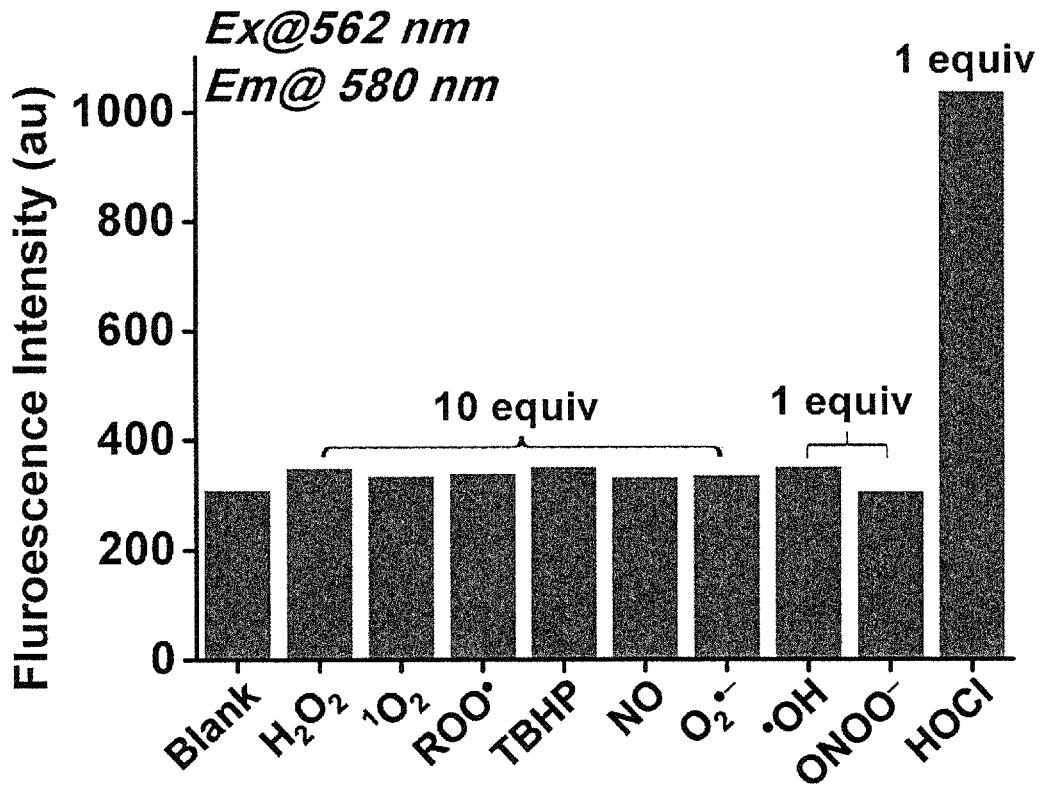
FIG. 4B shows a graph of fluorescence intensity (au) of compound HJ-3-259 treated with various ROS and RNS.
Figure 5:
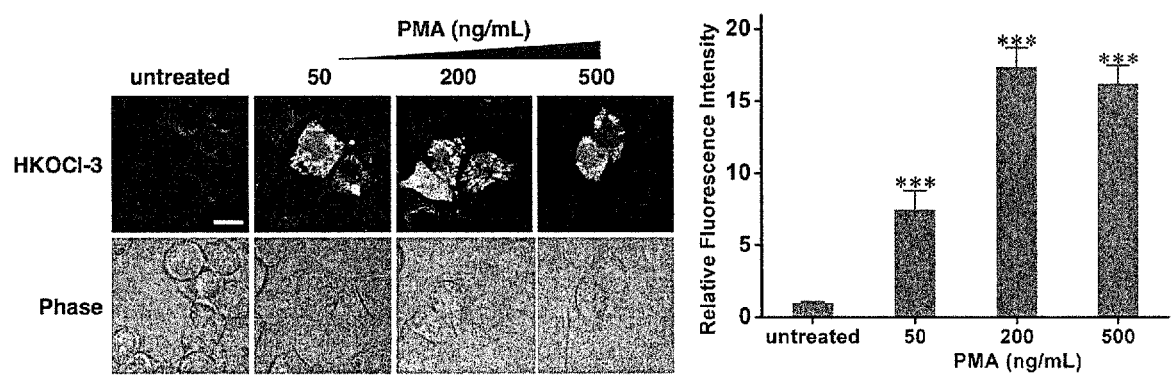
FIG. 5 shows confocal imaging of RAW264.7 cells co-incubated with HKOCl-3 (1 μM) and a dose gradient of PMA (phorbol myristate acetate: 50-500 ng/mL) for 30 minutes before imaging (left). Relative mean fluorescence levels of cells in the same groups imaged were quantified (right). Data are mean±s.e.m., n=50-100 cells; ***, p<0.001 versus untreated cells. Scale bar=10 μm.
Figure 6:
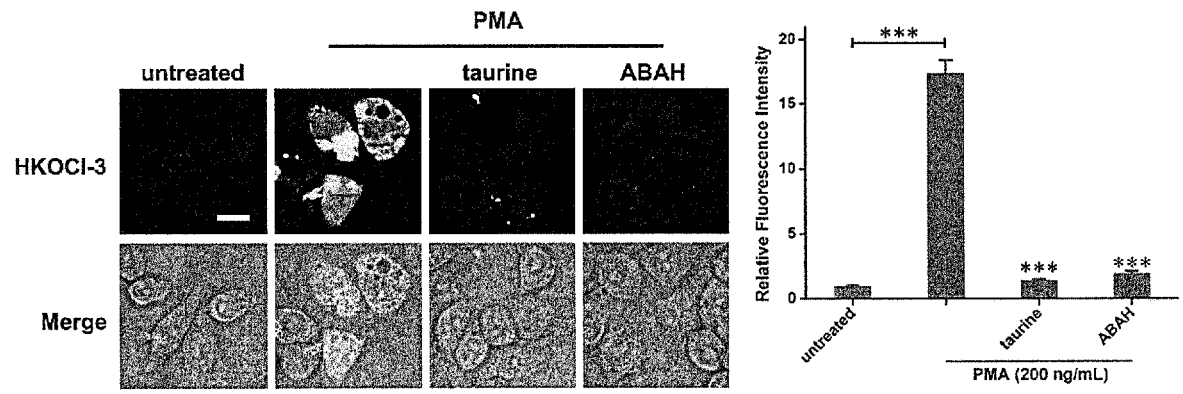
FIG. 6 shows confocal imaging of RAW264.7 cells co-incubated, before imaging, with HKOCl-3 (1 μM) with or without PMA (200 ng/mL) and taurine (10 mM) or ABAH (50 μM) (left). Merge: fluorescence and phase images merged. Relative mean fluorescence levels of cells in the same groups imaged were quantified (right). Scale bar represents 10 μm. Data are mean±s.e.m., n=27-60 cells; ***, p<0.001 versus untreated cells or control.
Figure 7:
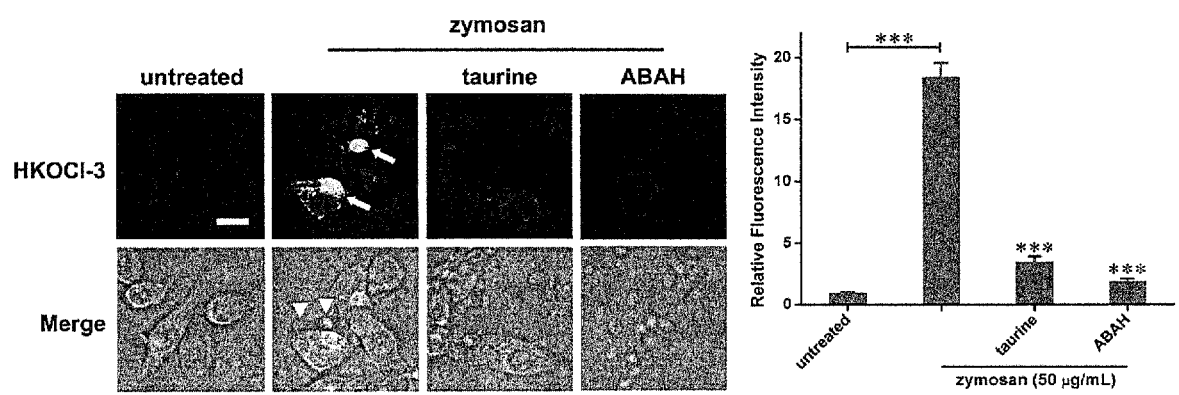
FIG. 7 shows confocal imaging of RAW264.7 cells co-incubated, before imaging, with HKOCl-3 (1 μM) with or without zymosan (50 μg/mL) and taurine (10 mM) or ABAH (50 μM) (left). Merge: fluorescence and phase images merged. Relative mean fluorescence levels of cells in the same groups imaged were quantified (right). Scale bar represents 10 μm. Data are mean±s.e.m., n=39-60 cells; ***, p<0.001 versus untreated cells or control.
Figure 8:
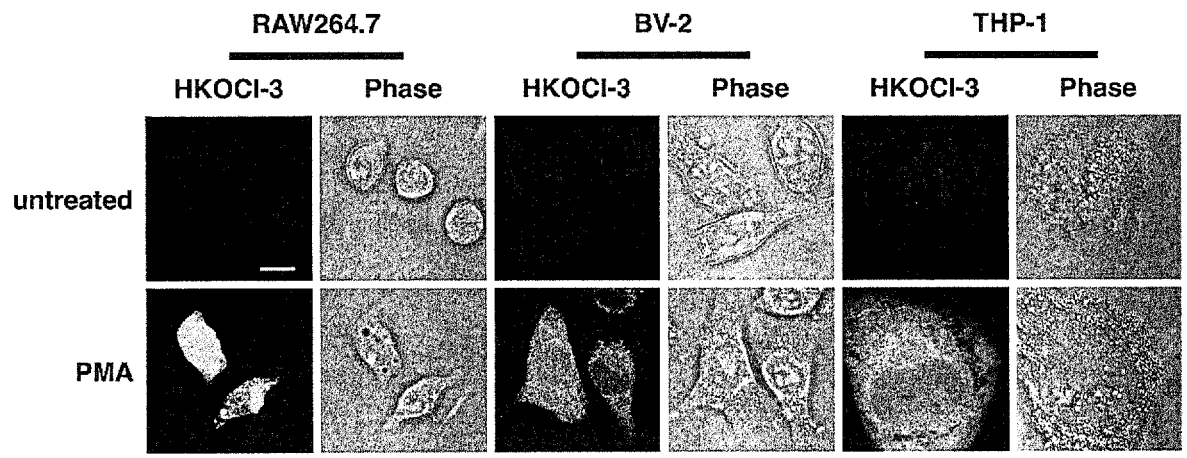
FIG. 8 confocal imaging results of three types of phagocytes (RAW264.7, BV-2 and differentiated THP-1 cells, respectively) co-incubated, before imaging, with HKOCl-3 (1 μM) with or without PMA (500 ng/mL). Scale bar represents 10 μm.
Figure 9:
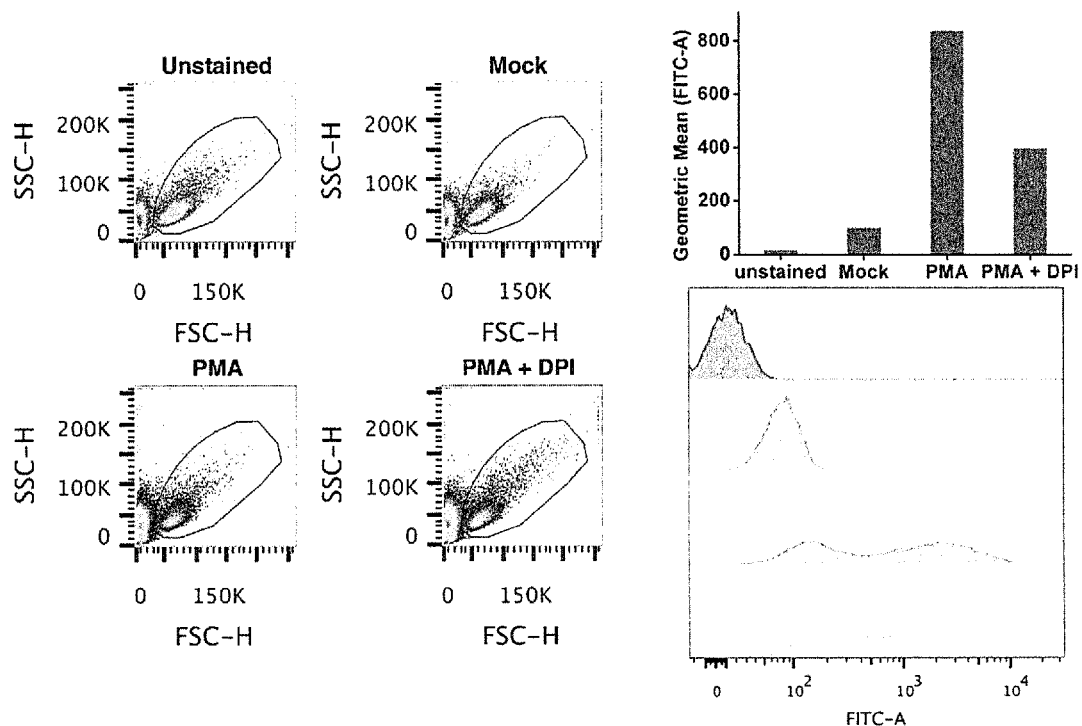
FIG. 9 shows flow cytometry results of RAW264.7 cells following co-incubation with HKOCl-3 (2 μM) with or without PMA (500 ng/mL) and DPI (100 nM) for 30 minutes.
Figure 10:
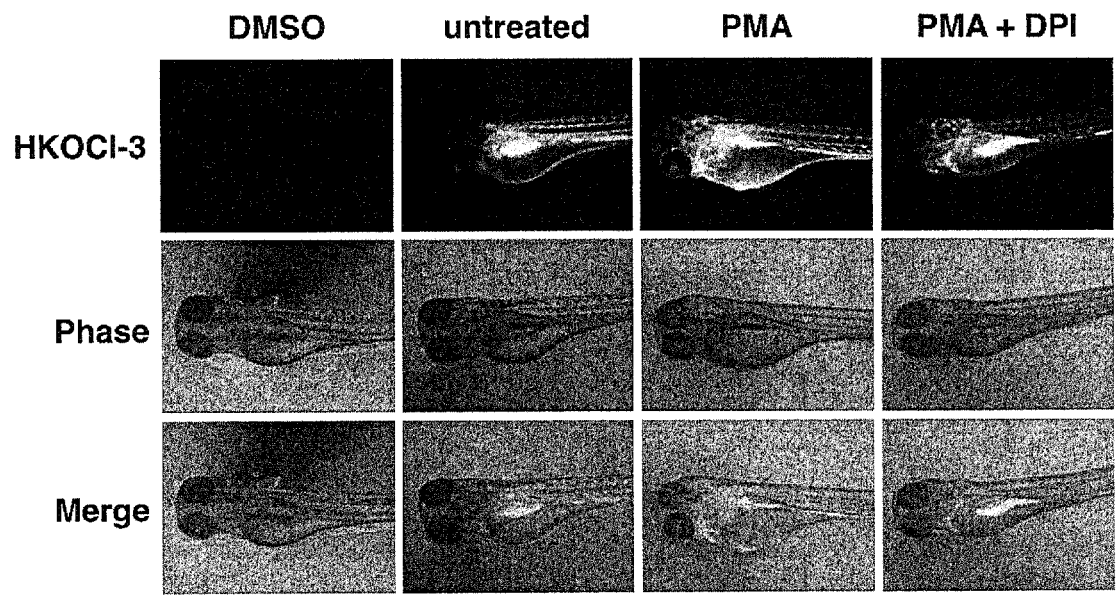
FIG. 10 shows imaging of endogenous HOCl in 72 hours post-fertilization (hpf) zebrafish embryos. At 72 hpf, the zebrafish embryos were first preloaded with HKOCl-3 (10 μM) for 20 minutes, and briefly challenged with PMA (200 ng/mL) in the absence or presence of DPI (100 nM) for 15 minutes, respectively, before imaging at magnification (10×). Merge: fluorescence and phase images merged.
Figure 11:
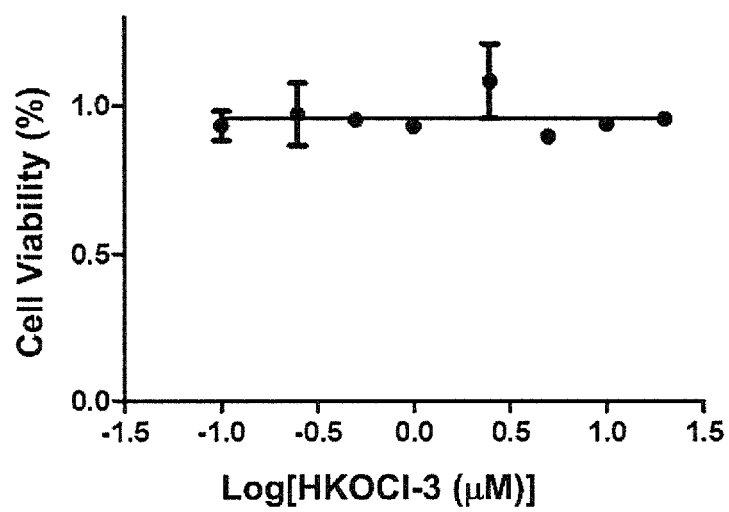
FIG. 11 shows a graphical representation of cell viability percentage for analysis of cytotoxicity of HKOCl-3 assessed by a Cell Titer Glo (Promega) luminescent cell viability assay in RAW264.7 mouse macrophages. Percent viability of HKOCl-3 was calculated. Data are mean±s.e.m. n=3 replicates.

The reactivity of compound HJ-3-259 is compared with different reactive oxygen species (ROS) and reactive nitrogen species (RNS). Specifically, the 10 μM solution of compound HJ-3-259 is treated with various ROS and RNS. The concentration of highly reactive oxygen species (hydroxyl radical ($^{\bullet}$OH), hypochlorous acid (HOCl), and peroxynitrite (ONOO$^-$)) is 10 μM. The concentration of $^1O_2$, $O_2^{\bullet-}$, $^{\bullet}$NO, ROO$^{\bullet}$, TBHP and $H_2O_2$ is 100 μM. FIG. 4B shows that treatment with hypochlorous acid results in a much higher increase in fluorescence intensity of compound HJ-3-259 than treatment with other ROS and RNS.

Example 9—Sensitive and Selective Detection of Hydroxyl Radical with Green Fluorogenic Compound HYY166

Figure 12A:
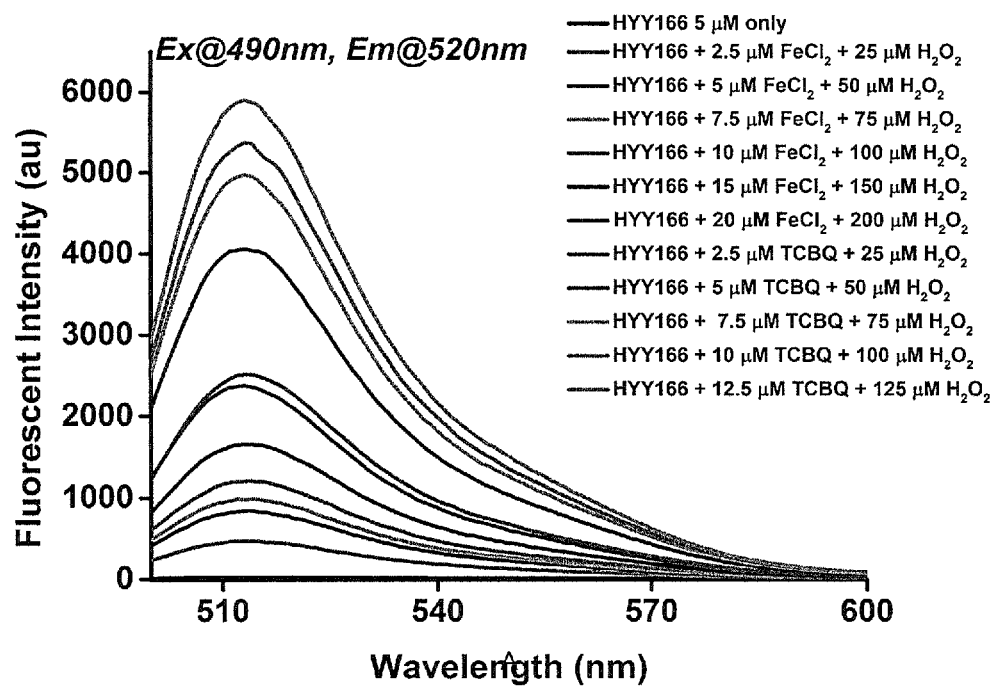
FIG. 12A shows a graph of fluorescence intensity (au) of compound HYY166 for each of HYY166 (5 μM), HYY166+2.5 μM $FeCl_2$+25 μM $H_2O_2$, HYY166+5 μM $FeCl_2$+50 μM $H_2O_2$, HYY166+7.5 μM $FeCl_2$+75 μM $H_2O_2$, HYY166+10 μM $FeCl_2$+100 μM $H_2O_2$, HYY166+15 μM $FeCl_2$+150 μM $H_2O_2$, HYY166+20 μM $FeCl_2$+200 μM $H_2O_2$, HYY166+2.5 μM TCBQ+25 μM $H_2O_2$, HYY166+5 μM TCBQ+50M $H_2O_2$, HYY166+7.5 μM TCBQ+75 μM $H_2O_2$, HYY166+10 μM TCBQ+100 μM $H_2O_2$, HYY166+12.5 μM TCBQ+125 μM $H_2O_2$.

This Example shows that green fluorogenic compound HYY166 sensitively and selectively detects hydroxyl radical. Specifically, compound HYY166 is dissolved in 0.1 M phosphate buffer at pH 7.4 to form a 5 μM solution, with excitation and emission spectra at 490 nm and 520 nm, respectively. The 5 μM solution of compound HYY166 is treated with hydroxyl radical generated from different hydroxyl radical source: (1) Fenton reagent ([$H_2O_2$]:[$FeCl_2$]=10:1); (2) Tetrachloro-1,4-benzoquinone (TCBQ)/$H_2O_2$ ([$H_2O_2$]:[TCBQ]=10:1) system. FIG. 12A shows that the florescence intensity of compound HYY166 increases with increasing concentration of hydroxyl radical source.

Figure 12B:
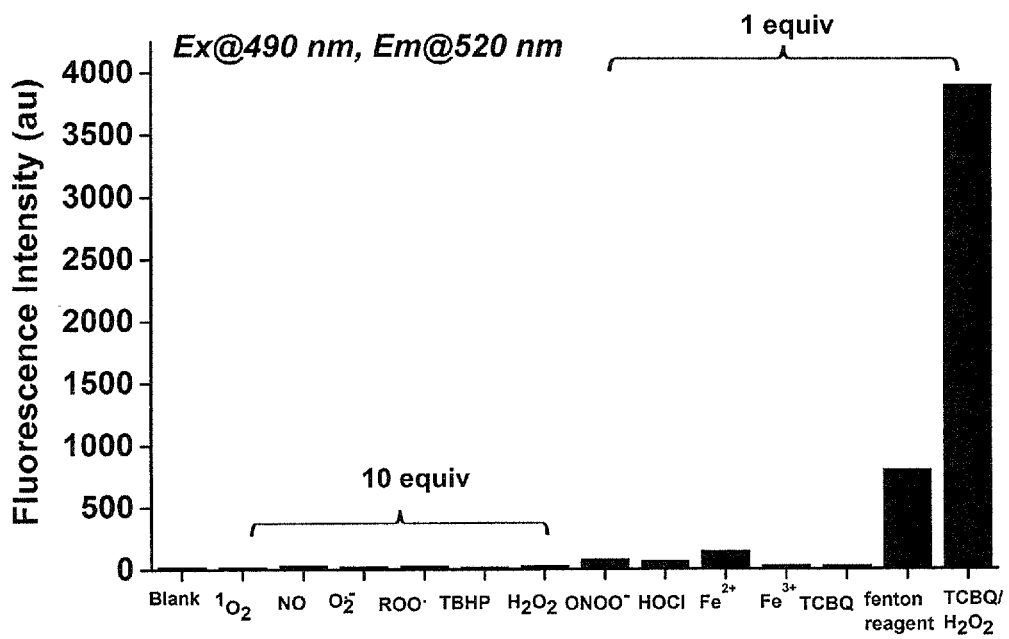
FIG. 12B shows a graph of fluorescence intensity (au) of compound HYY166 treated with various ROS and RNS.

The reactivity of compound HYY166 is tested toward different reactive oxygen species (ROS), reactive nitrogen species (RNS), $FeCl_2$, $FeCl_3$ and TCBQ. Specifically, the 5 μM solution of compound HYY166 is treated with various ROS and RNS. The concentration of highly reactive oxygen species (hydroxyl radical ($^{\bullet}$OH), hypochlorous acid (HOCl), and peroxynitrite (ONOO$^-$)), $FeCl_2$, $FeCl_3$ and TCBQ is 5 μM. The concentration of $^1O_2$, $O_2^{\bullet-}$, $^{\bullet}$NO, ROO$^{\bullet}$, TBHP and $H_2O_2$ is 50 μM. FIG. 12B shows that treatment with hydroxyl radical, especially generated from the TCBQ/$H_2O_2$ system, results in a much higher increase in fluorescence intensity of compound HYY166 than treatment with other ROS and RNS.

Example 10—Sensitive and Selective Detection of Hydroxyl Radical with Green Fluorogenic Compound HKOH-1

Figure 13A:
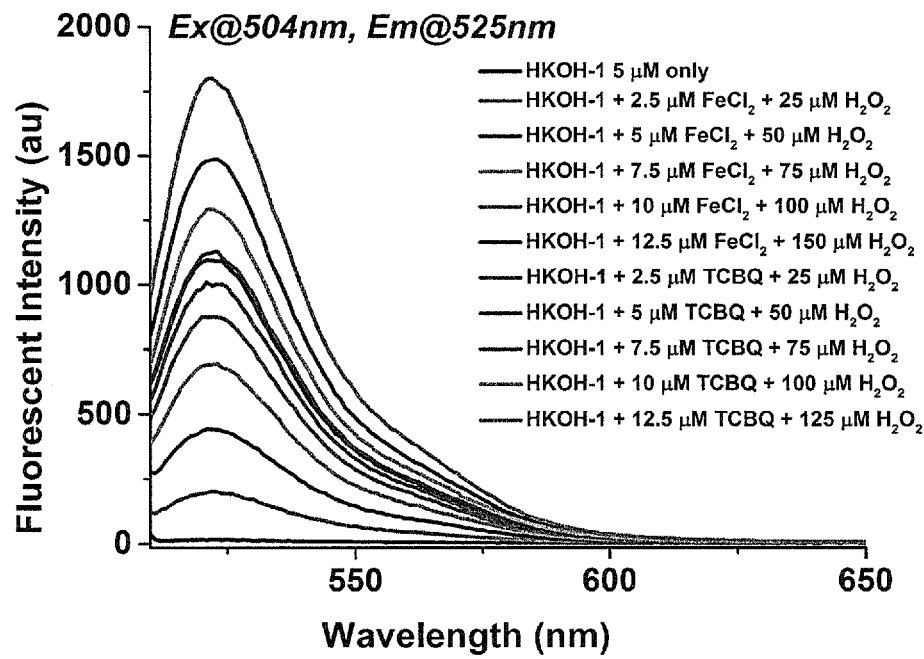
FIG. 13A shows a graph of fluorescence intensity (au) of compound HKOH-1 for each of HKOH-1 (5 μM), HKOH-1+2.5 μM $FeCl_2$+25 μM $H_2O_2$, HKOH-1+5 μM $FeCl_2$+50 μM $H_2O_2$, HKOH-1+7.5 μM $FeCl_2$+75 μM $H_2O_2$, HKOH-1+10 μM $FeCl_2$+100 μM $H_2O_2$, HKOH-1+12.5 μM $FeCl_2$+150 μM $H_2O_2$, HKOH-1+2.5 μM $TCBQFeCl_2$+25 μM $H_2O_2$, HKOH-1+5 μM TCBQ+50 μM $H_2O_2$, HKOH-1+7.5 μM TCBQ+75 μM $H_2O_2$, HKOH-1+10 μM TCBQ+100 μM $H_2O_2$, HKOH-1+12.5 μM TCBQ+125 μM $H_2O_2$.

This Example shows that green fluorogenic compound HKOH-1 sensitively and selectively detects hydroxyl radical. Specifically, compound HKOH-1 is dissolved in 0.1 M phosphate buffer at pH 7.4 to form a 5 μM solution, with excitation and emission spectra at 504 nm and 525 nm, respectively. The 5 μM solution of compound HKOH-1 is treated with hydroxyl radical generated from different hydroxyl radical source: (1) Fenton reagent ($[H_2O_2]$:$[FeCl_2]$=10:1); (2) Tetrachloro-1,4-benzoquinone (TCBQ)/$H_2O_2$ ($[H_2O_2]$:$[TCBQ]$=10:1) system. FIG. 13A shows that the florescence intensity of compound HKOH-1 increases with increasing concentration of hydroxyl radical source.

Figure 13B:
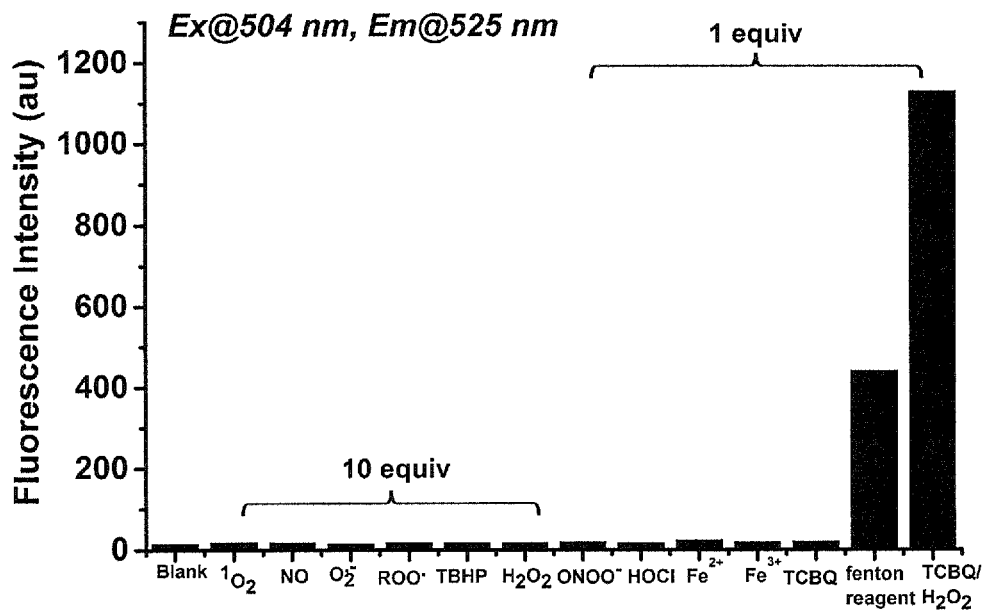
FIG. 13B shows a graph of fluorescence intensity (au) of compound HKOH-1 treated with various ROS and RNS.

The reactivity of compound HKOH-1 is compared toward different reactive oxygen species (ROS), reactive nitrogen species (RNS), $FeCl_2$, $FeCl_3$ and TCBQ. Specifically, the 5 μM solution of compound HKOH-1 is treated with various ROS and RNS. The concentration of highly reactive oxygen species (hydroxyl radical ($^{\bullet}OH$), hypochlorous acid (HOCl), and peroxynitrite ($ONOO^-$)), $FeCl_2$, $FeCl_3$ and TCBQ is 5 μM. The concentration of $^1O_2$, $O_2^{\bullet-}$, $^{\bullet}NO$, $ROO^{\bullet}$, TBHP and $H_2O_2$ is 50 μM. FIG. 13B shows that treatment with hydroxyl radical, especially generated from the TCBQ/$H_2O_2$ system, results in a much higher increase in fluorescence intensity of compound HKOH-1 than treatment with other ROS and RNS.

Example 11—Application of Subject Compounds in Cell Assay

RAW264.7 cells, a mouse monocytic macrophage line, were acquired from ATCC (American Type Culture Collection) and maintained in DMEM (Dulbecco's Modified Eagle Medium) supplemented with 10% heat-inactivated fetal bovine serum (Gibco) and 1% penicillin/streptomycin, at 37° C. with 5% $CO_2$. The growth medium was renewed every two to three days. At 80% confluence, the cells were detached by scraping, washed with fresh medium and spun down (500 rpm in Eppendorf microfuge) for cell counting. For confocal imaging, cells were typically seeded at a density of $2\times10^4$ cells/mL in 35-mm confocal dish (Mat-Tek: MA, USA). BV-2 mouse microglia were obtained as a gift from Department of Pediatrics, University of Hong Kong, and maintained in the same manner as RAW264.7 cells. HCT116 human colon carcinoma cells were obtained from ATCC, and maintained in McCoy's medium with serum and appropriate antibiotics. THP-1 human monocytes were acquired as a gift from Prof. Lijian Jin, School of Dentistry, The University of Hong Kong, and maintained in RPMI (ATCC) supplemented with 10% heat-inactivated fetal bovine serum (Gibco), 1% penicillin/streptomycin, and 55 M β-mercaptoethanol, at 37° C. in 5% $CO_2$. Prior to drug treatment, THP-1 monocytes were differentiated into mature macrophages with low-dose PMA (5 ng/mL) as previously described.

For acute HOCl induction (30 min), PMA or zymosan was added at specified doses to HBSS (Hank's balanced salt solution, supplemented with 0.6 mM L-arginine, 0.01% chloramphenicol) and co-incubated with our fluorescent probe until imaging (see FIGS. 5-11). Enzyme inhibitors (such as NOX inhibitor DPI, and MPO inhibitor ABAH) and HOCl scavenger (such as taurine) were added along with PMA or zymosan during HOCl induction.

Figure 14:
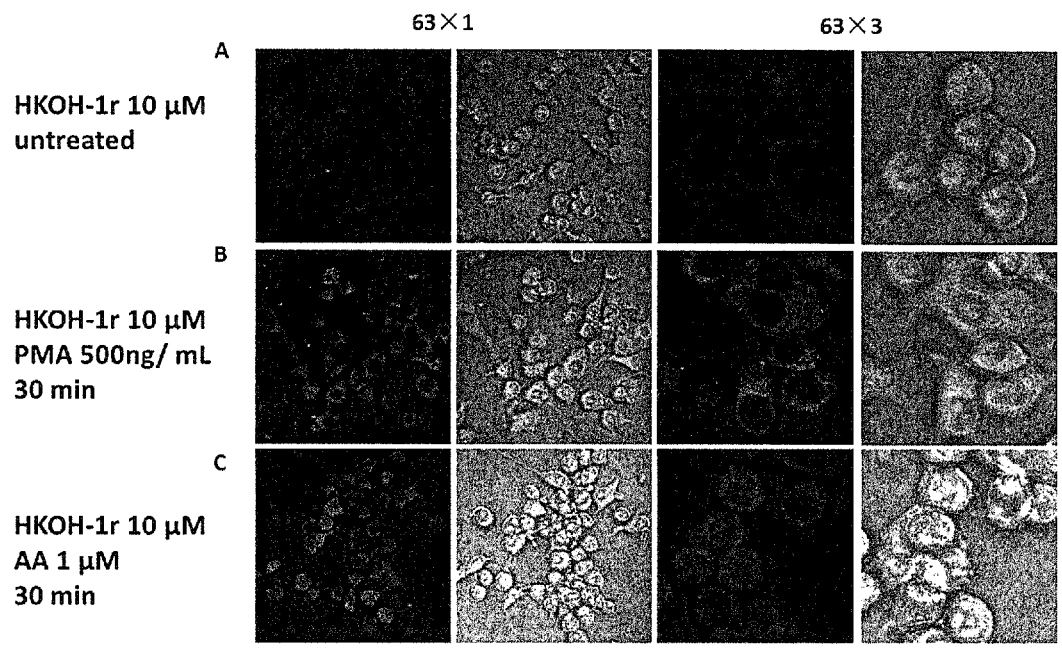
FIG. 14 depicts representative confocal images for RAW264.7 cells with HKOH-1r (10 μM). (A) Cells incubated with HKOH-1r without treatment; (B) Cells co-incubated with HKOH-1r and 500 ng/mL PMA for 30 min; (C) Cells co-incubated with HKOH-1r and 1 μM Antimycin A for 30 min.
Figure 15:
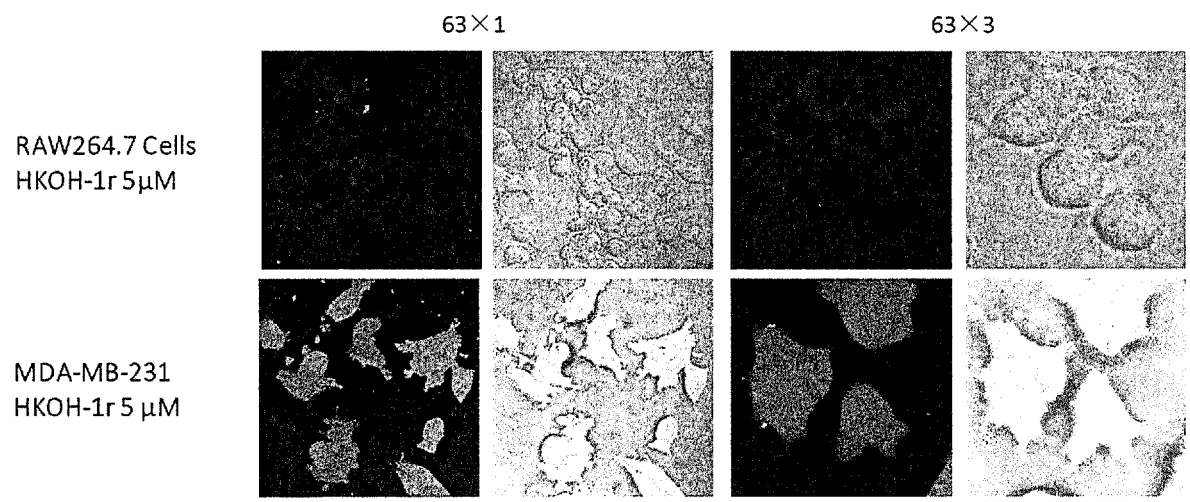
FIG. 15 depicts representative confocal images of RAW264.7 cells and MDA-MB-231 with basal level of hydroxyl radical. Two types of cells were co-incubated with HKOH-1r (5 μM) without any treatment for 30 min, before confocal imaging.

For acute hydroxyl radical ($^{\bullet}OH$) induction, PMA or Antimycin A was added at specified doses to HBSS (Hank's balanced salt solution, supplemented with 0.6 mM L-arginine, 0.01% chloramphenicol) and co-incubated with fluorescent probe HKOH-1r for 30 min until imaging (see FIG. 14). It is known that cancer cells, compared to normal cells, are under increased oxidative stress and increased generation of ROS. Thus, the difference in the basal level of $^{\bullet}OH$ between cancer and normal cells was tested with HKOH-1r (see FIG. 15).

We claim:

1. A compound or a tautomer thereof, wherein the compound has one of structures 21-36 or 46-61:

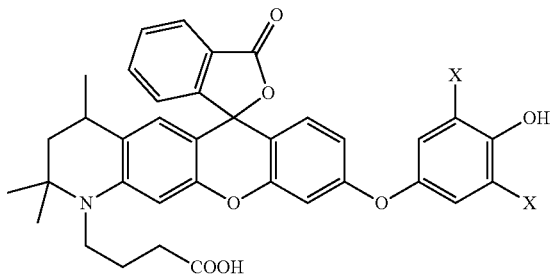

21

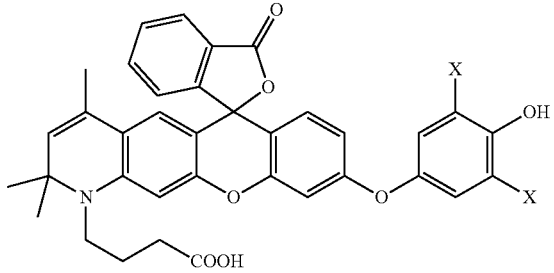

22

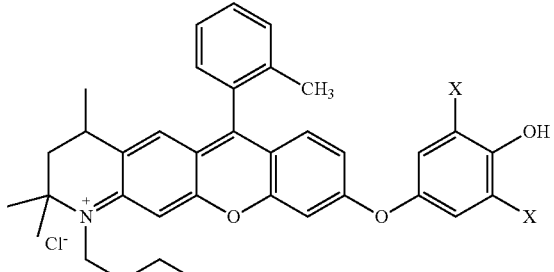

23

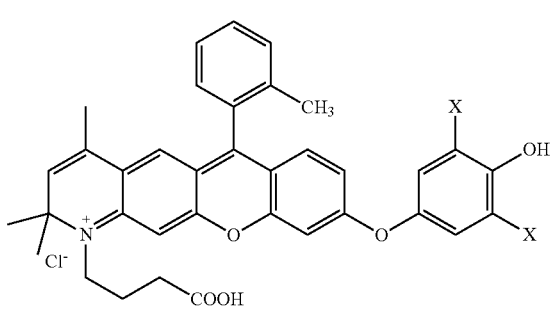

24

25
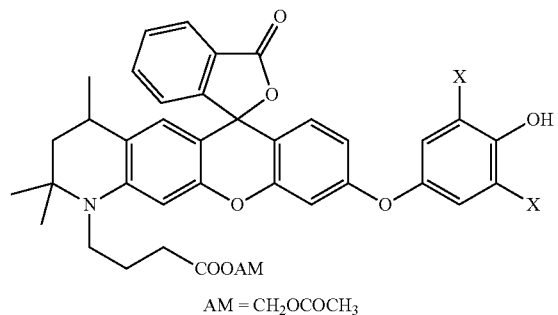
AM = CH₂OCOCH₃
26
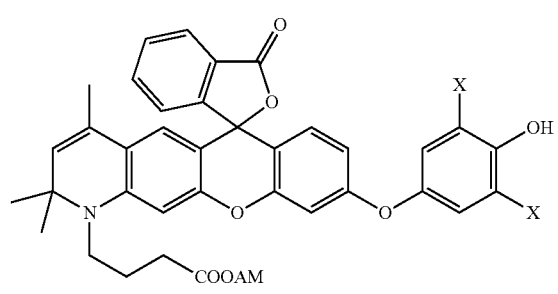
27
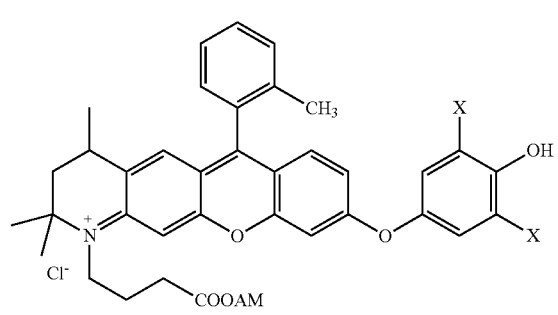
28
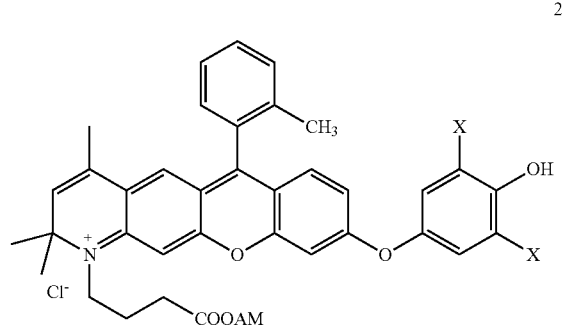
29
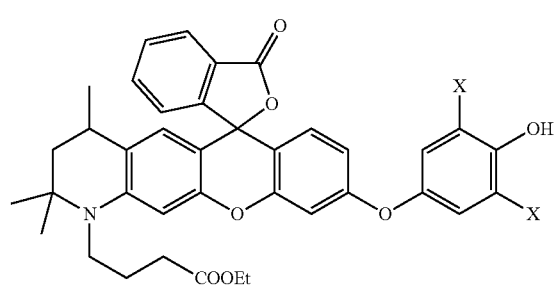
30
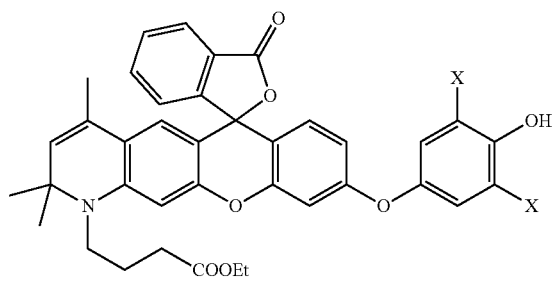
31
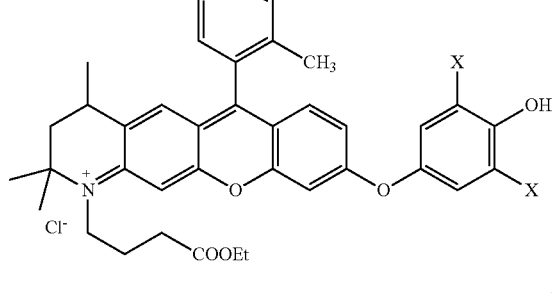
32
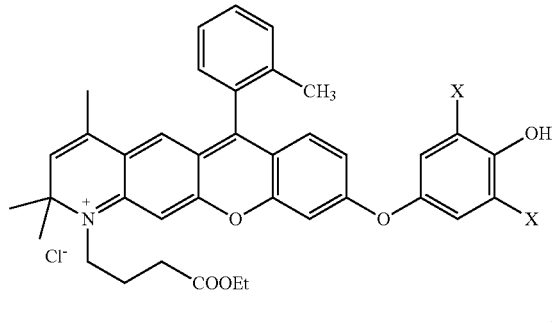
33
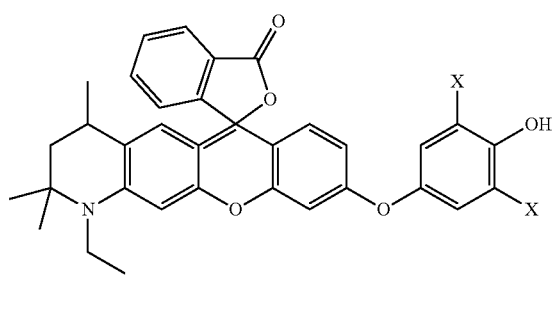
34
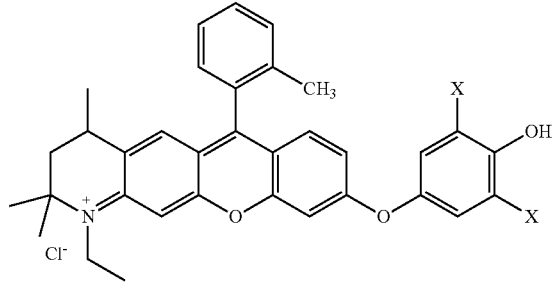

35
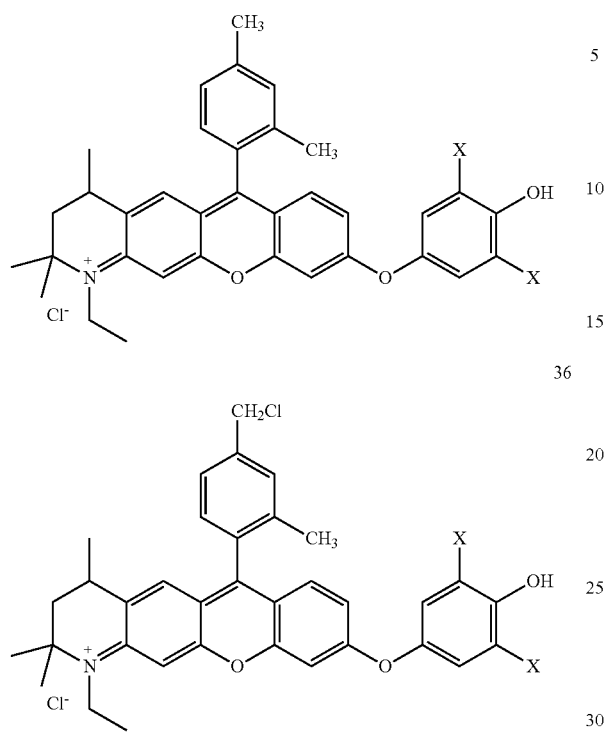
36
X = F, Cl, Br, or I
46
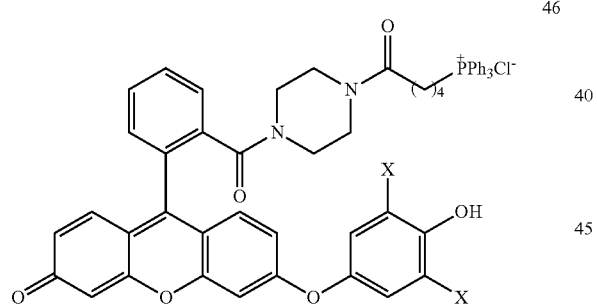
47
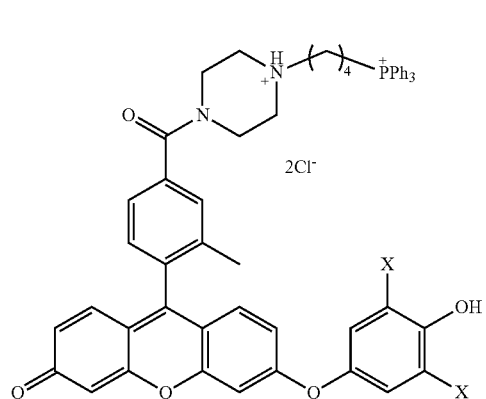
48
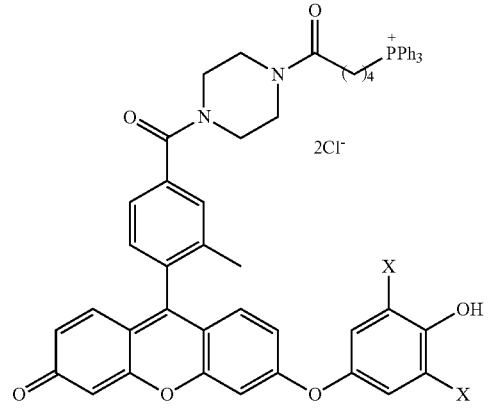
49
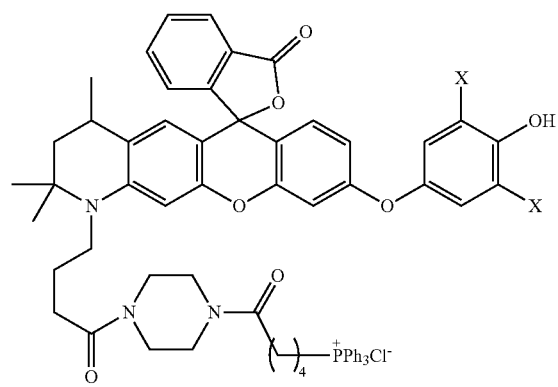
50
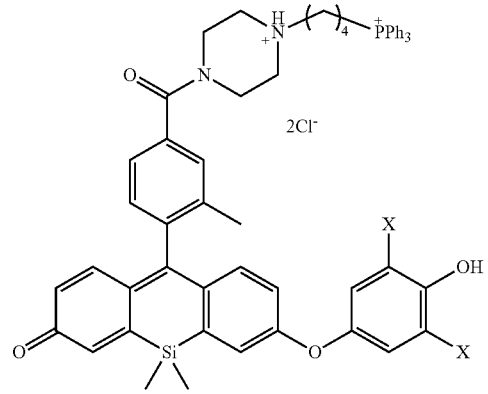

65
-continued
51
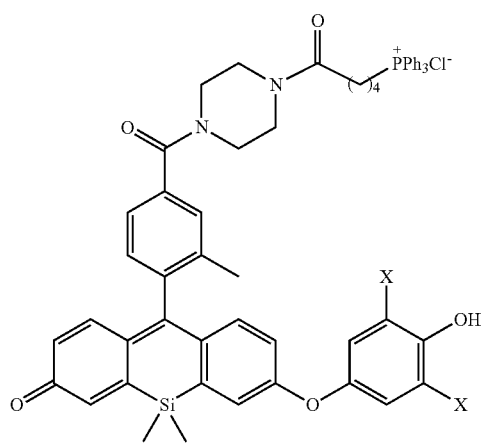
X = F, Cl, Br, or I
52
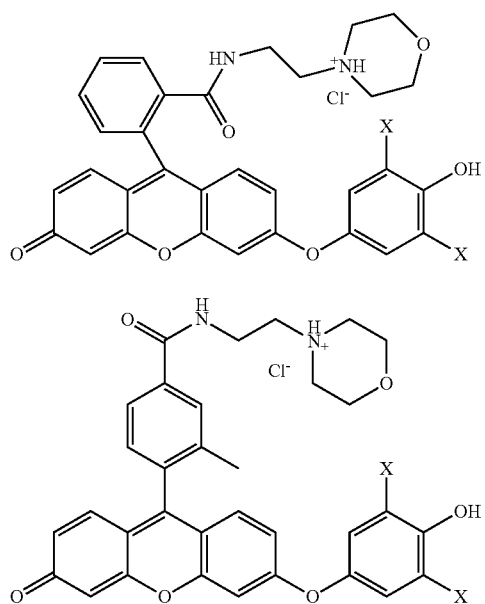
53
54
66
-continued
55
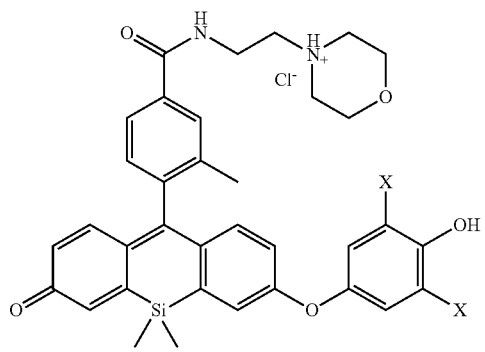
56
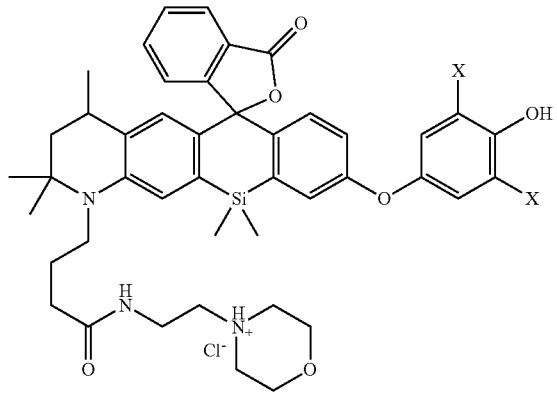
57
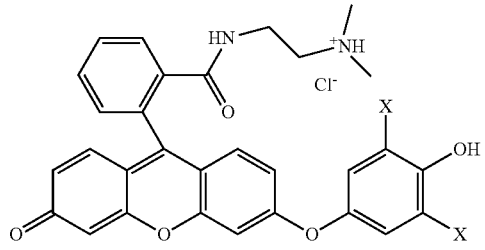
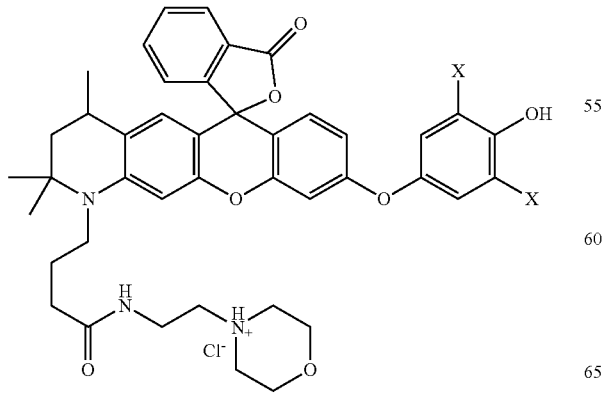

58

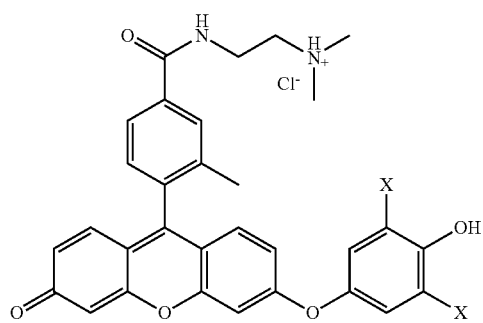

59

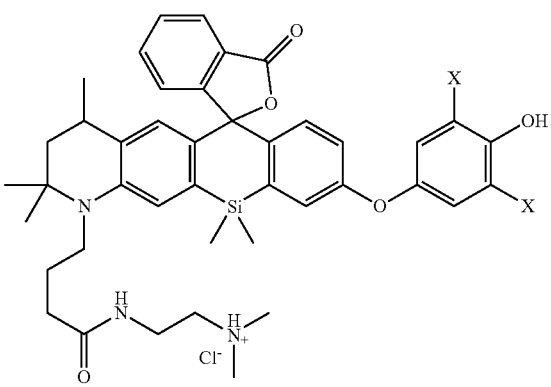

60

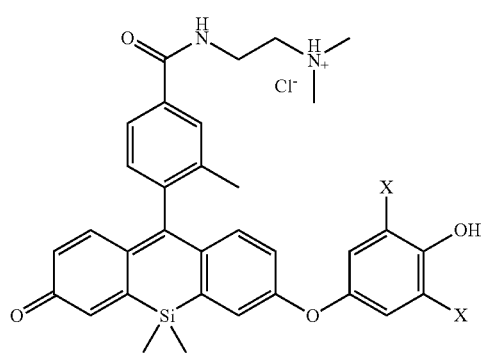

61

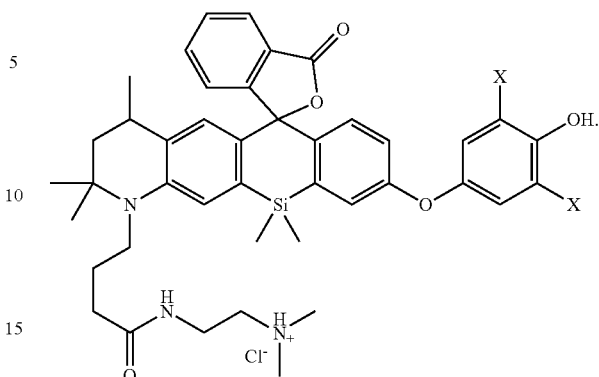

X = F, Cl, Br, or I

2. A fluorogenic probe composition comprising the compound of claim 1, and, optionally, a carrier.

3. The fluorogenic probe composition of claim 2, wherein the fluorogenic probe composition further comprises a solvent, an acid, a base, a buffer solution, or a combination thereof.

4. A method for detecting the presence of, and/or determining the level of superoxide in a sample, comprising:
 a) contacting a compound of claim 1 with the sample to form a fluorescent compound; and
 b) determining fluorescence property of the fluorescent compound.

5. The method of claim 4, wherein the sample is a chemical sample or biological sample.

6. The method of claim 5, wherein the sample is a biological sample comprising a microorganism, or a cell or tissue.

7. A method for detecting the presence of, or determining the level of hypochlorous acid or hydroxyl radical in vivo in an organism, comprising:
 a) administering a compound of claim 1 to the organism to form a fluorescent compound; and
 b) determining fluorescence property of the fluorescent compound.

8. A high-throughput screening method for detecting the presence of, or determining the level of, hypochlorous acid or hydroxyl radical in samples, wherein the high-throughput method comprises the steps of:
 a) contacting a compound of claim 1 with the samples to form one or more fluorescent compounds; and
 b) determining fluorescence properties of the fluorescent compounds to determine the presence and/or amount of hypochlorous acid or hydroxyl radical in the samples.

9. A high-throughput method for screening one or more target compounds that increase or decrease the level of hypochlorous acid or hydroxyl radical, wherein the high-throughput method comprises the steps of:
 a) contacting a compound of claim 1 with target compounds to form one or more fluorescent compounds; and
 b) measuring fluorescence properties of the florescent compounds to determine the presence and/or amount of the target compounds.

* * * * *